United States Patent [19]
Itoh et al.

[11] Patent Number: 5,405,861
[45] Date of Patent: Apr. 11, 1995

[54] TRIAZOLE COMPOUNDS AND ANTIFUNGAL COMPOSITIONS THEROF

[75] Inventors: Katsumi Itoh, Toyono; Kenji Okonogi, Mishima, both of Japan

[73] Assignee: Takeda Chemical Industries, Co., Ltd., Japan

[21] Appl. No.: 232,337

[22] Filed: Apr. 22, 1994

Related U.S. Application Data

[63] Continuation of Ser. No. 930,470, Aug. 20, 1992, abandoned, which is a continuation of Ser. No. 588,334, Sep. 26, 1990, abandoned.

[30] Foreign Application Priority Data

Sep. 26, 1989 [JP] Japan .................................. 1-251176
Dec. 14, 1989 [JP] Japan .................................. 1-325166
Mar. 7, 1990 [JP] Japan .................................. 2-056201
May 10, 1990 [JP] Japan .................................. 2-122081

[51] Int. Cl.$^6$ ..................... A61K 31/41; C07D 403/12
[52] U.S. Cl. ............................. 514/383; 548/268.6
[58] Field of Search ....................... 514/383; 548/268.6

[56] References Cited

U.S. PATENT DOCUMENTS 4,505,919  3/1985  Cooper et al. ................. 514/340
4,678,789  7/1987  Richardson et al. ........... 514/262

FOREIGN PATENT DOCUMENTS 61835   10/1982  European Pat. Off.
0095828 12/1983  European Pat. Off.
0178533  4/1986  European Pat. Off.
0322800  7/1989  European Pat. Off.
332387   9/1989  European Pat. Off.

*Primary Examiner*—Mary C. Lee
*Assistant Examiner*—Jacqueline Haley
*Attorney, Agent, or Firm*—Foley & Lardner

[57] ABSTRACT

The novel 2-(2,4-difluorophenyl)-1-(1H-1,2,4-triazol-1-yl)-2-propanol derivertives of the formula (I):

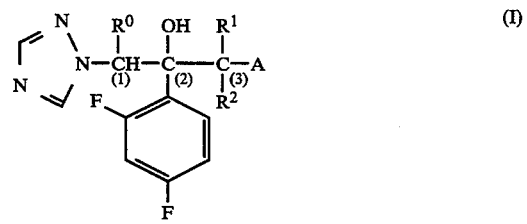

wherein, $R^0$, $R^1$ and $R^2$ are the same or different and represent a hydrogen atom or a lower alkyl group; A represents a formula:

$$-\overset{(O)_n}{\underset{}{S}}-X-R^3 \quad \text{or} \quad -S-R^4$$

wherein, X stands for a chemical bond or a formula:

$$-\overset{R^5}{\underset{R^6}{C}}-X'-$$

(wherein, X' stands for a chemical bond or an alkylene group having 1 to 5 carbon atoms which may contain sulfur or oxygen atom as the constituent atoms, $R^5$ and $R^6$ are the same or different and stand for a hydrogen atom or a lower alkyl group), $R^3$ stands for an aromatic heterocyclic group which may be substituted, n denotes 0, 1 or 2), and $R^4$ stands for a hydrogen atom or an alkanoyl group, or a physiologically acceptable salt thereof have antifungal activities, and they are used for preventing or treating infectious diseases caused by fungi.

8 Claims, 2 Drawing Sheets

TRIAZOLE COMPOUNDS AND ANTIFUNGAL COMPOSITIONS THEROF

This application is a continuation of U.S. application Ser. No. 07/930,470 filed Aug. 20, 1992, abandoned; which is a continuation of U.S. application Ser. No. 07/588,334 filed Sep. 26, 1990, now abandoned.

FIELD OF THE INVENTION

This invention relates to triazole compounds, their production and use. The said compounds are useful as antifungal agents or the intermediate for their synthesis, being useful in the field of drugs and agricultural chemicals.

BACKGROUND OF THE INVENTION

Various compounds have been reported as antifungal agents.

For example, triazole derivatives were disclosed as compounds having antifungal activities in the gazette of Japanese Unexamined Patent Publication No. 189173/83 and No. 98072/84. However, it is difficult to say that these compounds are effective enough as drugs from the standpoints of their antifungal activity, side effect, and absorption.

Conventional antifungal therapeutics are not sufficiently effective, having various problems such as occurrence of side effects, replacement of fungus, and resistance.

To solve such problems, compounds having higher safety and more potent antifungal activities have been desired as antifungal therapeutics.

SUMMARY OF THE INVENTION

Figure 1:
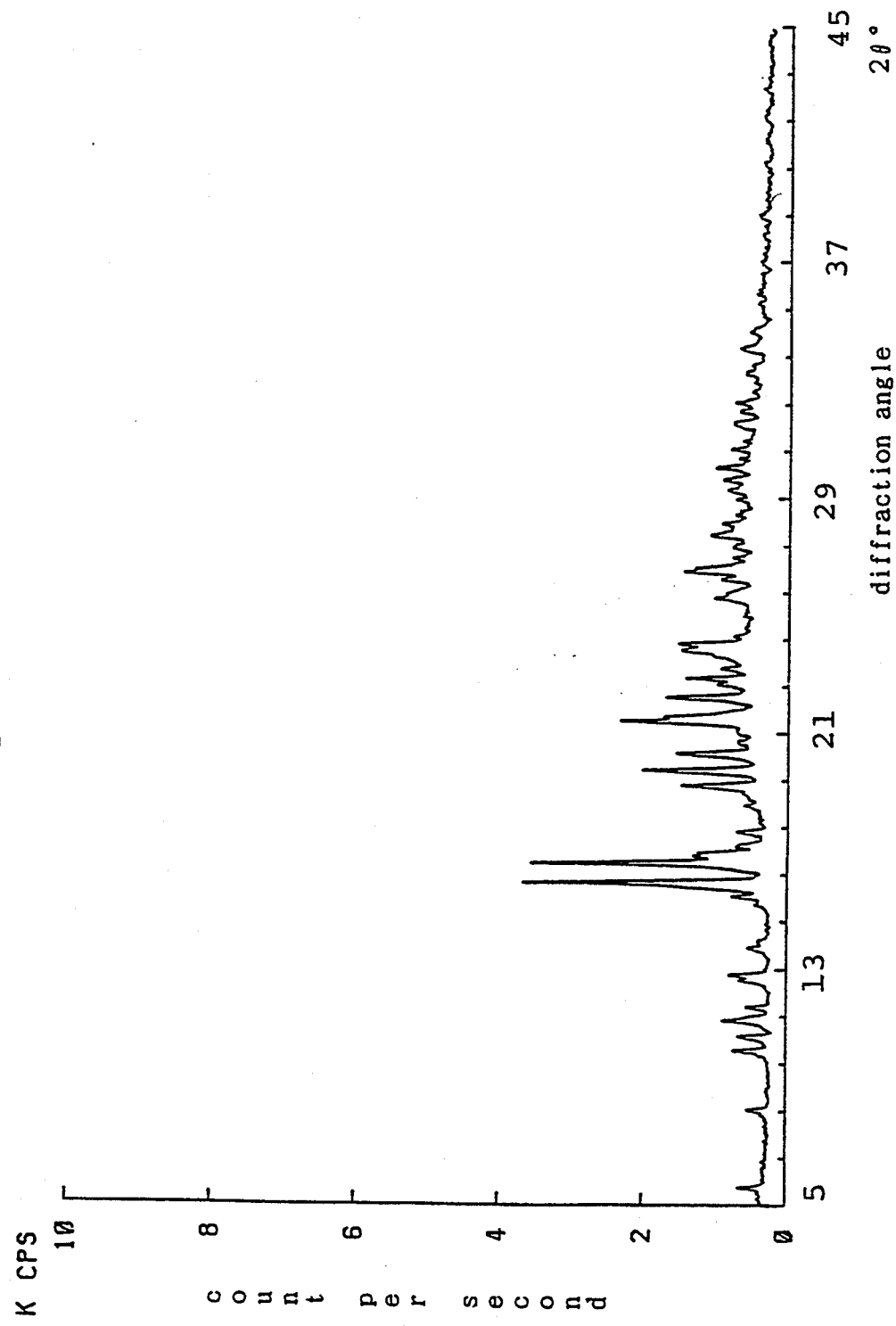
FIG. 1 shows an X-ray powder diffraction pattern of compound 43 hydrochloride.

This invention relates to:
1. A compound of the formula (I):

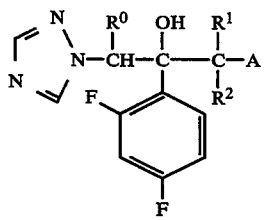

wherein, $R^0$, $R^1$ and $R^2$ are the same or different and represent a hydrogen atom or a lower alkyl group; A represents a formula:

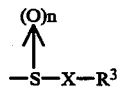

[wherein, X stands for a chemical bond or a formula:

(wherein, X' stands for chemical bond or an alkylene group having 1 to 5 carbon atoms which may contain sulfur or oxygen atom as the constituent atoms, $R^5$ and $R^6$ are the same or different and stand for a hydrogen atom or a lower alkyl group), $R^3$ stands for an aromatic heterocyclic group which may be substituted, n denotes 0, 1 or 2], or a formula:

(wherein, $R^4$ stands for a hydrogen atom or an alkanoyl group), provided that $R^0$ or $R^1$ is lower alkyl group when X or X' in A is a chemical bond or A stands for a formula:

(wherein, $R^4$ is the same as defined above), or a salt and especially a physiologically acceptable salt thereof.
2. A method for producing a compound of the formula (I).
3. Antifungal agents containing a compound of the formula (I).

DETAILED DESCRIPTION OF THE INVENTION

This invention provides a compounds of a formula (I):

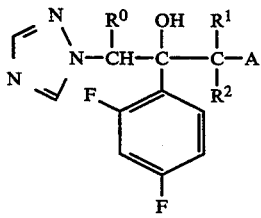

wherein, $R^0$, $R^1$ and $R^2$ are the same or different and represent a hydrogen atom or a lower alkyl group; A represents a formula:

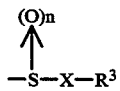

[wherein, X stands for chemical bond or a formula:

(wherein, X' stands for chemical bond or an alkylene group having 1 to 5 carbon atoms which may contain sulfur or oxygen atom as the constituent atoms, $R^5$ and $R^6$ are the same or different and stand for a hydrogen atom or a lower alkyl group), $R^3$ stands for an aromatic heterocyclic group which may be substituted, n denotes 0, 1 or 2], or A represents a formula:

—S—R⁴

(wherein, R⁴ stands for a hydrogen atom or an alkanoyl group), provided that R⁰ or R¹ is a lower alkyl group when X or X' in A is a chemical bond or A stands for a formula:

—S—R⁴

(wherein, R⁴ is the same as defined above), or a salt thereof.

2. A method for producing a compound of the formula (I).
3. Antifugal agents containing a compound of the formula (I).

The compounds of this invention can also be represented by the general formula:

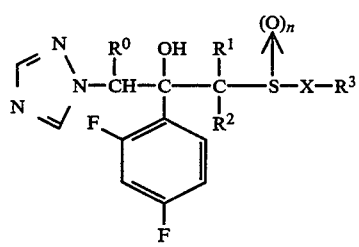   (I')

wherein R⁰, R¹, R², R³, X and n are the same as defined above, and the general formula:

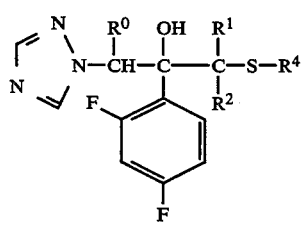   (I")

wherein R⁰, R¹, R² and R⁴ are the same as defined above.

In the compounds (I), the lower alkyl groups represented by R⁰, R¹ or R² include straight chain or branched $C_{1-3}$ alkyl groups such as methyl, ethyl, propyl, and isopropyl or lower alkylene groups comprising conbination of R¹ and R² (e.g. ethylene, propylene) and the compounds having a methyl group as R¹ and a hydrogen atom as R⁰ and R² in the formula (I) are desirable.

In the compounds (I), when X in A is represented by the formula

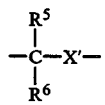

a desirable example for hydrogen atom or lower alkyl groups (e.g. methyl, ethyl, propyl) represented by R⁵ or R⁶ is a hydrogen atom or methyl; desirable examples for the alkylene group represented by X which contain 1 to 5 carbon atoms and may contain sulfur or oxygen atoms as the constituent atoms include

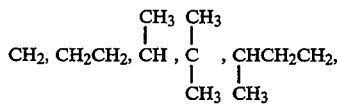

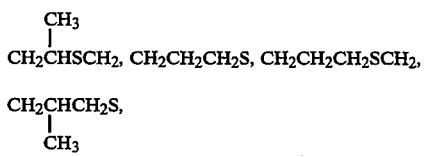

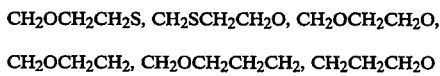

$CH_2OCH_2CH_2S$, $CH_2SCH_2CH_2O$, $CH_2OCH_2CH_2O$, $CH_2OCH_2CH_2$, $CH_2OCH_2CH_2CH_2$, $CH_2CH_2CH_2O$

When X' is an alkylene group containing sulfur atoms as the constituent atoms, the said sulfur atoms may be oxidized to form a sulfoxide or sulfone. When these groups which have chemical bonds at both sides have sulfur or oxygen atom at the end, these atoms connect R³.

In the compounds (I), when A represents

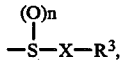

the aromatic heterocyclic group represented by R³ which may be substituted may be condensed with a 5- to 7-membered ring; the said condensed aromatic heterocyclic groups are exemplified by 1-benzimidazolyl, 2-benzimidazolyl, 5H-6,7-dihydropyrrolo[1,2-a]imidazol-2-yl, 5H-6,7-dihydropyrrolo[1,2-c]imidazol-3-yl, 2-imidazo[1,2-a]pyrimidinyl, 5,6,7,8-tetrahydroimidazo[1,2-a]pyridin-2-yl, 2-imidazo[1,2-a]pyridinyl, 3-imidazo[1,5-a]pyrazinyl, 2-imidazo[1,2-a]pyrazinyl, 6-imidazo[1,2-b]pyridazinyl, 2-imidazo[1,2-b]pyridazinyl, 3-imidazo[1,2-b]pyridazinyl, 5-imidazo[1,5-a]pyridinyl, 6-imidazo[1,5-a]pyridinyl, 3-imidazo[1,5-a]pyrimidinyl, 7-imidazo[1,5-b]pyridazinyl, 2-benzothiazolyl, 4,5,6,7-tetrahydrobenzothiazol-2-yl, 4H-5,6-dihydrocyclopenta[d]thiazol-2-yl, 4H-5,6,7,8-tetrahydrocyclohepta[d]thiazol-2-yl, quinolyl, isoquinolyl, quinazolinyl, indolizinyl, and indolyl.

Non-condensed heterocyclic groups in the aromatic heterocyclic group represented by R³ which may be substituted include 1-imidazolyl, 2-imidazolyl, 4-imidazolyl, 5-imidazolyl, 1-(1H)-1,2,4-triazolyl, 3-(4H)-1,2,4-triazolyl, 3-(1H)-1,2,4-triazolyl, 5-(1H)-1,2,4-triazolyl, 4-(4H)-1,2,4-triazolyl, 1,2,3-triazolyl, 1-pyrazolyl, 3-pyrazolyl, 4-pyrazolyl, 4-pyridyl, 2-pyridyl, 3-pyridyl, 2-thiazolyl, 4-thiazolyl, 5-thiazolyl, 1,2,4-thiadiazol-3-yl, 1,2,4 -thiadiazol-5-yl, 1,3,4-thiadiazol-2-yl, 2-thienyl, 2-furyl, 1-pyrrolyl, 2-pyrazinyl, 3-pyrimizinyl, 2-pyrimidinyl, 4-pyrimidinyl, 5-pyrimidinyl, 3-isoxazolyl, 2-oxazolyl, 4-oxazolyl, 5-oxazolyl, 1-tetrazolyl, 5-tetrazolyl and 2-oxo-1,3-dioxol-4-yl.

The substituents which the condensed or non-condensed aromatic heterocyclic group may have include amino, hydroxy, halogen atoms, alkyl, alkenyl, aryl, aralkyl, halogenated alkyl, alkylthio groups, cycloalkyl groups and cycloalkylalkyl groups; the said halogen atoms include fluorine, chlorine, bromine and iodine atoms.

The said alkyl group is desirably one having 1 to 4 carbon atoms each, including straight chain or branched alkyl group such as methyl, ethyl, n-propyl, isopropyl, butyl, isobutyl, sec-butyl, and tert-butyl.

The said alkenyl group includes those having 2 to 4 carbon atoms each, being exemplified by vinyl, allyl, and 1,3-butadienyl.

The said aryl group includes phenyl and naphthyl.

The said aralkyl group includes benzyl, phenethyl, and phenylpropyl.

The said halogenated alkyl group includes alkyl groups having 1 to 4 carbon atoms each substituted with 1 to 5 halogen atoms, being exemplified by fluoromethyl, difluoromethyl, trifluoromethyl, fluoroethyl, difluoroethyl, trifluoroethyl, difluoropropyl and tetrafluoropropyl.

The said alkylthio group includes those having 1 to 4 carbon atoms, being exemplified by methylthio, ethylthio, propylthio, and butylthio; the sulfur atom in the said alkylthio groups may be oxidized to form sulfoxide or sulfone.

The said cycloalkyl group includes those having 3 to 6 carbon atoms each, being examplified cyclopropyl, cyclobutyl, cyclopentyl, cyclohexyl.

The said cycloalkylalkyl group includes alkyl groups having 1 to 4 carbon atoms each substituted with cycloalkyl groups having 3 to 6 carbon atoms each, being exemplified cyclopropylmethyl, cyclobutylmethyl, cyclopentylmethyl, cyclohexylmethyl, cyclopropylethyl, cyclopropylbutyl.

In the compounds (I), when A represented —S—$R^4$, the alkanoyl group represented by $R^4$ include the acyl groups derived from carboxylic acids, being exemplified by $C_{2-5}$alkanoyl group such as propionyl, butyryl, isobutyryl, and valeryl, acetyl, and aryl-$C_{1-3}$alkanoyl group such as phenylacetyl and phenylpropionyl. The said acyl group is desirably one which can be hydrolyzed in the body.

In the compounds (I), wherein A represents —S—$R^4$, the carbon asymmetric center which connects with a hydroxyl group desirably has R-configaration.

Compounds of this invention are specifically disclosed in Tables 1, 2, 3-1 and 3-2.

TABLE 1

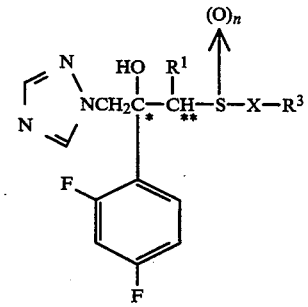

| Compound No. | $R^1$ | n | X | $R^3$ | Configuration C* | C** |
|---|---|---|---|---|---|---|
| 1 | H | 0 | —CH₂CH₂— | benzimidazolyl | RS | — |
| 2 | H | 0 | —CH₂CH₂— | 1,2,4-triazolyl | RS | — |
| 3 | H | 2 | —CH₂CH₂— | 1,2,4-triazolyl | RS | — |
| 4 | H | 1 | —CH₂CH₂— | 1,2,4-triazolyl | RS | — |
| 5 | H | 0 | —CH₂CH₂— | imidazolyl | RS | — |

TABLE 1-continued

[Structure: triazole-NCH₂-C*(OH)-CH**(R¹)-S(O)ₙ-X-R³, with 2,4-difluorophenyl group at C*]

| Compound No. | R¹ | n | X | R³ | Configuration C* | C** |
|---|---|---|---|---|---|---|
| 6 | H | 2 | —CH₂CH₂— | imidazol-1-yl | RS | — |
| 7 | H | 0 | —(CH₂)₂S(CH₂)₂— | imidazol-1-yl | RS | — |
| 8 | H | 0 | —CH₂CH₂— | 4-pyridyl | RS | — |
| 9 | H | 0 | —CH(CH₃)— | 4-pyridyl (diastereomeric mixture) | RS | — |
| 10 | H | 0 | —CH(CH₃)— | 4-pyridyl (diastereomer A) | RS | — |
| 11 | H | 0 | —CH(CH₃)— | 4-pyridyl (diastereomer B) | RS | — |
| 12 | CH₃ | 0 | — | 2-(cyclopenta-fused thiazolyl) | RS | RS |
| 13 | CH₃ | 0 | —CH₂CH₂— | 1,2,4-triazol-1-yl | RS | RS |
| 14 | CH₃ | 2 | —CH₂CH₂— | 1,2,4-triazol-1-yl | RS | RS |

TABLE 1-continued
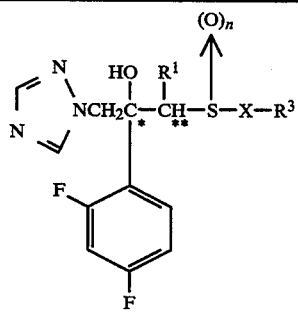
| Compound No. | R¹ | n | X | R³ | Configuration C* | C** |
|---|---|---|---|---|---|---|
| 15 | CH₃ | 0 | —CH₂— | 4-pyridyl | RS | RS |
| 16 | CH₃ | 0 | —CH₂— | 1-methylimidazol-2-yl | RS | RS |
| 17 | H | 0 | —CH₂CH₂SCH₂— | 1-methylimidazol-2-yl | RS | — |
| 18 | H | 0 | —CH₂CH₂S— | 1-methylimidazol-2-yl | RS | — |
| 19 | H | 0 | —CH₂CH₂SCH₂— | 4-pyridyl | RS | — |
| 20 | H | 0 | —CH₂CH₂S— | 1-methyltetrazol-5-yl | RS | — |
| 21 | H | 0 | —(CH₂)₂S(CH₂)₂— | 1H-1,2,4-triazol-1-yl | RS | — |
| 22 | CH₃ | 0 | —(CH₂)₂S(CH₂)₂— | 1H-1,2,4-triazol-1-yl | RS | RS |
| 23 | CH₃ | 0 | —(CH₂)₂S(CH₂)₂— | 1H-imidazol-1-yl | RS | RS |

TABLE 1-continued

[Structure: triazole-NCH₂-C*(OH)(2,4-difluorophenyl)-C**H(R¹)-S(O)ₙ-X-R³]

| Compound No. | R¹ | n | X | R³ | Configuration C* | C** |
|---|---|---|---|---|---|---|
| 24 | H | 0 | —CH₂CH₂S— | 4-pyridyl | RS | — |
| 25 | CH₃ | 0 | —CH₂— | 2-(6,7-dihydro-5H-cyclopenta[d]thiazolyl) | RS | RS |
| 26 | CH₃ | 0 | — | 5-methyl-1,3,4-thiadiazol-2-yl | RS | RS |
| 27 | CH₃ | 0 | —CH₂— | imidazo[1,2-a]pyridin-2-yl | RS | RS |
| 28 | CH₃ | 0 | —CH₂— | 1-methyl-1H-imidazol-4-yl | RS | RS |
| 29 | CH₃ | 0 | —CH₂— | 1-methyl-1H-imidazol-5-yl | RS | RS |
| 30 | CH₃ | 0 | —CH₂— | 1-(2,2,3,3-tetrafluoropropyl)imidazol-2-yl | RS | RS |
| 31 | CH₃ | 0 | —CH₂— | 1-methyl-1H-1,2,4-triazol-5-yl | RS | RS |
| 32 | CH₃ | 0 | —CH₂— | 2-methyl-2H-1,2,3-triazol-4-yl | RS | RS |
| 33 | CH₃ | 0 | —CH₂— | 1-methyl-1H-1,2,3-triazol-5-yl | RS | RS |

TABLE 1-continued
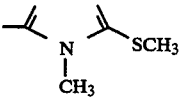
| Compound No. | R¹ | n | X | R³ | Configuration C* | C** |
|---|---|---|---|---|---|---|
| 34 | $CH_3$ | 0 | $-CH_2-$ | 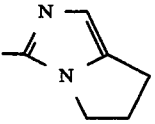 | RS | RS |
| 35 | $CH_3$ | 0 | $-CH_2-$ | 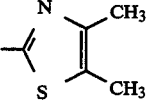 | RS | RS |
| 36 | $CH_3$ | 0 | $-CH_2-$ | 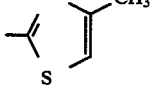 | RS | RS |
| 37 | $CH_3$ | 0 | $-CH_2-$ | 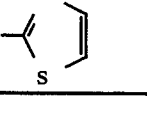 | RS | RS |
| 38 | $CH_3$ | 0 | $-CH_2-$ | 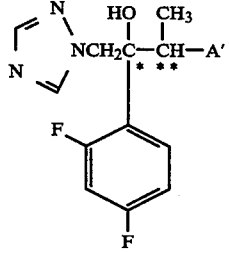 | RS | RS |
TABLE 2
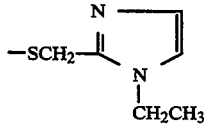
| Compound No. | Configuration C* | C** | R⁴ |
|---|---|---|---|
| 39 | RS | RS | $-H$ |
| 40 | RS | RS | $-COCH_3$ |
TABLE 3
| Compound No. | Configuration C* | Configuration C** | A' |
|---|---|---|---|
| 42 | S | S | $-SH$ |
| 43 | R | R | $-SH$ |
| 44 | S | S | $-SCOCH_3$ |
| 45 | R | R | $-SCOCH_3$ |
| 46 | RS | RS |  |

TABLE 3-continued

| # | | | Structure |
|---|---|---|---|
| 47 | RS | RS | —SCH₂-(N-imidazoline, N-CH(CH₃)₂) |
| 48 | RS | RS | —SCH₂-(N-imidazoline, N-CH₂CFH₂) |
| 49 | RS | RS | —SCH₂-(N-imidazoline, N-CH₂CF₃) |
| 50 | RS | RS | —S(CH₂)₂-(N-imidazoline, N-CH₃) |
| 51 | RS | RS | —SCH₂-(N-imidazoline, N-CH₂cyclopropyl) |
| 52 | RS | RS | —SCH₂-(2-methyl-thiazoline, 5-yl) |
| 53 | RS | RS | —SCH₂-(2-methyl-thiazoline, 4-yl) |
| 54 | RS | RS | —SCH₂-(N-imidazoline, N-CH₂CF₂H) |
| 55 | RS | RS | —SCH₂-(N-imidazoline, N-cyclopropyl) |
| 56 | RS | RS | —SCH₂-(4-methyl-1,3-dioxol-2-one-5-yl) |
| 57 | RS | RS | —SCH₂-(imidazo-pyrazine) |
| 59 | RS | RS | —SCH₂-(N-imidazoline, N-CH(CH₂F)₂) |
| 60 | RS | SR | —SH |
| 61 | RS | SR | —SC(O)CH₃ |
| 62 | R | R | —SC(O)CH(CH₃)₂ |
| 64 | R | R | —SCH₂CH₂-(N-benzimidazole) |
| 65 | R | R | —SCH₂CH₂-(N-1,2,4-triazole) |
| 66 | R | R | —S(O)₂CH₂CH₂-(N-1,2,4-triazole) |
| 67 | R | R | —S(O)CH₂CH₂-(N-1,2,4-triazole) |
| 68 | R | R | —SCH₂CH₂-(N-imidazole) |
| 69 | R | R | —S(O)₂CH₂CH₂-(N-imidazole) |
| 70 | R | R | —S(CH₂)₂S(CH₂)₂-(N-imidazole) |
| 71 | R | R | —SCH₂CH₂-(4-pyridyl) |
| 72 | R | R | —S—CH(CH₃)-(4-pyridyl) (diastereomer A) |

TABLE 3-continued

| # | | | Structure |
|---|---|---|---|
| 73 | R | R | —S—CH(CH3)—(4-pyridyl) (diastereomer B) |
| 74 | R | R | —S—(2-(5,6-dihydro-4H-cyclopenta[d]thiazolyl)) |
| 75 | R | R | —SCH2CH2CH2—N(1,2,4-triazol-1-yl) |
| 76 | R | R | —SCH2CH2CH2CH2—N(1,2,4-triazol-1-yl) |
| 77 | R | R | —SCH2—(4-pyridyl) |
| 78 | R | R | —SCH2—(1-methyl-imidazol-2-yl) |
| 79 | R | R | —SCH2CH2SCH2—(1-methyl-imidazol-2-yl) |
| 80 | R | R | —SCH2CH2S—(1-methyl-imidazol-2-yl) |
| 81 | R | R | —SCH2CH2CH2—(4-pyridyl) |
| 82 | R | R | —SCH2CH2S—(1-methyl-tetrazol-5-yl) |
| 83 | R | R | —S(CH2)2S(CH2)2—N(1,2,4-triazol-1-yl) |
| 84 | R | R | —S(CH2)2S(O)2(CH2)2—N(1,2,4-triazol-1-yl) |
| 85 | R | R | —S(CH2)2S(O)2(CH2)2—N(imidazol-1-yl) |
| 86 | R | R | —SCH2CH2S—(4-pyridyl) |
| 87 | R | R | —SCH2—(2-(5,6-dihydro-4H-cyclopenta[d]thiazolyl)) |
| 88 | R | R | —S—(5-methyl-1,3,4-thiadiazol-2-yl) |
| 89 | R | R | —SCH2—(imidazo[1,2-a]pyridin-2-yl) |
| 90 | R | R | —SCH2—(1-methyl-imidazol-5-yl) |
| 91 | R | R | —SCH2—(1-methyl-imidazol-5-yl) |
| 92 | R | R | —SCH2—(1-(CH2CF2CF2H)-imidazol-5-yl) |
| 93 | R | R | —SCH2—(1-methyl-1,2,4-triazol-5-yl) |
| 94 | R | R | —SCH2—(2-methyl-2H-1,2,3-triazol-4-yl) |
| 95 | R | R | —SCH2—(1-methyl-1H-1,2,3-triazol-5-yl) |

TABLE 3-continued

| | | | |
|---|---|---|---|
| 96 | R | R | —SCH₂-[3-(methylthio)-1-methyl-1H-1,2,4-triazol-5-yl] |
| 97 | R | R | —SCH₂-[6,7-dihydro-5H-pyrrolo[1,2-a]imidazol-2-yl] |
| 98 | R | R | —SCH₂-[4,5-dimethylthiazol-2-yl] |
| 99 | R | R | —SCH₂-[4-methylthiazol-2-yl] |
| 100 | R | R | —SCH₂-[thiazol-2-yl] |
| 101 | R | R | —SCH₂-[1-ethyl-1H-imidazol-2-yl] |
| 102 | R | R | —SCH₂-[1-isopropyl-1H-imidazol-2-yl] |
| 103 | R | R | —SCH₂-[1-(2,2-difluoroethyl)-1H-imidazol-2-yl] |
| 104 | R | R | —SCH₂-[1-(2,2,2-trifluoroethyl)-1H-imidazol-2-yl] |
| 105 | R | R | —S(CH₂)₂-[1-methyl-1H-imidazol-2-yl] |
| 106 | R | R | —SCH₂-[1-(cyclopropylmethyl)-1H-imidazol-2-yl] |
| 107 | R | R | —SCH₂-[2-methylthiazol-4-yl] |
| 108 | R | R | —SCH₂-[2-methylthiazol-5-yl] |
| 109 | R | R | —SCH₂-[1-(2,2-difluoroethyl)-1H-imidazol-2-yl] |
| 110 | R | R | —SCH₂-[1-cyclopropyl-1H-imidazol-2-yl] |
| 111 | R | R | —SCH₂-[4-methyl-1,3-dioxol-2-one-5-yl] |
| 112 | R | R | —SCH₂-[imidazo[1,2-a]pyrazin-2-yl] |
| 113 | R | R | —SCH₂-[1-(1,3-difluoroprop-2-yl)-1H-imidazol-2-yl] |
| 114 | R | R | —SCH₂-[4-cyclopropyl-4H-1,2,4-triazol-3-yl] |
| 115 | | | triazole-CH(CH₃)-C(OH)(2,4-difluorophenyl)-CH₂SH (diastereomer A) |

TABLE 3-continued

| | | | |
|---|---|---|---|
| 116 | 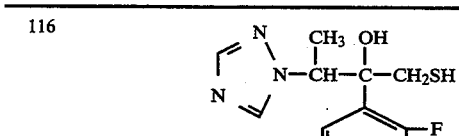 (diastereomer B) | 122 | R R 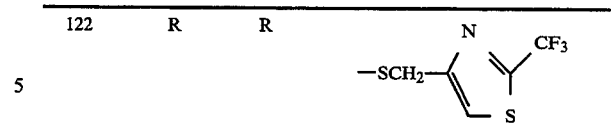 |
| 117 | 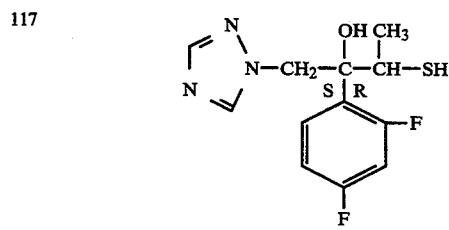 | 123 | R R 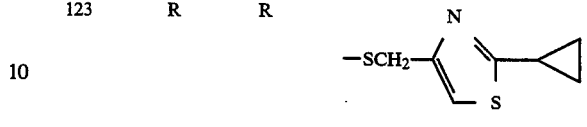 |
| | | 124 | R R 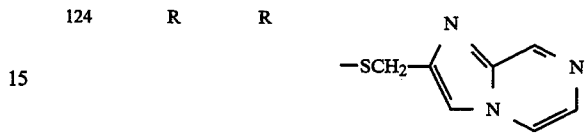 |
| 118 | 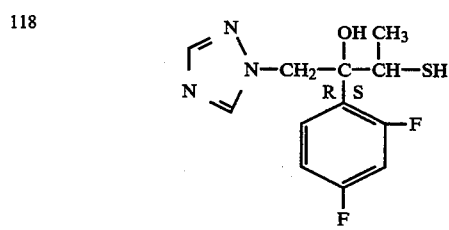 | 125 | R R 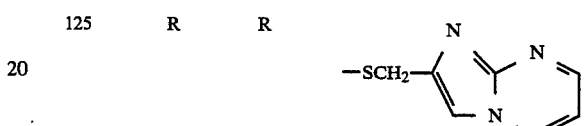 |
| | | 126 | R R 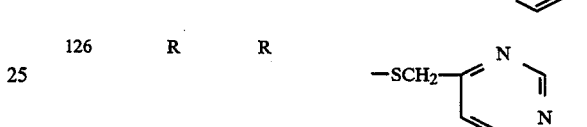 |
| 119 | 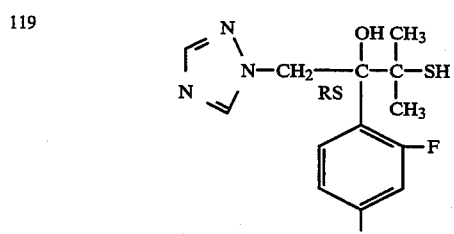 | 127 | R R 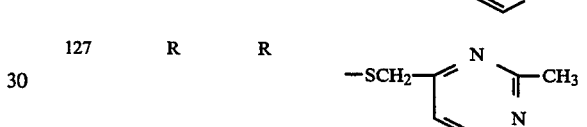 |
| | | 128 | R R 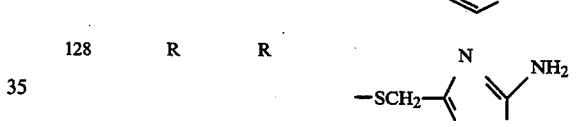 |
| 120 | 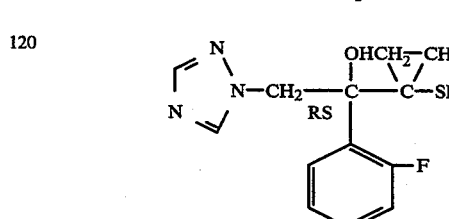 | 129 | R R 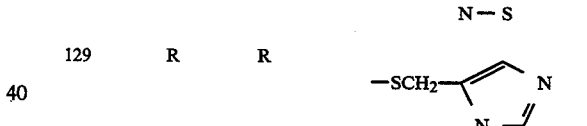 |
| | | 130 | R R  |
| | | 131 | R R  |

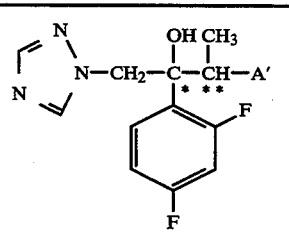

| Compound No. | Configuration C* | Configuration C** | A' |
|---|---|---|---|
| 121 | R | R | 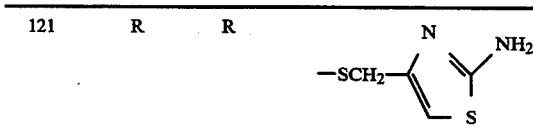 |
| 122 | | | (see above) |

Each of the compounds (I) of this invention has one or more asymmetric carbon atoms, and stereoisomers of R configuration and of S configuration and the mixture thereof are all included in this invention. The compounds having a methyl group as $R^1$ and a hydrogen atom as $R^2$ of which the absolute configuration is the R configuration are desirable.

The compounds (I) are obtained also in the form of salts, and specifically pharmacologically acceptable salts. The said salts include inorganic acid salts such as hydrochlorides, hydrobromides, sulfates, nitrates, and phosphates, and organic acid salts such as acetates, tartrates, citrates, fumarates, maleates, toluenesulfonates, and methanesulfonates.

When n is 0 in the formula (I') of this invention, such compounds can be produced by, for example, the reaction of a compound represented by the formula:

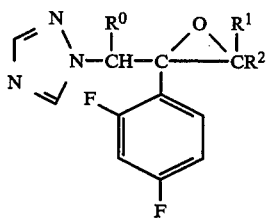
(II)

wherein the symbols are the same as defined above, and a compound represented by the general formula:

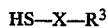
(III)

wherein the symbols are the same as defined above. The reaction is usually allowed to proceed in the presence of water or an organic solvent (e.g. acetonitrile, dimethylformamide, dimethylsulfoxide, tetrahydrofuran, methyl alcohol, ethyl alcohol, which are used separately or in combination) or without any solvent, at −20° to +150° C. A base such as potassium carbonate, potassium hydroxide, sodium hydroxide, sodium hydride, sodium methylate, sodium ethylate, or tetrabutylammonium fluoride may be added to the reaction system to accelerate the reaction.

When n is 0 in the formula (I') of this invention, such compounds can also be produced by, for example, the reaction of a compound represented by the formula:

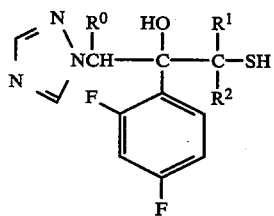
(V)

wherein the symbols are the same as defined above, and a compound represented by the general formula:

(VI)

wherein X and $R^3$ are the same as defined above, and W is a halogen atom or a group represented by the formula: $R^{3'}$—$SO_2$—O— (wherein $R^{3'}$ is a lower($C_{1-4}$) alkyl, trifluoromethyl, phenyl, or p-tolyl). The reaction is usually allowed to proceed in the presence of water or an organic solvent (e.g. acetonitrile, dioxane, dimethylformamide, dimethylsulfoxide, tetrahydrofuran, methyl alcohol, ethyl alcohol, which are used separately or in combination) or without any solvent, at −20° to +150° C. A base such as potassium carbonate, potassium hydroxide, sodium hydroxide, sodium hydride, sodium methylate, sodium ethylate, or tetrabutylammonium fluoride may be added to the reaction system to accelerate the reaction.

When $R^4$ is an alkanoyl group in the formula (I'') of this invention, such compounds can be produced by, for example, the reaction of a compound represented by the formula:

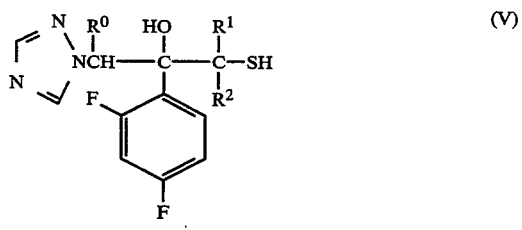
(V)

wherein the symbols are the same as defined above, and a compound represented by the formula:

(VII)

wherein $R^{4'}$ is an alkanoyl group and W' is a halogen atom or —O—$R^{4''}$ (wherein $R^{4''}$ is an acyl group).

The reaction is usually allowed to proceed in the presence of water or an organic solvent (e.g. methylene chloride, chloroform, ethyl acetate, benzene, dioxane, tetrahydrofuran, which are used separately or in combination), at −20° to 100° C. An inorganic base such as potassium carbonate, sodium hydrogencarbonate, or sodium hydroxide, or an organic base such as triethylamine, pyridine, or picoline may be added to the reaction system to accelerate the reaction.

When n is 1 or 2 in the formula (I') of this invention, such compounds can be produced by, for example, oxidation of a compound represented by the formula:

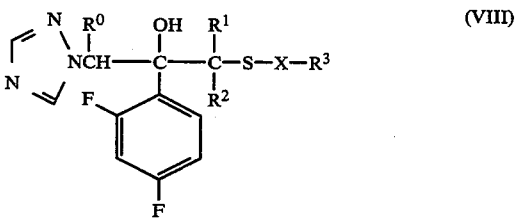
(VIII)

wherein the symbols are the same as defined above.

The oxidation is usually allowed to proceed in the presence of water or an organic solvent (e.g. methylene chloride, chloroform, isopropyl alcohol, benzene, acetic acid, which are used separately or in combination) at −20° to 50° C. with an oxidant (e.g. m-chloroperbenzoic acid, peracetic acid, hydrogen peroxide, benzoyl peroxide). The amount of the oxidant equivalent to the compound (VIII) can be adjusted appropriately, so that the compound in which n is 1 and that in which n is 2 in the formula (I') may be obtained separately or as a mixture. Also the reaction temperature and reaction time can be adjusted so that the compound of which n is 1 and that of which n is 2 in the formula (I') may be obtained separately or as a mixture. m-Chloroperbenzoic acid is particularly desirable as the oxidant for this oxidation.

The compound (I'') of the invention wherein $R^4$ is hydrogen may also be produced, for example, by subjecting a compound of the formula

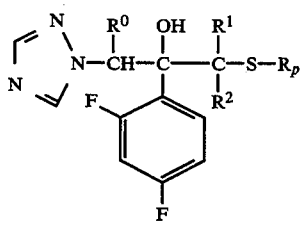

wherein $R^0$, $R^1$ and $R^2$ have the meanings respectively defined hereinbefore; $R_p$ is benzyl, p-methoxybenzyl, p-methylbenzyl or trityl to deprotection reaction. This deprotection reaction may be conducted, for example, by the technique which comprises permitting an acid (e.g. hydrogen fluoride, trifluoroacetic acid, trifluoromethanesulfonic acid, etc.) to act on the substrate compound (XXIX) in the presence or absence of anisole or thioanisole, the technique which comprises permitting sodium metal to act on XXIX in liquid ammonia, or the technique which comprises treating the substrate compound with a heavy metal (e.g. silver nitrate, mercury acetate, mercury trifluoroacetate, etc.) and, then, reacting it with a mercapto compound (e.g. hydrogen sulfide, β-mercaptoethanol, etc.). This deprotection reaction can generally be carried out in the presence or absence of an organic solvent (e.g. acetic acid, methylene chloride, chloroform, trifluoroacetic acid, etc.) at a temperature between about −10° C. to about 60° C.

The resulting compound (I) can be isolated from the reaction mixture by the conventional purification procedure such as extraction, concentration, neutralization, filtration, recrystallization, column chromatography and thin-layer chromatography.

Compound (I) may occur as at least two stereoisomers. These isomers as well as mixtures thereof are subsumed in the concept of the invention and, if desired, can be produced individually. For example, by subjecting a specific isomer of starting compound (II), (III), (V), (VI), (VII), (VIII) or (XXIX) to the corresponding reaction described hereinbefore, the corresponding isomer of compound (I) can be selectively produced. On the other hand, when the reaction product is a mixture of two or more isomers, it can be fractionated into respective isomers by the conventional resolution or fractionation techniques such as the formation of a salt with an optically active acid (e.g. camphorsulfonic acid, tartaric acid, etc.), several types of chromatography, fractional recrystallization and so on.

The physiologically acceptable salt of compound (I) can be produced by adding one of the aforementioned inorganic acids and organic acids.

Among the synthetic intermediate (II) to be used in the present invention, compound (IX) wherein $R^0$ and $R^2$ are hydrogen can be produced by the process illustrated in the following reaction schema.

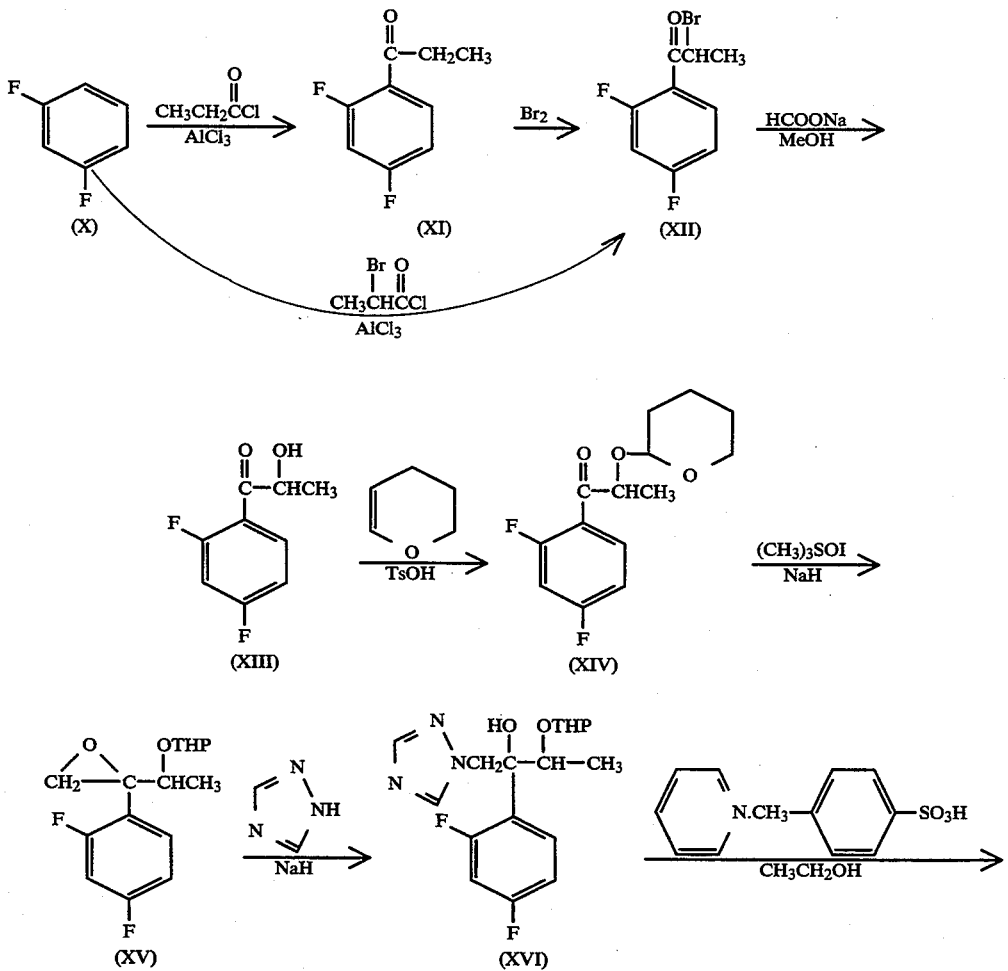

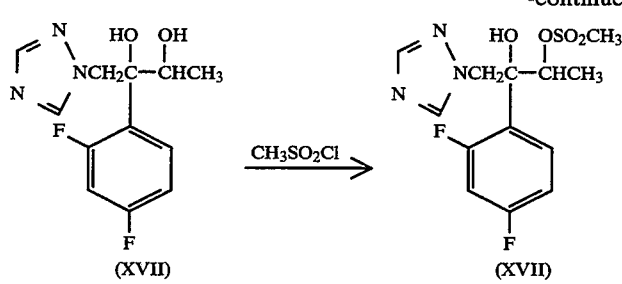
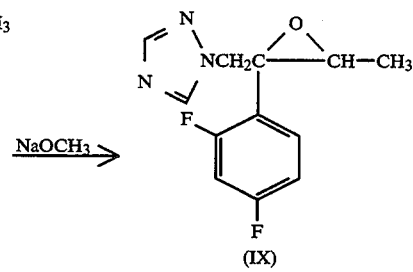

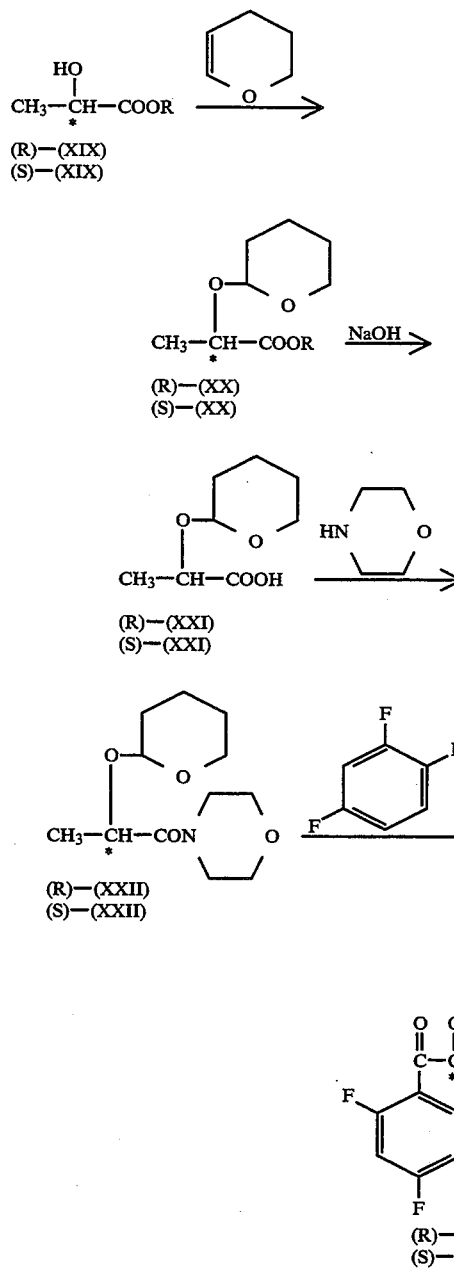

wherein the substituent R is a $C_{1-4}$ alkyl group.

The production process for compound (IX) is described in detail below. Thus, 2,4-difluorobenzene (X) is subjected to a Friedel-Crafts reaction with propionyl chloride to give (XI) which is then treated with bromine to give the bromide (XII). This compound (XII) can also be prepared by subjecting compound (X) and 2-bromopropionyl chloride to a Friedel-Crafts reaction. The reaction (XII)-(XIII) is a hydrolysis reaction, which can be easily carried out in the presence of sodium formate in methanol. Subjecting compound (XIII) to the usual tetrahydropyranylation reaction gives compound (XIV). When this compound (XIV) is reacted with trimethylsulfoxonium iodide in the presence of sodium hydride, a compound (XV), wherein THP is 2-(2H)-3,4,5,6-tetrahydropyranyl, is obtained. The reaction (XV)→(XVI) is an epoxy ring-opening reaction by the triazole sodium salt formed from triazole and sodium hydride and can be easily accomplished in dimethylformamide at 60°-90° C. When pyridinium p-toluenesulfonate is permitted to act on compound (XVI) in ethanol, the deprotection reaction proceeds, giving rise to compound (XVII). This compound (XVII) is reacted with methanesulfonyl chloride to give compound (XVIII), which is then treated with a base (e.g. sodium methoxide) to give compound (IX).

In this method of synthesis, (XVII), (XVIII) and (IX) are obtained as mixtures of two diastereomers. If desired, (XVII), (XVIII) and (IX) may each be fractionated into the component diastereomers by fractional recrystallization, chromatography or the like or the precusor compounds (XV) and (XVI) may each be fractionated by fractional recrystallization, chromatography or the like before subjecting to the corresponding reaction to ultimately give diastereomers of (XVII), (XVIII) and (IX). Moreover, a diastereomer of (XVIII) or (IX) may be produced by using the corresponding diastereomer of (XVII) or (XVIII).

It is also possible to use an optically active (R)-lactic acid ester [(R)-(XIX)] or (S)-lactic acid ester [(S)-(XIX)] as the starting material to synthesize the corresponding optically active (XIV) [(R)-(XIV) or (S)-(XIV)] according to the reaction schema illustrated below and, then, reacting the same according to the reaction schema given hereinbefore, followed by separation of diastereomers, if desired, to give optionally active (XVII) [(2R, 3R)-(XVII), (2R, 3S)-(XVII), (2S, 3S)-(XVII), (2S, 3R)-(XVII)], (XVIII) [(2R, 3R)-(XVIII), (2R, 3S)-(XVIII), (2S, 3S)-(XVIII), (2S, 3R)-(XVIII)] and (IX) [(2R, 3R)-(IX), (2R, 3S)-(IX), (2S, 3S)-(IX), (2S, 3R)-(IX)].

Reacting the (R)-lactic acid ester (R)-(XIX) with (2H)-3,4-dihydropyran in the presence of p-toluenesulfonic acid gives compound (R)-(XX). This reaction is conducted in a solvent, such as methylene chloride, chloroform, etc., generally in the temperature range of about −10° to about 30° C. The reaction (R)-(XX)-(R)-(XXI) is an ordinary hydrolysis reaction, which proceeds readily in the presence of a base (e.g. sodium hydroxide, potassium hydroxide, etc.) in water or an organic solvent (e.g. methanol, ethanol, etc.), or a mixture thereof at a temperature in the range of about 0° to about 40° C. The condensation reaction between the resulting compound (R)-(XXI) and morpholine can be advantageously carried out generally in the presence of a known dehydrative condensing agent to give compound (R)-(XXII). The dehydrative condensing agent to be used in this reaction includes, for example, dicyclohexylcarbodiimide, carbonyldiimidazole, diethyl cyanophosphate and so on. The solvent may for example be tetrahydrofuran, dioxane or acetonitrile. This reaction is generally carried out at a temperature of −10° C. to 40° C. The reaction (R)-(XXII)-(R)-(XIV) is a Grignard reaction and can be carried out by reacting compound (R)-(XXII) with 2,4-difluorophenylmagnesium bromide prepared from 2,4-difluorobromobenzene and magnesium metal, in an organic solvent (e.g. tetrahydrofuran, ethyl ether, etc.) at a temperature of about −10° to about 40° C. In lieu of the morpholino group, the amide compound (R)-(XXII) used in this Grignard reaction may have a different cyclic amino group (e.g. 1-pyrrolidinyl, piperidino, etc.) or a secondary amino group (e.g. dimethylamino, diethylamino, dibutylamino, etc.), and these amides can be synthesized by condensation of the corresponding amines with (R)-(XXI). Furthermore, reacting (S)-lactic acid ester (S)-(XIX) in the same manner as above [(S)-(XIX)→(S)-(XX)→(S)-(XXI)→(S)-(XXII)→(S)-(XIV)] gives compound (S)-(XIV).

In the synthesis of the optically active compound according to the invention, the optically active intermediate (XXII) can also be synthesized in accordance with the following reaction schema.

advantageously conducted by heating compound (R)-(XIX) and morpholine in the presence or absence of a solvent (e.g. benzene, toluene, etc.) at a temperature of 60°–100° C. The reaction of compound (R)-(XXIII)-compound (R)-(XXII) can be conducted in the same manner as the reaction of (R)-(XIX)-(R)-(XX). In the above reaction schema, the use of a cyclic amine other than morpholine (e.g. pyrrolidine, piperidine, etc.) or a secondary amine (e.g. dimethylamine, diethylamine, dibutylamine, etc.) in lieu of morpholine under otherwise the same conditions gives a compound wherein the morpholino group has been replaced by the corresponding cyclic amino group or secondary amino group, and such compounds can be used, just as (R)-(XXII), in the Grignard reaction with 2,4-difluorophenylmagnesium bromide. Furthermore, subjecting (S)-lactic acid ester (S)-(XIX) to the same reaction as above gives compound (S)-(XXII) in the manner of [(S)-(XIX)→(S)-(XXIII)→(S)-(XXII)].

The optically active intermediate (R)-(XIV) can also be synthesized using (R)-lactic acid derivative (R)-(XXIV) as the starting material in accordance with the following reaction schema.

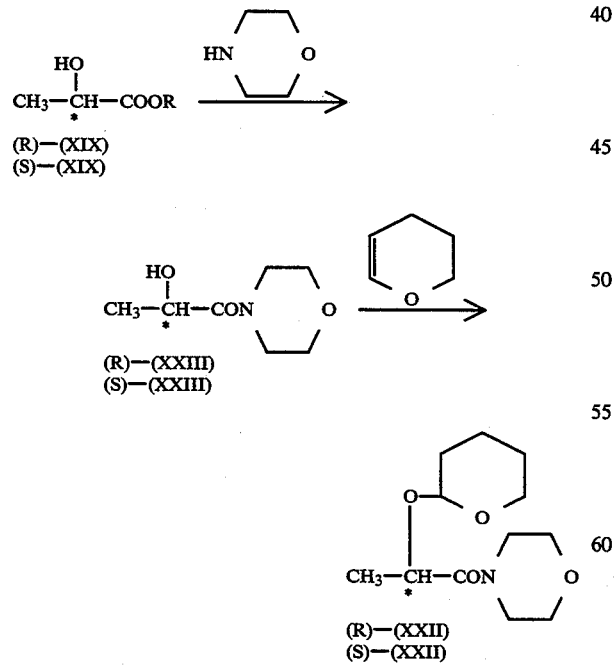

wherein the substituent R has the same meaning as defined hereinbefore. The conversion reaction of (R)-lactic acid ester (R)-(XIX) to amide (R)-(XXIII) can be

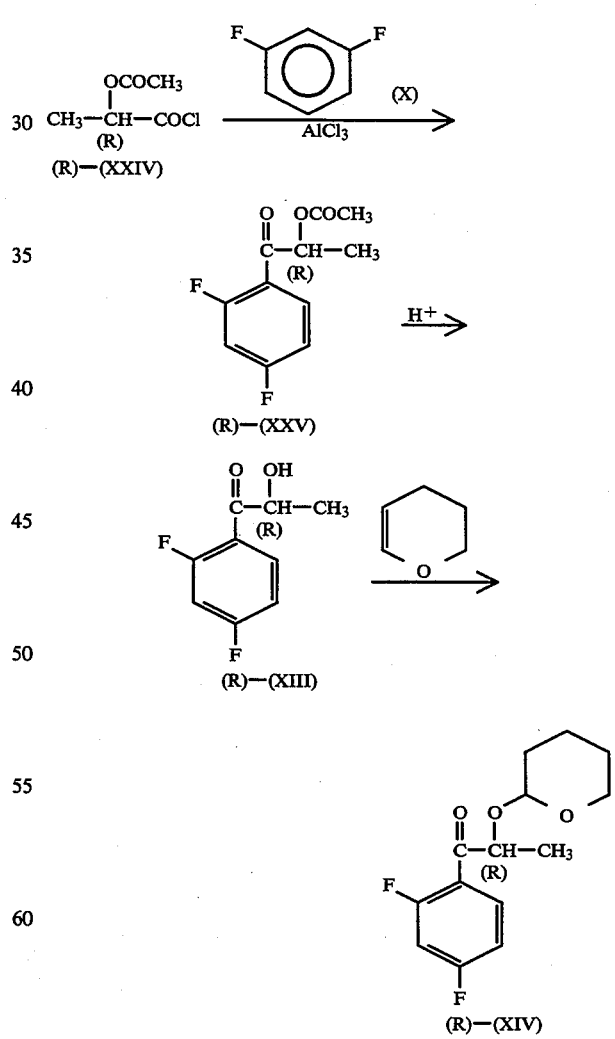

The use of the corresponding diastereomers of (XVII), (XVIII) and (IX) or the optically active forms of (XVII), (XVIII) and (IX) obtained in the above manner as intermediates give the corresponding diastereomer of compound (I) or the optically active form of compound (I) as the case may be.

Referring to the synthetic intermediate (II) of the invention, compound (XXVI) wherein $R^0$ is methyl and $R^1$ and $R^2$ are hydrogen can be produced by the process illustrated in the following reaction schema, for instance.

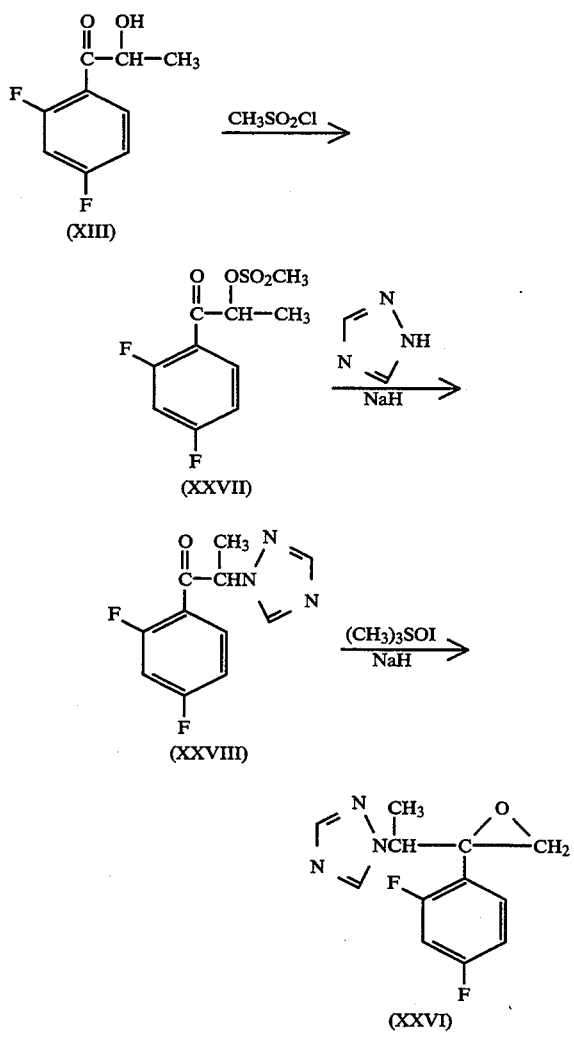

The synthetic intermediates (XXIX) of the invention can for example be produced by the process illustrated below.

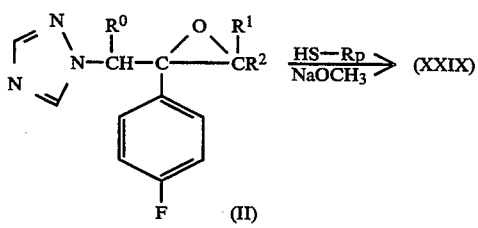

wherein all the symbols have the meanings respectively defined hereinbefore.

Among the synthetic intermediates (XXIX) of the invention, compound (XXX) wherein $R^0$ is hydrogen and $R^1$ and $R^2$ jointly represent an ethylene group can for example be produced by the process illustrated in the following reaction formula.

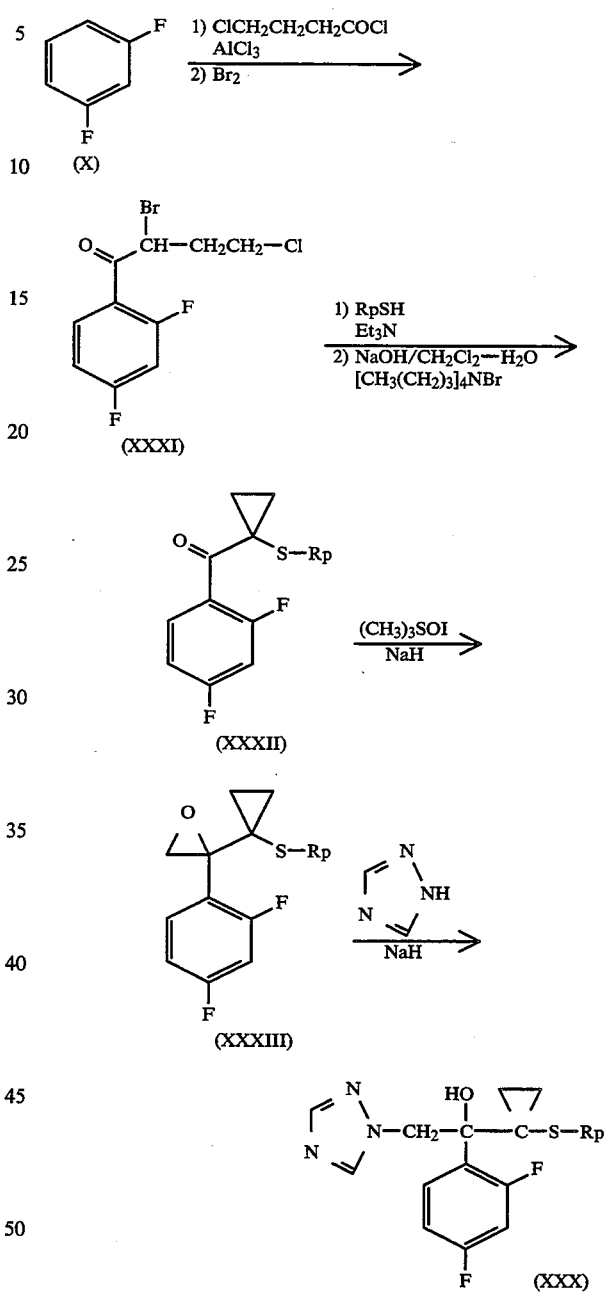

wherein all the symbols have the meanings defined hereinbefore.

When $R^4$ is a hydrogen atom in the formula (I″) of this invention, such compounds can be produced by, for example, the reaction of a compound represented by the formula:

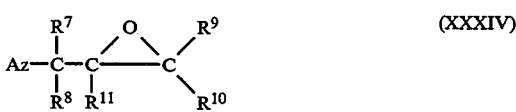

wherein $R^7$, $R^8$, $R^9$, $R^{10}$ and $R^{11}$ are the same or different, being respectively a hydrogen atom or a hydrocarbon residue which may be substituted, and Az is triazolyl or imidazolyl, and a compound represented by the formula:

 (IV)

wherein at least one of Z and Y is a cyano group or a carboxyl group which may be esterified or amidated, and the other is a hydrogen atom, a lower alkyl group, or an amino group which may be acylated.

The reaction can be performed in one process, the reagents used are inexpensive and can be handled easily, and the desired compounds represented by the general formula (I″) can be produced in a large amount; thus the method is suitable for industrial production.

The reaction between a compound represented by the general formula (XXXIV) and a compound represented by the general formula (IV) is desirably performed in the presence of a base; the base may be inorganic or organic, being exemplified by sodium hydroxide, potassium hydroxide, sodium carbonate, potassium carbonate, sodium hydrogencarbonate, potassium hydrogencarbonate, sodium methylate, sodium ethylate, potassium methylate, potassium ethylate, potassium tert-butylate, sodium hydride, potassium hydride, butyllithium, lithium diisopropylamide, triethylamine, N-methylmorpholine, dimethylaminopyridine, lutidine, tetrabutylammonium fluoride, tetrabutylammonium hydroxide, N-benzyltrimethylammonium hydroxide, 1,8-diazabicyclo[5,4,0]unde-7-cene, 1,5-diazabicyclo[4,3,0]non-5-ene, and 1,4-diazabicyclo[2,2,2]octane, among which sodium hydride and sodium methylate are desirable.

Triazoles represented by Az in the formulas (XXXIV) described above include 1,2,4-triazole.

The hydrocarbon residues represented by $R^7$, $R^8$, $R^9$, $R^{10}$, and $R^{11}$ in the formulas (XXXIV) described above which may be substituted include alkyl, cycloalkyl, alkenyl, and aryl groups.

The said alkyl groups include those having 1 to 12 carbon atoms each, such as methyl, ethyl, propyl, butyl, heptyl, octyl, nonyl, decyl, and dodecyl, and may be straight chain or branched.

The said cycloalkyl groups include those having 3 to 7 carbon atoms each, such as cyclopropyl, cyclobutyl, cyclopentyl, cyclohexyl, and cycloheptyl.

The said alkenyl groups include those having 2 to 6 carbon atoms each, such as allyl, vinyl, 1,3-butadienyl, isoprenyl, and 2,4-pentadienyl.

The said aryl groups include phenyl, naphthyl, biphenyl, anthryl, and indenyl.

The substituents which the above-mentioned hydrocarbon residues may have include hydroxyl group, carboxyl groups which may be esterified (e.g. carboxy, ethoxycarbonyl, methoxycarbonyl, butoxycarbonyl), amino groups, acylamino groups (e.g. acetylamino, propionylamino, butyrylamino), alkylamino (e.g. methylamino, dimethylamino, diethylamino, dibutylamino), alkoxy groups (e.g. methoxy, ethoxy, butoxy), halogen atoms (e.g. fluoro, chloro, bromo), oxo, thio, mercapto, alkylthio (e.g. methylthio, ethylthio, butylthio), and cyano, and in addition, the alkyl, cycloalkyl, alkenyl, and aryl groups described above.

The above-mentioned hydrocarbon residues may have 1 to 3 substituents which may be the same or different.

The lower($C_{1-4}$) alkyl groups represented by X or Y in the formula (IV) described above include methyl, ethyl, propyl, butyl, isopropyl, and tert-butyl. The amino groups represented by Z or Y which may be acylated include acetylamino, benzoylamino, tosylamino, and mesylamino.

The carboxy groups represented by Z or Y in the formula (IV) which may be esterified or amidated include carboxy, methoxycarbonyl, ethoxycarbonyl, benzyloxycarbonyl, butoxycarbonyl, carbamoyl, dimethylaminocarbonyl, diethylaminocarbonyl, morpholinocarbonyl, piperidinocarbonyl, and 1-pyrrolidinylcarbonyl.

Each of the mercapto compounds represented by the general formula (V) have one or more asymmetric carbon atoms and thus two or more stereoisomers. The present invention relates to the method for production of all of the stereoisomers.

The method for production of this invention can be put into practice for example as follows:

To an appropriate solvent (e.g. methanol, ethanol, isopropyl alcohol, dimethylformamide, dimethylsulfoxide, acetone, toluene, benzene, ethyl acetate, dioxane, tetrahydrofuran, and water, which may be used separately or in combination) is added a compound represented by the general formula (XXXIV), and then one or more equivalents, desirably 2 to 10 equivalents, of an above-mentioned base relative to the amount of the compound (XXXIV). Then one or more equivalents, desirably 2 to 20 equivalents, of a compound represented by the general formula (IV) relative to the amount of the compound (XXXIV) is added. The resultant mixture is kept at $-10°$ to $100°$ C. (desirably $0°$ to $80°$ C.) so that the reaction may proceed. After completion of the reaction, a compound represented by the general formula (IX) is obtained by a per se known method for isolation (concentration, neutralization, extraction, re-crystallization, filtration, various chromatographic methods).

The most desirable starting compound (IV) used in the method for production of this invention is the compound having methoxycarbonyl as Z and a hydrogen atom as Y (3-mercaptopropionic acid methyl ester).

The desirable starting compounds (XXXIV) are those having 1,2,4-triazolyl as Az, hydrogen atoms or lower alkyl groups as $R^7$, $R^8$, $R^9$, and $R^{10}$, and a substituted aryl group as $R^{11}$, among which the compound having hydrogen atoms as $R^7$, $R^8$, and $R^9$, methyl as $R^{10}$, and 2,4-difluorophenyl as $R^{11}$ is especially desirable.

Among the starting compounds (XXXIV) the compounds (IX) having 1,2,4-triazolyl as Az, hydrogen atoms as $R^7$, $R^8$, and $R^9$, methyl as $R^{10}$, and 2,4-difluorophenyl as $R^{11}$ can be synthesized according to, for example, above-mentioned reaction schemes.

EFFECTS

The antifungal activities of the compounds (I) were evaluated by the following method: a sheet of filter paper disc (manufactured by Toyo Seisakusho, 8 mm in diameter) soaked in a 1000 μg/ml solution of a compound (I) in methanol was placed on an agar plate, which was incubated at $28°$ C. for 2 days, and the diameter of the growth inhibition zone around the filter paper disc was measured. The following culture media were used:

A: yeast nitrogen base agar medium
B: yeast nitrogen base agar medium (pH 7.0)
C: Sabouraud agar medium The antifungal spectra of the compounds (I) are shown in Table 4.

TABLE 4

Antifungal spectra

| Test fungi | Media | Inhibition zone diameter (mm) Compound 12 | Compound 15 |
|---|---|---|---|
| *Candida albicans* IFO 0583 | A | 42 | 34 |
| *Candida albicans* (Ca—O) IFO 0583 | A | 41 | 32 |
| *Aspergillus niger* IFO 4066 | A | 20 | 29 |
| *Aspergillus fumigatus* IFO 6344 | A | 38 | 30 |
| *Penicillium chrysogenum* IFO 4626 | A | 15 | 23 |
| *Trichophyton rubrum* IFO 6467 | C | 35 | 60 |
| *Trichophyton mentagrophytes* IFO 7522 | C | 32 | 50 |
| *Microsporum gypseum* IFO 6075 | C | 35 | 45 |

Tables 5 and 6 show the antifungal activities of the compounds (I) against *Candida albicans*. Table 5

TABLE 5

| Compound No. | Inhibition zone diameter (mm) *Candida albicans* (IFO 0538) (A medium, 28° C., 2 days incubation) |
|---|---|
| 2 | 18 |
| 3 | 13 |
| 7 | 18 |
| 8 | 25 |
| 9 | 21 |
| 10 | 21 |
| 11 | 24 |
| 13 | 34 |
| 14 | 22 |

TABLE 6

| Compound No. | Inhibition zone diameter (mm) *Candida albicans* (IFO 0538) (B medium, 28° C., 2 days incubation) |
|---|---|
| 2 | 17 |
| 12 | 25 |
| 13(hydrochloride) | 25 |
| 15 | 25 |
| 16 | 25 |
| 17 | 25 |
| 18 | 25 |
| 19 | 30 |
| 20 | 25 |
| 21 | 20 |
| 22 | 25 |
| 23 | 25 |
| 24 | 25 |
| 25 | 40 |
| 26 | 45 |
| 27 | 45 |
| 28 | 40 |
| 29 | 38 |
| 30 | 40 |
| 31 | 40 |
| 32 | 40 |
| 33 | 20 |
| 34 | 30 |
| 35 | 33 |
| 36 | 45 |
| 37 | 45 |
| 38 | 47 |
| 39 | 18 |
| 40 | 50 |
| 43 | 40 |
| 45 | 40 |
| 46 | 27 |
| 47 | 25 |
| 48 | 23 |
| 49 | 25 |
| 50 | 22 |
| 51 | 28 |
| 52 | 35 |
| 53 | 35 |
| 54 | 25 |
| 55 | 30 |
| 56 | 30 |
| 57 | 30 |
| 59 | 30 |
| 60 | 30 |
| 61 | 30 |
| 62 | 45 |
| 115 | 33 |
| 116 | 30 |
| 107 | 33 |
| 110 | 40 |
| 111 | 35 |
| 114 | 15 |
| 108 | 40 |
| 99 | 35 |
| 121 | 35 |
| 112 | 30 |
| 109 | 28 |
| 122 | 35 |
| 123 | 35 |
| 78 | 30 |
| 124 | 30 |
| 125 | 33 |
| 42 | 34 |
| 117 | 25 |
| 118 | 33 |
| 119 | 30 |
| 120 | 30 |
| 126 | 38 |
| 127 | 33 |
| 128 | 30 |
| 129 | 35 |
| 97 | 27 |
| 90 | 35 |
| 91 | 30 |
| 130 | 35 |
| 131 | 40 |
| 101 | 38 |
| 102 | 35 |
| 95 | 28 |

The infection-preventing effect of the compounds (I) evaluated in the experimental infection in mice is shown in Table 7-1 and Table 7-2.

Method 1 (Table 7-1): To 5-week-old Crj:CDF$_1$ mice the minimum lethal dose of *Candida albicans* was inoculated intravenously. The test drug was given twice 0 and 2 hours after infection. The effectiveness of the drug was expressed in ED$_{50}$ values calculated by the Reed and Muench method from the survival rate 7 days after infection. The ED$_{50}$ values were calculated based on the total dose given on the two occasions.

TABLE 7-1

| Compound No. | ED$_{50}$ (mg/kg) | |
|---|---|---|
| 2 | 19.3 | (s.c.) |
| 3 | 32.4 | (s.c.) |
| 10 | 35.4 | (s.c.) |
| 12 | 2.5 | (s.c.) |
| 13(hydrochloride) | 10 | (s.c.) |
| 15 | 2.5 | (s.c.) |
| 16 | 0.63 | (s.c.) |

TABLE 7-1-continued

| Compound No. | ED$_{50}$ (mg/kg) | |
|---|---|---|
| 16(hydrochloride) | 0.71 | (s.c.) |
| | 0.71 | (p.o.) |
| 25 | 3.2 | (s.c.) |
| 26 | 3.2 | (s.c.) |
| 27(hydrochloride) | 3.2 | (s.c.) |
| 28 | 0.65 | (s.c.) |
| 29 | 0.71 | (s.c.) |
| 30(hydrochloride) | 0.88 | (s.c.) |
| 31 | 0.71 | (s.c.) |
| 32 | 3.2 | (s.c.) |
| 33 | 0.45 | (s.c.) |
| 34 | 3.2 | (s.c.) |
| 35 | 0.71 | (s.c.) |
| 36 | 3.2 | (s.c.) |
| 37 | 1.4 | (s.c.) |
| 38(hydrochloride) | 3.2 | (s.c.) |
| 39 | 0.19 | (s.c.) |
| | 0.35 | (p.o.) |
| 40 | 0.35 | (s.c.) |
| 43 | 0.18 | (s.c.) |
| | 0.18 | (p.o.) |
| 45 | 0.16 | (s.c.) |
| | 0.18 | (p.o.) |
| 46 | 0.70 | (s.c.) |
| 47 | 0.70 | (s.c.) |
| 48 | 0.77 | (s.c.) |
| 49 | 1.0 | (s.c.) |
| 50 | 3.2 | (s.c.) |
| 51 | 2.0 | (s.c.) |
| 52 | 2.0 | (s.c.) |
| 53 | 2.0 | (s.c.) |
| 54 | 0.50 | (s.c.) |
| 55 | 0.50 | (s.c.) |
| 56 | 2.0 | (s.c.) |
| 57 | 0.50 | (s.c.) |
| 59 | 1.4 | (s.c.) |
| 60 | >4.0 | (s.c.) |
| 62 | 0.50 | (s.c.) |
| | 0.35 | (p.o.) |
| 107 | 0.71 | (s.c.) |
| | <0.50 | (p.o.) |
| 110 | 0.35 | (s.c.) |
| | 0.35 | (p.o.) |
| 111 | 0.71 | (s.c.) |
| | 0.89 | (p.o.) |
| 115 | >4.0 | (s.c.) |
| 116 | >4.0 | (s.c.) | s.c.: subcutaneous administration
p.o.: oral administration

Method 2 (Table 7-2): To 5-week-old Crj:CDF$_1$ mice the minimum lethal dose of *Candida albicans* was inoculated intravenously. The test drug was given just after infection. The effectiveness of the drug was expressed in ED$_{50}$ values calculated by the Reed and Muench method from the survival rate 7 days after infection. The ED$_{50}$ values were calculated based on the total dose given on the two occasions.

TABLE 7-2

| Compound No. | ED$_{50}$ (mg/kg) | |
|---|---|---|
| 78 | 0.50 | (p.o.) |
| 99 | 1.4 | (p.o.) |
| 107 | 0.39 | (p.o.) |
| 108 | 1.4 | (p.o.) |
| 109 | 0.50 | (p.o.) |
| 112 | 0.50 | (p.o.) |
| 114 | 0.40 | (p.o.) |
| 42 | >4.0 | (p.o.) |
| 117 | >4.0 | (p.o.) |
| 118 | 2.8 | (p.o.) |
| 119 | 0.18 | (p.o.) |
| 120 | 0.35 | (p.o.) |
| 121 | 0.50 | (p.o.) |
| 122 | 0.50 | (p.o.) |
| 123 | 0.50 | (p.o.) |
| 124 | 0.70 | (p.o.) |

TABLE 7-2-continued

| Compound No. | ED$_{50}$ (mg/kg) | |
|---|---|---|
| 125 | 0.50 | (p.o.) |
| 126 | 2.0 | (p.o.) |
| 127 | 2.0 | (p.o.) |
| 128 | 2.0 | (p.o.) |
| 129 | 0.50 | (p.o.) |
| 97 | 0.50 | (p.o.) |
| 90 | 0.35 | (p.o.) |
| 91 | <0.25 | (p.o.) |
| 130 | 0.7 | (p.o.) |
| 131 | 0.7 | (p.o.) | p.o.: oral administration

The compounds of this invention, having low toxicities and high antifungal activities with wide antifungal spectra as shown above, can be used for prevention and treatment of fungal infections in man, domestic animals and fowls.

When the compounds are given to man, the compounds can be given safely orally or parenterally, as they are or in the form of pharmaceutical compositions such as powders, granules, tablets, capsules, and injections produced by mixing with appropriate pharmaceutically acceptable carriers, excipients, or diluents. The dose may vary according to the condition of infection and the route of administration; for example the oral dose for treatment of candida infection for an adult is 0.1 to 100 mg/kg/day, desirably 1 to 50 mg/kg/day.

The compound of this invention also can be used as an antifungal preparation for external application. For example, a skin or a muscosa membrane can be sterilized and disinfected by applying it as an ointment containing 0.1 to 100 mg, preferably 1 to 50 mg, of the compound of this invention per gram.

EXAMPLES

The following Reference Examples and Examples will illustrate the present invention in more detail.

Reference Example 1

A mixture of benzimidazole (4.72g, 40 mmol), bromochloroethane (3.4 ml, 41 mmol), potassium carbonate (5.52 g, 40 mmol) and dimethylformamide (60 ml) was stirred at room temperature for 20 hours. To the reaction mixture were added ethyl acetate and water, which was extracted with ethyl acetate. The organic layer was washed with water and then with a saturated aqueous sodium chloride solution, followed by drying (anhydrous sodium sulfate). The solvent was distilled off, and the residue was subjected to a silica gel chromatography (3.0×40 cm: ethyl acetate-hexane=2:1) to give 1-(2-chloroethyl)benzimidazole (5.56 g, 38%) as a colorless oily substance.

$^1$H-NMR (CDCl$_3$) δ ppm: 3.78(2H,t,J=6 Hz), 4.45(2H,t,J=6 Hz), 7.19–7.40(3H,m), 7.76–7.95(1H,m), 7.90(1H,s)

To a solution of trityl mercaptan (9.7 g, 35 mmol) in ethanol (90 ml) was added, at 0° C., a sodium methoxide-methanol solution (28%) (7.1 ml). To the reaction mixture was added 1-(2-chloroethyl)benzimidazole (6.32 g, 35 mmol), which was heated for 2 hours under reflux. Insoluble substances were filtered off, and the filtrate was concentrated under reduced pressure. The concentrate was subjected to a silica gel column chromatography (3.0×40 cm: ethyl acetate:hexane=1:1→2:1) to give 1-(2-tritylthioethyl)benzimidazole (5.6 g, 38%).

$^1$H-NMR (CDCl$_3$) δ ppm: 2.69(2H,t,J=6.5 Hz), 3.76(2H,t,J=6.5 Hz), 6.90–7.90(21H,m)

To a solution of 1-(2-tritylthioethyl)benzimidazole (7.0 g, 16.6 mmol) in a mixture of methanol (50 ml) and chloroform (80 ml), were added pyridine (1.32 ml, 16.3 mmol) and then silver nitrate (2.9 g, 17.1 mmol). The mixture was stirred for 3 hours at room temperature. Precipitates then separated out were collected and washed with methanol and then with ethyl ether to give silver salt of 1-(2-mercaptoethyl)benzimidazole (4.73 g, 99%). The silver salt (4.73 g, 16.6 mmol) was suspended in dichloromethane (250 ml), which was bubbled with hydrogen sulfide at 0° C. for one hour. Precipitates were filtered off, and the filtrate was concentrated to give 1-(2-mercaptoethyl)benzimidazole (2.35 g, 79%) as colorless powder (2.35 g, 79%).

$^1$H-NMR (DMSO-d$_6$-CDCl$_3$) δ ppm: 2.25(1H,t,J=7.5 Hz), 3.07(2H,q,J=7.5 Hz), 4.73(2H,t,J=7.5 Hz), 7.40–8.10(4H,m), 9.69(1H,s)

Reference Example 2

A mixture of 1H-1,2,4-triazole (10.3 g), 1,3-oxathiolan-2-one (5.2 g) and toluene (100 ml) was heated for 4 days under reflux. The solvent was distilled off under reduced pressure. To the residue was added a saturated aqueous sodium chloride solution (50 ml), followed by extraction four times with methylene chloride (50 ml). The extract solution was dried (anhydrous magnesium sulfate) and subjected to distillation under reduced pressure. The residue was purified by means of a silica gel column chromatography (ethyl acetate→ethyl acetate:acetone=2:1) to give 2-(1,2,4-triazol-1-yl)ethanethiol (2.5 g) as a colorless oily substance.

$^1$H-NMR (CDCl$_3$) δ: 1.35(1H,t,J=8.8 Hz), 3.01(2H,m), 4.37(2H,t,J=6.6 Hz), 7.99(1H,s), 8.18(1H,s)

Reference Example 3

To imidazole (2.16 g, 32 mmol) was added methanesulfonic acid (1.03 ml, 16 mmol), which was stirred for 5 minutes at room temperature. To the reaction mixture was added ethylene sulfide (1.04 ml, 18 mmol), which was stirred for 17 hours at 55° C. The reaction mixture was subjected to a silica gel column chromatography (3.0×30 cm: ethyl acetate:methanol=10:1) to afford 2-(1-imidazolyl)ethanethiol (0.85 g, 38%) as a pale yellow oily substance.

$^1$H-NMR (CDCl$_3$) δ ppm: 1.75(1H,t,J=8 Hz), 2.84(2H,t,J=7.5 Hz), 4.13(2H,t,J=7.5 Hz), 7.10(2H,s), 7.51(1H,s)

Reference Example 4

A mixture of imidazole (13.6 g, 0.2 mol), bromochloroethane (16.6 ml, 0.2 mol), potassium carbonate (0.2 mol) and dimethylformamide (100 ml) was stirred for 20 hours at room temperature. Insoluble substances were filtered off, and the filtrate was concentrated under reduced pressure to give 1-(2-chloroethyl)imidazole as a pale yellow liquid substance.

$^1$H-NMR (CDCl$_3$) δ ppm: 3.76(2H,t,J=6 Hz), 4.29(2H,t,J=6 Hz), 7.01(1H,s), 7.07(1H,s), 7.57(1H,s)

In ethanol (30 ml) was dissolved 1-(2-chloroethyl)imidazole, to which were added 1,2-ethanedithiol (25 ml) and sodium methoxide (28% methanol solution) (16.6 ml), and the mixture was heated for 30 minutes under reflux. Insoluble substances were filtered off, and the filtrate was concentrated under reduced pressure. To the concentrate was added dichloromethane (300 ml). The organic layer was washed with water, then with a saturated aqueous sodium chloride solution, followed by drying (sodium sulfate). The solvent was distilled off, and the residue was subjected to a silica gel column chromatography (3.0×40 cm:ethyl acetate→ethyl acetate:methanol=10:1) to give 2-[2-(1-imidazolyl)ethylthio]ethanethiol (3.0 g) as a pale yellow oily substance.

$^1$H-NMR (CDC$_3$) δ ppm: 1.70(1H,t,J=7.8 Hz), 2.55–2.70(4H,m), 2.89(2H,t,J=6.8 Hz), 4.15(2H,t,J=6.8 Hz), 6.97(1H,s), 7.08(1H,s), 7.55(1H,s)

Reference Example 5

To ethanol (100 ml) containing ethanedithiol (5.0 ml) and a 28% sodium methylate methanol solution (11.5 g) was added 2-chloromethyl-1-methyl imidazole hydrochloride (2.0 g). The mixture was stirred for 15 minutes. Ethanol was distilled off under reduced pressure. The residue was neutralized with 5N aqueous solution of hydrochloric acid (9.5 ml), which was subjected to distillation under reduced pressure. The residue was subjected to a silica gel chromatography (3.5×15 cm), followed by elution with methanol-ethyl acetate (5:95). The object fraction was concentrated to afford 2-(1-methyl-2-imidazolylthio)ethanethiol (1.4 g) as a colorless oily substance.

$^1$H-NMR (CDCl$_3$) δ: 1.62(1H,t,J=7.8 Hz), 2.55–2.80(4H,m), 3.69(3H,s), 3.81(2H,s), 6.87(1H,d,J=1.4 Hz), 6.91(1H,d,J=1.4 Hz)

Reference Example 6

To an acetone (40 ml) solution containing 2-mercapto-1-methylimidazole (4.0 g) and anhydrous potassium carbonate (20 g) was added dropwise, under ice-cooling, 1-bromo-2-chloroethane (5.0 ml). The mixture was stirred for 2 hours at room temperature, to which was added methylene chloride (40 ml), followed by filtration. The filtrate was concentrated under reduced pressure to give 2-(2-chloroethyl thio)-1-methylimidazole (6.2 g) as a colorless oily substance.

$^1$H-NMR (CDC$_3$) δ: 3.35(2H,t,J=7.0 Hz), 3.63(3H,s), 3.75 (2H,t,J=7.0 Hz), 6.94 (1H,d,J=1.2 Hz), 7.05 (1H,d,J=1.2 Hz)

Reference Example 7

In dimethylformamide (100 ml) were dissolved 1H-1,2,4-triazole (13.8 g) and 1-bromo-2-chloroethane (28.7 g). To the solution was added potassium carbonate (27.6 g), and the mixture was stirred for 4 days. The solvent was distilled off under reduced pressure. To the residue was added dichloromethane (100 ml). Insoluble substances were filtered off, and the filtrate was concentrated to give 1-(2-chloroethyl)-1H-1,2,4-triazole (23.3 g).

$^1$H-NMR (200 MHz, CDCl$_3$) δ: 3.90(2H,t,J=5.7 Hz), 4.51(2H,t,J=5.7 Hz), 7.99(1H,s), 8.17(1H,s)

This chloroethyl compound (2.8 g) and 1,2-ethanedithiol(4.2 g) were dissolved in ethanol (30 ml), to which was added a 28% sodium methylate-methanol solution (3.6 ml), and the mixture was heated for 30 minutes under reflux. The solvent was distilled off under reduced pressure. The residue was purified by means of a silica gel chromatography (eluent: ethyl acetate) to give 2-[2-(1H-1,2,4-triazol-1-yl)ethylthio]ethanethiol (2.03 g) as a colorless oily substance.

$^1$H-NMR (CDCl$_3$) δ: 1.67(1H,t,SH), 2.62(4H,m), 3.02(2H,t,J=6.5 Hz), 4.36(2H,t,J=6.5 Hz), 7.97(1H,s), 8.14(1H,s)

Reference Example 8

To a dimethylformamide (160 ml) solution of 2-(2,4-difluorophenyl)-2-(1H-1,2,4-triazol-1-yl-methyl)oxirane (8.0 g) and methyl ester of 3-mercaptopropionic acid was added, under ice-cooling, 60% sodium hydride (4.0 g). The mixture was stirred for 15 minutes, to which was added dropwise a 1N aqueous solution of hydrochloric acid (101 ml) to adjust the pH to 7, followed by distilling off dimethylformamide and water. To the residue was added water (20 ml), which was extracted with ethyl acetate (50 ml×3). The extract was washed with a saturated aqueous sodium chloride solution, then dried over anhydrous sodium sulfate, followed by distilling off the solvent. The residue was subjected to a silica gel chromatography (6.0×9.0 cm), followed by elution with ethyl acetate-hexane (3:1). The object fraction was concentrated, to which was added diethyl ether to afford 2-(2,4-difluorophenyl)-3-mercapto-1-(1H-1,2,4-triazol-1-yl)propan-2-ol (6.44 g) as colorless needles, m.p. 112°–113° C.

Elemental Analysis for $C_{11}H_{11}F_2N_3OS$: Calcd.: C, 48.70; H, 4.09; N, 15.49 Found: C, 48.96; H, 4.11; N, 15.62 $^1$H-NMR (CDCl$_3$) δ: 1.37(1H,d,d,J=6.80 Hz, 10.8 Hz), 2.84(1H,d,d,J=10.8 Hz, 13.8 Hz), 3.27(1H,d,d,J=6.80 Hz, 13.8 Hz), 4.53(1H,s), 4.72(2H,s), 6.74~6.88(2H,m), 7.42~7.55(1H,m), 7.83(1H,s), 8.00(1H,s)

Reference Example 9

To an acetone (50 ml) solution containing 2-mercapto-1-methyltetrazole (4.0 g) and anhydrous potassium carbonate (20 g) was added 1-bromo-2-chloroethane (5.0 ml) under ice-cooling. The mixture was stirred for 90 minutes at room temperature, to which was added methylene chloride (50 ml). The mixture was subjected to filtration, and the filtrate was concentrated under reduced pressure to afford 2-(chloroethylthio)-1-methyltetrazole (6.0 g) as a pale yellow oily substance.

$^1$H-NMR (CDCl$_3$) δ: 3.69(2H,t,J=6.8 Hz), 3.92(2H,t,J=6.8 Hz), 3.96(3H,s)

Reference Example 10

A methanol (2.0 ml) solution containing (2RS,3RS)-2-(2,4-difluorophenyl)-3-methyl-2-(1H-1,2,4-triazol-1-ylmethyl)oxirane (0.05 g), methyl 3-mercaptopropionate (0.11 ml) and a 28% sodium methylate-methanol solution (0.14 ml) was refluxed for 1.0 hour. The reaction mixture was cooled, to which was added water (10 ml). The mixture was neutralized with 1N aqueous solution of hydrochloric acid, followed by extraction with methylene chloride (5.0 ml×twice). The extract solution was dried over anhydrous sodium sulfate, then the solvent was distilled off. The residue was subjected to a silica gel chromatography (2.5 cm×5 cm), followed by elution with ethyl acetate-hexane (1:2). The object fraction was concentrated, to which was added ethyl acetate to give (2RS,3RS)-2-(2,4-difluorophenyl)-3-mercapto-1-[(1H)-1,2,4-triazol-1-yl]-2-butanol (0.030 g) as colorless needles.

$^1$H-NMR (CDCl$_3$) δ: 1.17(3H,d,J=7.0 Hz), 1.96(1H,d,J=10.2 Hz), 3.45(1H,d,q,J=7.0 Hz,J=10.2 Hz), 4.77(1H,s), 4.82(1H,d,J=14.4 Hz), 5.01(1H,d,J=14.4 Hz), 6.70~6.81(2H,m), 7.33~7.45(1H,m), 7.79(1H,s), 7.80(1H,s)

This product was recrystallized from ethyl acetate to afford colorless prisms, m.p. 145°–147° C.

Reference Example 11

An ethanol (20 ml) solution of 2-chloromethylimidazo[1,2-a]pyridine hydrochloride (2.0 g) was added, at 80° C., to ethanol (20 ml) containing a 28% sodium methylate methanol solution. The mixture was refluxed for 2.5 hours. The reaction mixture was cooled, to which was added dilute hydrochloric acid to adjust the pH to 1, followed by washing with toluene (30 ml×three times). To the aqueous layer was added an aqueous solution of sodium hydroxide to adjust the pH to 10, followed by extraction with methylene chloride (30 ml×three times). The organic layer was dried over anhydrous sodium sulfate, which was concentrated under reduced pressure. The concentrate was subjected to a silica gel chromatography (3 cm×15 cm), eluting with ethyl acetate-hexane (2:1). The object fraction was concentrated under reduced pressure to give 2-(4-methoxybenzylthio)methylimidazo[1,2-a]pyridine (2.5 g) as a colorless oily product $^1$H-NMR (CDCl$_3$) δ: 3.73(2H,s), 3.78(2H,s) 3.79(3H,s), 6.75(1H,m), 6.83(2H,d,J=6.6 Hz) 7.13(1H,m), 7.25(2H,d,J=6.6 Hz), 7.46(1H,s) 7.55(1H,d,J=9.0 Hz), 8.04(1H,d,d,J=1.0 Hz,5.6 Hz)

To the mixture of this product (2.5 g), anisole (20 ml) and trifluoroacetic acid (50 ml) was added silver acetate (II) (3.2 g), which was stirred for 4 hours at room temperature. The reaction mixture was concentrated under reduced pressure. To the concentrate was added petroleum ether. The colorless powder then separated out was collected by filtration and washed with diethyl ether. The obtained powder (5.0 g) was suspended in N,N-dimethylformamide (60 ml), into which was blown hydrogen sulfide until the reaction mixture was colored black. This reaction mixture was bubbled with nitrogen gas to remove excess volume of hydrogen sulfide, which was then subjected to filtration. The filtrate was concentrated under reduced pressure. The residue was subjected to a silica gel chromatography (2.0 cm×15 cm), followed by elution with methanol-methylene chloride (1:19). The object fraction was concentrated under reduced pressure. To the concentrate were added methanol and methylene chloride to afford 2-mercaptomethylimidazo[1,2-a]pyridine (1.3 g) as colorless needles, m.p. 168°–178° C.

$^1$H-NMR (DMSO-d$_6$) δ: 3.30(1H,t,J=8.0 Hz), 4.00(2H,d,J=8.0 Hz), 7.36(1H,dt,J=1.8 Hz,J=6.6 Hz), 7.75~7.89(2H,m), 8.16(1H,s), 8.82(1H,d,J=7.2 Hz)

Reference Example 12

To a suspension of imidazole-2-carboxyaldehyde (2.5 g) in N,N-dimethylformamide (25 ml) was added 60% sodium hydride in oil (1.2 g) at room temperature, and the mixture was stirred for 30 minutes. To the resultant solution was added, at room temperature, 2,2,3,3-tetrafluoropropyl-p-toluenesulfonate (11.2 g), and the mixture was stirred for 2.5 hours at 110° C. The reaction mixture was cooled, to which was added water (100 ml) and toluene (30 ml) for extraction. The aqueous layer was subjected to further extraction with toluene (30 ml×3 times). Toluene layers were combined and washed with a saturated aqueous sodium chloride solution (30 ml), which was dried over anhydrous sodium sulfate, then the solvent was distilled off under reduced pressure. The residue was subjected to a silica gel chromatography (3.0 cm×10 cm), eluting with ethyl acetate-hexane (1:1). The object fraction was concentrated to give 1-(2,2,3,3-tetrafluoropropyl)imidazol-2-carboxyaldehyde (2.7 g) as colorless plates, m.p. 51°–54° C.

$^1$H-NMR (CDCl$_3$) δ: 5.15(2H,t,J=12.6 Hz), 5.92(1H,t,t,J=54 Hz,2.6 Hz), 7.27(1H,s), 7.38(1H,s), 9.84(1H,s) Elemental Analysis for C$_7$H$_6$F$_4$N$_2$O: Calcd.: C, 40.01; H, 2.88; N, 13.33 Found: C, 39.68; H, 2.86; N, 13.11.

To a solution of 1-(2,2,3,3-tetrafluoropropyl)-imidazole-2-carboxyaldehyde (1.5 g) in methanol (15 ml) was added sodium borohydride (0.08 g) at 0° C., which was stirred for 40 minutes at 0° C. To the reaction mixture was added a saturated aqueous sodium chloride solution (5.0 ml), which was stirred for 50 minutes, followed by extraction with ethyl acetate (30 ml×4 times). The organic layer was dried over anhydrous magnesium sulfate, then the solvent was distilled off under reduced pressure. Addition of ethyl acetate and hexane to the residue gave precipitates of 2-hydroxymethyl-1-(2,2,3,3-tetrafluoropropyl)imidazole (1.5 g) as colorless needles, m.p. 91°–92° C.

Elemental Analysis for C$_7$H$_8$F$_4$N$_2$O: Calcd.: C, 39.63; H, 3.80; N, 13.20 Found: C, 39.79; H, 3.78; N, 13.20
$^1$H-NMR (CDCl$_3$) δ: 4.68(2H,t,J=12.4 Hz), 4.68(2H,s), 5.88(1H,t,t,J=53.2 Hz, 2.6 Hz), 6.93(1H,s), 6.96(1H,s)

To thionyl chloride (7.0 ml) was gradually added 2-hydroxymethyl-1-(2,2,3,3-tetrafluoropropyl)imidazole (0.70 g) at 0° C., and the mixture was refluxed for 45 minutes. The reaction mixture was concentrated under reduced pressure, to which was added diethyl ether, then precipitating crystals were collected by filtration. The crystals were dissolved in ethanol, followed by recrystallization from diethyl ether to give 2-chloromethyl-1-(2,2,3,3-tetrafluoropropyl)imidazole hydrochloride (0.90 g) as colorless needles, m.p. 104°–107° C.

Elemental Analysis for C$_7$H$_8$Cl$_2$F$_4$N$_2$: Calcd.: C, 31.48; H, 3.02; N, 10.49 Found: C, 31.74; H, 2.94; N, 10.44 $^1$H-NMR (DMSO-d$_6$) δ: 5.13(2H,s), 5.17(2H,t,J=16.2 Hz), 6.76(1H,t,t,J=51.8 Hz,5 Hz), 7.66(1H,d,J=1.8 Hz), 7.69(1H,br.s)

Reference Example 13

A mixture of 1H-1,2,4-triazole (20 g) and paraformaldehyde (9.0 g) was heated at 170° C. for 1.5 hour, to which was further added paraformaldehyde (9.0 g). The mixture was heated at 170° C. for 1.5 hour, to which was further added paraformaldehyde (9.0 g). The mixture was heated at 170° C. for 1.5 hour, and then subjected to distillation under reduced pressure to remove remaining triazole. The residue was cooled, to which was added N,N-dimethylformamide (150 ml). To the mixture was added, under ice-cooling, tert-butyldimethylsilyl chloride (25 g), followed by stirring for 1.25 hour at room temperature. The reaction mixture was concentrated under reduced pressure, to which was added a saturated aqueous solution of sodium hydrogen carbonate (100 ml), followed by extraction with methylene chloride (30 ml×3 times). The organic layer was dried over anhydrous sodium sulfate, which was then concentrated under reduced pressure. The concentrate was subjected to a silica gel chromatography (5.0 cm×20 cm), eluting with ethyl acetate-hexane (3:1). The object fraction was concentrated to afford 3-tert-butyldimethyl-siloxymethyl-1H-1,2,4-triazole (15 g) as a colorless oily product.

$^1$H-NMR (CDCl$_3$) δ: 0.13(6H,s), 0.93(9H,s), 4.94(2H,s), 8.03(1H,s)

A solution of 3-tert-butyldimethylsiloxymethyl-1H-1,2,4-triazole (8.0 g) in N,N-dimethylformamide (20 ml) was added dropwise at 0° C. to a mixture of 60% sodium hydride in oil (1.5 g), methyl iodide (2.8 ml) and N,N-dimethylformamide (80 ml) for 10 minutes. The mixture was stirred for 10 minutes, to which was added water (300 ml), followed by extraction with ethyl acetate (100 ml×3 times). The organic layer was washed with a saturated aqueous sodium chloride solution, which was then dried over anhydrous sodium sulfate, followed by concentration under reduced pressure. The concentrate was subjected to a silica gel chromatography, eluting with ethyl acetate-hexane (1:1), then further with ethyl acetate. The object fractions were respectively concentrated under reduced pressure to afford 5-tert-butyldimethylsiloxymethyl-1-methyl-1H-1,2,4-triazole (4.4 g), 3-tert-butyldimethylsiloxymethyl-1-methyl-1H-1,2,4-triazole (2.4 g), and 3-tert-butyldimethylsiloxymethyl-4-methyl-4H-1,2,4-triazole (0.50 g).

5-tert-butyldimethylsiloxymethyl-1-methyl-1H-1,2,4-triazole: colorless oil
$^1$H-NMR (CDCl$_3$) δ: 0.09(6H,s), 0.90(9H,s), 3.96(3H,s), 4.85(2H,s), 7.79(1H,s) 3-tert-butyldimethylsiloxymethyl-1-methyl-1H-1,2,4-triazole: colorless oil
$^1$H-NMR (CDCl$_3$) δ: 0.13(6H,s), 0.93(9H,s), 3.90(3H,s), 4.77(2H,s), 7.97(1H,s) 3-tert-butyldimethylsiloxymethyl-4-metyl-4H-1,2,4-triazole: colorless needles
$^1$H-NMR (CDCl$_3$) δ: 0.09(6H,s), 0.89(9H,s) 3.76(3H,s), 4.90(2H,s), 8.08(1H,s) m.p. (crystallized from diethyl ether) 94° C.~95° C.

A mixture of 5-tert-butyldimethylsiloxymethyl-1-methyl-1H-1,2,4-triazole (3.0 g), ethanol (20 ml), 5N aqueous solution of sodium hydroxide (4.0 ml) and methanol (30 ml) was stirred for 24 hours at room temperature. The reaction mixture was concentrated under reduced pressure, and the concentrate was subjected to a silica gel chromatography (3.0 cm×15 cm), eluting with methanol-methylene chloride (1:9). The object fraction was concentrated under reduced pressure to give 5-hydroxymethyl-1-methyl-1H-1,2,4-triazole (1.2 g) as a colorless solid product.

$^1$H-NMR (CDCl$_3$) δ: 3.95(3H,s), 4.76(2H,br.s), 5.33(1H,br.), 7.78(1H,s)

To thionyl chloride (8.0 ml) was gradually added 5-hydroxymethyl-1-methyl-1H-1,2,4-triazole (0.80 g) at 0° C., followed by refluxing for 3 hours. The reaction mixture was concentrated under reduced pressure. To the concentrate was added diethyl ether, then resulting powdery product was collected by filtration. The powdery product was dissolved in ethanol, to which was added diethyl ether to cause crystallization to afford 5-chloromethyl-1-methyl-1H-1,2,4-triazole hydrochloride (1.1 g) as colorless plates, m.p. 77°–78° C.

Elemental Analysis for C$_4$H$_7$Cl$_2$N$_3$.½H$_2$O: Calcd.: C, 27.14; H, 4.55; N, 23.74 Found: C, 27.60; H, 3.98; N, 23.66 $^1$H-NMR (DMSO-d$_6$) δ: 3.92(3H,s), 5.01(2H,s), 8.01(1H,s)

A mixture of 3-tert-butyldimethylsiloxymethyl-1-methyl-1H-1,2,4-triazole (2.0 g), ethanol (10 ml), methanol (20 ml) and 5N aqueous solution of sodium hydroxide (2.6 ml) was stirred for 27 hours at room temperature, followed by stirring further 21 hours at 45° C. The reaction mixture was concentrated under reduced pressure. The residue was subjected to a silica gel chromatography (2.0 cm×10 cm), eluting with methanol-methylene chloride (1:9). The object fraction was concentrated under reduced pressure to afford 3-hydroxymethyl-1-methyl-1H-1,2,4-triazole (1.0 g) as colorless needles.

$^1$H-NMR (CDCl$_3$) δ: 3.91(3H,s), 4.75(2H,d,J=3.6 Hz), 4.06(1H,br.), 8.02(1H,s) m.p. 72°~75° C.

To thionyl chloride (8.0 ml) was gradually added at 0° C. 3-hydroxymethyl-1-methyl-1H-1,2,4-triazole (0.60 g), which was refluxed for 3 hours. The reaction mixture was concentrated under reduced pressure, to which was added diethyl ether. Resulting powder was crystallized from a mixture of ethanol and diethyl ether to give 3-chloromethyl-1-methyl-1H-1,2,4-triazole hydrochloride (1.0 g) as colorless needles, m.p. 69°–70° C.

Elemental Analysis for C$_4$H$_7$Cl$_2$N$_3$: Calcd.: C, 28.59; H, 4.20; N, 25.01 Found: C, 28.16; H, 4.08; N, 24.51
$^1$H-NMR (DMSO-d$_6$) δ: 3.87(3H,s), 4.72(2H,s), 8.57(1H,s)

A mixture of 3-tert-butyldimethylsiloxymethyl-4-methyl-4H-1,2,4-triazole (0.40 g), ethanol (12 ml) and 5N sodium hydroxide (0.53 ml) was stirred for 48 hours at room temperature. The reaction mixture was concentrated under reduced pressure, and the concentrate was subjected to a silica gel chromatography (2.0 cm×10 cm), eluting with methanol-methylene chloride (1:4). The object fraction was concentrated under reduced pressure to give 3-hydroxymethyl-4-methyl-4H-1,2,4-triazole (0.20 g) as a colorless solid. $^1$H-NMR (DMSO-d$_6$) δ: 3.66(3H,s), 4.59(2H,d,J=5.6 Hz), 5.52(1H,t,J=5.6 Hz), 8.40(1H,s)

To thionyl chloride (2.0 ml) was added at 0° C. 3-hydroxymethyl-4-methyl-4H-1,2,4-triazole (0.15 g), and the mixture was refluxed for 1.5 hour. The reaction mixture was concentrated under reduced pressure, to which was added diethyl ether. Resulting crystals were collected by filtration and dissolved in ethanol, to which was added diethyl ether for recrystallization to afford 3-chloromethyl-4-methyl-4H-1,2,4-triazole hydrochloride (0.22 g) as colorless prisms, m.p. 96°–97° C.

Elemental Analysis for C$_4$H$_7$Cl$_2$N$_3$: Calcd.: C, 28.59; H, 4.20; N, 25.01 Found: C, 28.70; H, 4.18; N, 24.91
$^1$H-NMR (DMSO-d$_6$) δ: 3.81(3H,s), 5.11(2H,s), 9.26(1H,s)

Reference Example 14

3-Hydroxymethyl-5-mercapto-4-methyl-4H-1,2,4-triazole (1.5 g) was added, taking 1 hour at 0° C., to a mixture of conc. nitric acid (d 1.38) (2.3 ml), water (6.0 ml) and sodium nitrite (0.005 g). The reaction mixture was warmed to room temperature, which was then allowed to stand for one hour, followed by addition of an aqueous solution of sodium hydroxide to adjust the pH to 8. Water was then distilled off under reduced pressure, and the residue was subjected to a silica gel chromatography (2.5 cm×10 cm), eluting with methanol-methylene chloride (1:4). The object fraction was concentrated, and the concentrate was recrystallized from ethyl acetate to give 3-hydroxymethyl-4-methyl-4H-1,2,4-triazole (1.1 g) as colorless needles.
$^1$H-NMR (DMSO-d$_6$) δ: 3.66(3H,s), 4.59(2H,d,J=5.6 Hz), 5.52(1H,t,J=5.6 Hz), 8.40(1H,s) m.p. 81°~82° C.

Reference Example 15

A mixture of 6,7-dihydro-5H-pyrrolo[1,2-c]imidazole (7 g) and paraformaldehyde (4 g) was heated at 160° C., to which was added, 20 minutes later, paraformaldehyde (2 g), and, further 20 minutes later, paraformaldehyde (1 g), followed by heating for 45 minutes. The reaction mixture was subjected to a silica gel chromatography (4.0 cm×15 cm), eluting with methanol-methylene chloride (1:9). The object fraction was concentrated. To the concentrate were added ethanol and diethyl ether to give 6,7-dihydro-3-hydroxymethyl-5H-pyrrolo[1,2-c]imidazole (3.4 g) as colorless needles, m.p. 110°–120° C.

Elemental Analysis for C$_7$H$_{10}$N$_2$O: Calcd.: C, 60.85; H, 7.29; N, 20.27 Found: C, 61.08; H, 7.30; N, 20.27
$^1$H-NMR (CDCl$_3$) δ: 2.5~2.7 (2H,m), 2.81(2H,t,J=7.4 Hz), 4.01(2H,t,J=7.0 Hz), 4.56(2H,s), 6.2(1H,br.), 6.54(1H,s)

6,7-Dihydro-3-hydroxymethyl-5H-pyrrolo[1,2-c]imidazole (0.8 g) was gradually added at 0° C. to thionyl chloride (0.8 ml), and the mixture was refluxed for 40 minutes, followed by distilling off the thionyl chloride under reduced pressure. To the residue was added diethyl ether, then the resulting solid matter was collected by filtration. The solid matter was dissolved in ethanol, to which was added diethyl ether, whereupon 3-chloromethyl-6,7-dihydro-5H-pyrrolo[1,2-c]imidazole.hydrochloride (0.70 g) as pale brown needles, m.p. 120°–140° C.

Elemental Analysis for C$_7$H$_{10}$Cl$_2$N$_2$: Calcd.: C, 43.55; H, 5.22; N, 14.51 Found: C, 43.74; H, 5.21; N, 14.31
$^1$H-NMR (DMSO-d$_6$) δ: 2.5~2.7(2H,m), 2.96(2H,t,J=6.8 Hz), 4.28(2H,t,J=7.0 Hz), 5.16(2H,s), 7.43(1H,s)

Reference Example 16

A mixture of 2-acetoxythioacetamide (10 g), 2-chlorocyclopentanone (10.6 g) and dimethylformamide (100 ml) was stirred for 24 hours at 80° C. The reaction mixture was cooled and poured into ice-water (500 ml), followed by extraction twice with ethyl acetate (200 ml). The extract was washed twice with water (100 ml), which was dried over magnesium sulfate, then the solvent was distilled off under reduced pressure. The residue was subjected to a silica gel chromatography (2.5×50 cm), eluting with ethyl acetate-hexane (3:7). The object fraction was concentrated to give 2-acetoxymethyl-5,6-dihydro-4H-cyclopentathiazole (5 g) as a yellow oily product.

To the above product (5 g) was added 5N-sodium hydroxide (10 ml), which was stirred for 2 hours at 80° C. The reaction mixture was cooled and neutralized with 2N-hydrochloric acid, followed by extraction with ethyl acetate (200 ml). The extract was washed with water (50 ml) and dried over magnesium sulfate, then the solvent was distilled off under reduced pressure. The residue was subjected to a silica gel chromatography (2.5×30 cm), eluting with ethyl acetate-dichloromethane (3:2). The object fraction was concentrated to give 2-hydroxymethyl-5,6-dihydro-4H-cyclopentathiazole (3.5 g) as a yellow oily product.
$^1$H-NMR (CDCl$_3$) δ: 2.40~2.59(4H,m), 2.74~2.99(4H,m), 3.49(1H,bs), 4.85(2H,s)

The above-mentioned product (0.17 g) was dissolved in methylene chloride (4 ml), to which was added dropwise thionyl chloride (1.52 ml), followed by stirring for 30 minutes at room temperature. The solvent was distilled off under reduced pressure to afford 2-chloromethyl-5,6-dihydro-4H-cyclopentathiazole hydrochloride (0.22 g) as a reddish oily product.

Reference Example 17

To a mixture of m-difluorobenzene (75 ml) and anhydrous aluminium chloride (115 g) was added dropwise, while stirring, 2-bromopropionyl chloride (100 g) during 50 minutes. The mixture was stirred for 2 hours on an oil bath at 50°–55° C. The reaction mixture was cooled, to which was added methylene chloride (500 ml). The resultant solution was added, in limited amounts, to ice-water (1.5 l) while stirring. The methylene chloride layer was separated, and the aqueous layer was subjected to extraction twice with methylene chloride (100 ml). The methylene chloride layers were combined and washed with water (500 ml), which was dried over anhydrous magnesium sulfate. The solvent was distilled off under reduced pressure to leave 2-bromo-2',4'-difluoropropiophenone (142.5 g) as a pale yellow oily product. $^1$H-NMR (CDCl$_3$) δ: 1.90(3H), 5.25(1H), 6.85~7.06(2H), 7.93~8.05(1H)

Reference Example 18

To a mixture of m-difluorobenzene (100 ml) and anhydrous aluminium chloride (114 g) was added dropwise, while stirring, propionyl chloride (66 ml), during 45 minutes. The mixture was then stirred for 2 hours on an oil bath of 50°–55° C. The reaction mixture was cooled, to which was added methylene chloride (300 ml). The resultant solution was added by portions to ice-water (1l) while stirring. Methylene chloride layer was separated, and the aqueous layer was subjected to extraction twice with methylene chloride (60 ml). Methylene chloride layers were combined and washed with water (200 ml), followed by drying over anhydrous magnesium sulfate. The solvent was distilled off to leave 2',4'-difluoropropiophenone (111.4 g) as a pale yellow oily product. $^1$H-NMR (CDCl$_3$) δ: 1.17~1.24(3H), 2.92~3.05(2H), 6.82~7.02(2H), 7.89~8.03(1H)

Reference Example 19

In methylene chloride (300 ml) was dissolved 2',4'-difluoropropiophenone (55 g), to which was added bromine (50 g) dropwise, while stirring, during 30 minutes. The mixture was stirred for 30 minutes at room temperature. To the reaction mixture was added water (200 ml), and the methylene chloride layer was washed three times, followed by drying over anhydrous magnesium sulfate. The solvent was distilled off to leave 2-bromo-2',4'-difluoropropiophenone (77 g) as a pale yellow oily product.

Reference Example 20

2-Bromo-2',4'-difluoropropiophenone (141 g) was dissolved in methanol (1100 ml), to which was added sodium formate (176.2 g), and the mixture was stirred for 2 days at 50° C. Methanol was distilled off under reduced pressure. The residue was subjected to extraction by the addition of ethyl acetate (700 ml) and water (500 ml). The ethyl acetate layer was dried over magnesium sulfate, then the solvent was distilled off under reduced pressure. The residue was crystallized from hexane (200 ml) to afford 2',4'-difluoro-2-hydroxypropiophenone (50.5 g) as colorless prisms, m.p. 49°–51° C. NMR (CDCl$_3$) δ: 1.40,1.41(3H,dx2,J=7 Hz), 3.74(1H,d,J=6.2 Hz), 4.96~5.11(1H,m), 6.87~7.27(2H,m), 7.69~8.09(1H,m)

Reference Example 21

2',4'-Difluoro-2-hydroxypropiophenone (61 g) was dissolved in methylene chloride (500 ml), to which was added, under ice-cooling, p-toluene sulfonic acid.hydrate (1.0 g). To the mixture was added, under ice-cooling while stirring, 3,4-dihydro-2H-pyran (41.4 g) during 10 minutes. The mixture was stirred, under ice-cooling, for one hour, to which was added a 5% aqueous solution of sodium hydrogen carbonate (240 ml). The mixture was stirred for 10 minutes under ice-cooling. The methylene chloride layer was separated and dried over anhydrous magnesium sulfate, followed by distilling off the solvent. The residual oily product was purified by means of a silica gel column chromatography (hexane: ethyl acetate=5:1) to afford 2',4'-difluoro-2-(3,4,5,6-tetrahydro-2H-pyran-2-yloxy)propiophenone (86.5 g) as a pale yellow oily product.

Reference Example 22

To dimethyl sulfoxide (650 ml) was added, at room temperature, 60% sodium hydride in oil (15.2 g) by portions during 10 minutes. The mixture was stirred for 10 minutes at room temperature, to which was added by portions trimethylsulfoxonium iodide (83.7 g) during one hour. To the resultant mixture was added dropwise during one hour a solution of 2',4'-difluoro-2-(3,4,5,6-tetrahydro-2H-pyran-2-yloxy)propiophenone (86.5 g) in dimethyl sulfoxide (150 ml). The mixture was stirred for 3 hours at room temperature, then the reaction mixture was poured into ice-water (1.5 l), which was subjected to extraction 5 times with ethyl acetate (300 ml). The ethyl acetate layer was washed with water (300 ml) for four times, followed by drying over anhydrous magnesium sulfate. The solvent was distilled off under reduced pressure to leave 2-[1-(3,4,5,6-tetrahydro-2H-pyran-2-yloxy)ethyl]-2-(2,4-difluorophenyl)oxirane (83.4 g) as a pale yellow oily product.

Reference Example 23

To N,N-dimethylformamide (700 ml) was added, at room temperature while stirring, 60% sodium hydride in oil (35.2 g) by portions during 10 minutes. The mixture was stirred for 5 minutes at room temperature, to which was added 1H-1,2,4-triazole (25 g) by portions at room temperature during 20 minutes. The reaction mixture was cooled with ice, to which was added 1H-1,2,4-triazole (44.6 g) during 30 minutes with stirring, followed by stirring at room temperature for further 10 minutes. To the resultant mixture was added dropwise 2-[1-(3,4,5,6-tetrahydro-2H-pyran-2-yloxy)ethyl]-2-(2,4-difluorophenyl)oxirane (83.4 g) during 5 minutes, which was stirred for 4 hours at 90° C. The reaction mixture was cooled and poured into ice-water (1.5 l), which was subjected to extraction with ethyl acetate (500 ml) for 4 times. The ethyl acetate layer was washed with water (300 ml) 3 times and dried over anhydrous magnesium sulfate. Then the solvent was distilled off to leave a pale yellow oily product. This product was purified by means of a silica gel column chromatography (hexane:acetone=4:1~1:1). The resultant oily product was crystallized from hexane to give 2-(2,4-difluorophenyl)-3-(3,4,5,6-tetrahydro-2H-pyran-2-yl)oxy-1-(1H-1,2,4-triazol-1-yl)-2-butanol (51.4 g) as colorless powder, m.p. 93°–95° C. Elemental Analysis for C$_{17}$H$_{21}$F$_2$N$_3$O$_3$: Calcd.: C, 57.78; H, 5.99; N, 11.89 Found: C, 57.82; H, 6.04; N, 11.77.

Reference Example 24

In ethanol (500 ml) was dissolved 2-(2,4-difluorophenyl)-3-(3,4,5,6-tetrahydro-2H-pyran-2-yl)oxy-1-(1H-1,2,4-triazol-1-yl)-2-butanol (51.4 g), to which was added pyridinium p-toluenesulfonate (13.2 g), and the mixture was stirred for 6 hours at 55° C. To the resultant mixture was further added pyridinium p-toluenesulfonate (2.0 g), which was stirred for 1.5 hour at 55° C. The mixture was cooled, then the solvent was distilled off under reduced pressure. To the residue was added ethyl acetate (900 ml), and the mixture was washed with water (50 ml) three times. The ethyl acetate layer was dried over anhydrous magnesium suflate, then the solvent was distilled off. To the residue were added ethyl acetate (50 ml) and ethyl ether (100 ml). Precipitating crystals were collected by filtration to afford pure (99% purity) (2RS,3RS)-2-(2,4-difluorophenyl)-1-(1H-1,2,4-triazol-1-yl)-2,3-butanediol (29.0 g) as diastereomer, m.p. 154°–156° C.

$^1$H-NMR (CDCl$_3$) δ: 0.93(3H,d,J=6.2 Hz), 4.26~4.39(1H,m), 4.82(2H,s), 6.71–6.83(2H,m), 7.35~7.51(1H,m), 7.84(1H,s), 7.87(1H,s) Elemental Analysis for C$_{12}$H$_{13}$F$_2$N$_3$O$_2$: Calcd.: C, 53.53; H, 4.87; N, 15.61 Found: C, 53.35; H, 4.90; N, 15.49.

Reference Example 25

In a mixture of ethyl acetate (200 ml) and methylene chloride (50 ml) was dissolved (2RS,3RS)-2-(2,4-difluorophenyl)-1-(1H-1,2,4-traizol-1-yl)-2,3-butanediol (11 g), to which was added, under ice-cooling, triethylamine (6.21 ml). To the resultant mixture was added dropwise methanesulfonyl chloride (3.46 ml) with stirring under ice-cooling during 3 minutes, followed by stirring for 45 minutes at room temperature. To the reaction mixture was added water (100 ml), then the organic layer was separated, washed with water and dried (anhydrous magnesium sulfate), followed by distilling off the solvent under reduced pressure to afford (2RS,3RS)-2-(2,4-difluorophenyl)-3-methanesulfonyloxy-1-(1H-1,2,4-triazol-1-yl)-2-butanol as an oily product. This product was dissolved in methanol (200 ml), to which was added under ice-cooling a 28% sodium methylate methanol solution (8.84 g), followed by stirring for 30 minutes at room temperature. The solvent was distilled off under reduced pressure. To the residue were added ethyl acetate (200 ml) and water (100 ml) for extraction. The ethyl acetate layer was washed with water and dried over anhydrous magnesium sulfate, followed by distilling off the solvent. The residue was purified by means of a silica gel column chromatography (ethyl acetate:methylene chloride=4:1), followed by crystallization from hexane to afford (2RS,3SR)-2-(2,4-difluorophenyl)-3-methyl-2-(1H-1,2,4-triazol-1-yl)methyloxirane (8.3 g), a single diastereomer, as colorless crystals, m.p. 66°–68° C.

$^1$H-NMR (CDCl$_3$) δ: 1.65(3H,d,J=5.6 Hz), 3.20(1H,q,J=5.6 Hz), 4.42(1H,d,J=14.6 Hz), 4.89(1H,d,J=14.6 Hz), 6.68~6.83(2H,m), 6.93~7.08(1H,m), 7.82(1H,s), 7.97(1H,s) Elemental Analysis for C$_{12}$H$_{11}$F$_2$N$_3$O: Calcd.: C, 57.37; H, 4.41; N, 16.73 Found: C, 57.31; H, 4.44; N, 16.62.

Reference Example 26

In dichloromethane (200 ml) was dissolved (S)-(-)-ethyl lactate (35.4 g), to which was added, under ice-cooling, p-toluenesulfonic acid.hydrate (570 mg). To the mixture was added dropwise 3,4-dihyro-2H-pyran (30.2 g), taking 30 minutes, followed by stirring for one hour under ice-cooling. To the reaction mixture was added a 5% aqueous solution of sodium hydrogen carbonate (50 ml), which was vigorously stirred, then the organic layer was separated. The organic layer was further washed with a 5% aqueous solution of sodium hydrogen carbonate and dried over anhydrous magnesium sulfate, then the solvent was distilled off under reduced pressure to afford ethyl(2S)-2-(3,4,5,6-tetrahydro-2H-pyran-2-yloxy)propionate (61 g) as a pale yellow oily product.

$^1$H-NMR (CDCl$_3$) δ: 1.28(3H,t,J=7.0 Hz), 1.40, 1.46(3H,d,J=6.8 Hz), 1.40~2.00(6H,m), 3.40~3.60(2H,m), 3.80~4.00(2H,m), 4.10~4.44(3H,m), 4.68~4.76(1H,m)

Reference Example 27

In ethanol (450 ml) was dissolved ethyl(2S)-2-(3,4,5,6-tetrahydro-2H-pyran-2-yloxy)propionate, to which was added, under ice-cooling, 2N sodium hydroxide solution (150 ml), and the mixture was stirred for one hour at room temperature. The reaction mixture was cooled with ice, to which was added a 27° C. aqueous solution of acetic acid (100 ml), followed by extraction with dichloromethane (200 ml) three times. Dichloromethane layers were combined and washed with a saturated aqueous saline solution (100 ml) twice, followed by drying over anhydrous magnesium sulfate. The solvent was distilled off under reduced pressure to leave (2S)-2-(3,4,5,6-tetrahydro-2H-pyran-2-yloxy)propionic acid (29.5 g) as a colorless waxy product.

To (2S)-2-(3,4,5,6-tetrahydro-2H-pyran-2-yloxy)propionic acid (29.5 g) was added anhydrous tetrahydrofuran (250 ml). To the mixture was added, with stirring at room temperature, 1,1-carbonyldiimidazole (33.1 g), taking 10 minutes. The mixture was stirred for 30 minutes at room temperature and cooled with ice, to which was added dropwise morpholine (34.8 g) during 15 minutes. The resultant mixture was stirred for 15 minutes on an ice bath, then the reaction mixture was concentrated under reduced pressure. The concentrate was dissolved in dichloromethane (300 ml), which was washed with a saturated aqueous sodium chloride solution (50 ml) and dried over anhydrous magnesium sulfate, followed by distilling off the solvent. The residue was purified by means of a silica gel chromatography (eluent:hexane:ethyl acetate=1:4) to afford N-[(2S)-2-(3,4,5,6-tetrahydro-2H-pyran-2-yloxy)propionyl]morpholine (17.5 g).

$^1$H-NMR (CDCl$_3$) δ: 1.39, 1.44(3H,d,J=6.8 Hz), 1.45~1.96(6H,m), 3.40~3.95(10H,m), 4.52, 4.68(1H,q,J=6.8 Hz), 4.60(1H,m) IR (film): 2945, 2855, 1662, 1650, 1460, 1435 1370, 1270, 1230, 1110, 1020, 980 cm$^{-1}$

Reference Example 28

In anhydrous tetrahydrofuran (40 ml) was dissolved 1-bromo-2,4-difluorobenzene (7.72 g). To the solution were added, at room temperature, magnesium (flakes, 972 mg) and a very small amount of iodine, and the mixture was vigorously stirred for about two hours to give a 1M solution of 2,4-difluorophenyl magnesium bromide. From this solution, a 9.5 ml portion was taken and diluted with 9.5 ml of anhydrous tetrahydrofuran, which was added dropwise to an anhydrous tetrahydrofuran solution (25 ml) of N-[(2S)-2-(3,4,5,6-tetrahydro-2H-pyran-2-yloxy)propionyl]morpholine (2.26 g) at a temperature from −30° C. to −20° C. during 25 minutes. After completion of the dropwise addition, the temperature of the mixture was raised to 20° C. during one hour. The mixture was stirred at 20° C. for further two hours. The reaction mixture was cooled with ice, to which was added a saturated aqueous solution of ammonium chloride (20 ml), followed by extraction with ethyl acetate (100 ml). The extract was dried over magnesium sulfate, then the solvent was distilled off under reduced pressure. The residue was purified by means of a silica gel chromatography (eluent, hexane:ethyl acetate=10:1) to give (2S)-2',4'-difluoro-2-(3,4,5,6-tetrahydro-2H-pyran-2-yloxy)propiophenone (1.02 g) as a pale yellow oily product.

IR (film): 3075, 2950, 2875, 1695, 1605, 1500, 1422, 1370, 1265, 1230, 1132, 1090, 1030, 970, 848 cm$^{-1}$ The optical purity of this compound was measured by the following method.

In ethanol (3 ml) was dissolved (2S)-2',4'-difluoro-2-(3,4,5,6-tetrahydro-2H-pyran-2-yloxy)propiophenone (95 mg), to which was added pyridinium p-toluenesulfonate (21 mg), followed by stirring for one hour at 55° C. The solvent was distilled off under reduced pressure, and the residue was dissolved in ethyl acetate (20 ml), which was dried over anhydrous magnesium sulfate, followed by distilling off the solvent. The residue was purified by means of a silica gel chromatography (eluent, hexane:ethyl acetate=5:1) to give (2S)-2',4'-difluoro-2-hydroxypropiophenone (40 mg) as a pale yellow oily product.

This product was subjected to analysis by means of a high performance liquid chromatography (mobile phase, hexane:isopropyl alcohol=9:1) using an optical isomer separating column [CHIRALCEL® OF 0.46 cm×25 cm, manufactured by Daicel Chemical Industries, Ltd.]. The enantiomer excess (ee) was proved to be 98.4%.

$^1$H-NMR (CDCl$_3$) δ: 1.41(3H,dd,J=7.0 Hz,J=1.6 Hz), 3.74(1H,d), 5.01(1H,m), 6.86~7.08(2H,m), 7.96~8.08(1H,m) IR (film): 3450, 1690, 1612, 1500, 1430, 1270, 1145, 1100, 1030, 980, 858 cm$^{-1}$ Reference Example 29

To dimethyl sulfoxide (5 ml) was added 60% sodium hydride in oil (85 mg), to which was added trimethyl sulfoxonium iodide (0.49 g) with stirring at about 15° C., and the mixture was stirred for 15 minutes at room temperature. The reaction mixture was cooled with ice, to which was added a dimethyl sulfoxide solution (1.2 ml) of (2S)-2',4'-difluoro-2-(3,4,5,6-tetrahydro- 2H-pyran-2-yloxy)propiophenone (0.50 g), and the mixture was stirred for two hours at room temperature. To the reaction mixture were added water (10 ml) and ethyl acetate (50 ml), and the resultant mixture was shaken. The organic layer was washed with a saturated aqueous sodium chloride solution (10 ml) twice, which was dried over anhydrous magnesium sulfate. The solvent was distilled off under reduced pressure, and the residue was purified by means of a silica gel chromatography (eluent, hexane:ethyl acetate=10:1) to afford 2-[(1S)-1-(3,4,5,6-tetrahydro-2H-pyran-2-yloxy)ethyl]-2-(2,4-difluorophenyl)oxirane (0.40 g) as a pale yellow oily product.

$^1$H-NMR (CDCl$_3$) δ: 1.10~1.26(3H,m), 1.40~1.95(6H,m), 2.83(1H,m), 3.05, 3.32(1H,d,J=5.2 Hz), 3.42~3.59(1H,m), 3.76~4.12(2H,m), 4.74~4.96(1H,m), 6.72~6.95(2H,m), 7.32~7.60(1H,m)

Reference Example 30

In dimethylformamide (5 ml) was dispersed 60% sodium hydride in oil (0.23 g), to which was added triazole (0.59 g) under ice-cooling, followed by stirring for 15 minutes. To the resultant mixture was added a dimethylformamide solution (1 ml) of 2-[(1S)-1-(3,4,5,6-tetrahydro-2H-pyran-2-yloxy)ethyl]-2-(2,4-difluorophenyl)oxirane (0.40 g), which was heated for three hours at 80° C. The reaction mixture was cooled, after which were added cold water (1.0 ml) and ethyl aceate (50 ml), and the mixture was shaken. The aqueous layer was subjected to extraction with ethyl acetate twice. Ethyl acetate layers were combined, washed with a saturated aqueous sodium chloride solution and dried over anhydrous sodium sulfate, followed by distilling off the solvent under reduced pressure. The residue was purified by means of a silica gel chromatography (eluent, dichloromethane:ethyl acetate:acetone=6:1:1). The resultant waxy product was further subjected to reprecipitation twice from ethyl acetate-hexane to afford (3S)-2-(2,4-difluorophenyl)-3-(3,4,5,6-tetrahydro-2H-pyran-2-yloxy)-1-(1H-1,2,4-triazol-1-yl)-2-butanol (0.22 g) as a colorless waxy product.

$^1$H-NMR (CDCl$_3$) δ: 0.99, 1.12(3H,d,J=6.4 Hz), 1.40~2.00(6H,m), 3.40~3.65(1H,m), 3.80~4.06(1H,m), 4.25~4.45(1H,m), 4.31(1H,s), 4.63(1H,d,J=14.2 Hz), 4.71(1H,m), 4.90(1H,d,J=14.2 Hz), 6.65~6.85(2H,m), 7.35~7.50(1H,m), 7.72, 7.73(1H,s), 7.93, 7.96(1H,s)

Reference Example 31

In ethanol (4 ml) were dissolved (3S)-2-(2,4-difluorophenyl)-3-(3,4,5,6-tetrahydro-2H-pyran-2-yl)oxy-1-(1H-1,2,4-triazol-1-yl)-2-butanol (0.22 g) and pyridinium p-toluenesulfonate (47 mg), which was stirred for two hours at 55° C. To the solution was further added pyridinium p-toluenesulfonate (10 mg), which was stirred for further two hours at 55° C. The reaction mixture was cooled, then the solvent was distilled off. To the residue was added ethyl acetate (30 ml), which was washed with a saturated aqueous sodium chloride solution (10 ml). The ethyl acetate layer was dried over anhydrous magnesium sulfate, then the solvent was distilled off under reduced pressure. To the residue was added ethyl ether, then precipitating crystals were collected by filtration to obtain (2S,3S)-2-(2,4-difluorophenyl)-1-(1H-1,2,4-triazol-1-yl)-2,3-butanediol (60 mg). m.p. 115°–117° C.

$^1$H-NMR (CDCl$_3$) δ: 0.97(3H,d,J=6.4 Hz), 4.32(1H,m), 4.82(2H,s), 6.69~6.82(2H,m), 7.35~7.48(1H,m), 7.83(1H,s), 7.84(1H,s)

Reference Example 32

In a mixture of ethyl acetate (2 ml) and dichloromethane (0.5 ml) was dissolved (2S,3S)-2-(2,4-difluorophenyl)-1-(1H-1,2,4-triazol-1-yl)-2,3-butanediol (58 mg). To the solution were added, under ice-cooling, triethylamine (66 μl) and methanesulfonyl chloride (37 μl). The mixture was stirred for two hours at room temperature. To the reaction mixture was added ethyl acetate (30 ml), which was washed with water, dried (anhydrous magnesium sulfate) and concentrated to afford (2S,3S)-2-(2,4-difluorophenyl)-3-methanesulfonyloxy-1-(1H -1,2,4-triazol-1-yl)-2-butanol as an oily product . This product was dissolved in methanol (2 ml), to which was added, under ice-cooling, 28% sodium methyl ate (116 μl), and the mixture was stirred for 30 minutes at room temperature. To the reaction mixture was added dichloromethane (30 ml), which was washed with water and dried (anhydrous magnesium sulfate), followed by distilling off the solvent under reduced pressure. The residue was purified by means of a silica gel chromatography (eluent: ethyl acetate-dichloromethane=4:1), followed by crystallization from hexane to afford (2S,3R)-2-(2,4-difluorophenyl)-3-methyl-2-(1H-1,2,4-triazol-1-yl)methyl oxirane (42 mg) as colorless needles. m.p. 89°–90° C. $[\alpha]_D^{23}=+7.8°$ (c=1.0 in MeOH)

$^1$H-NMR (CDCl$_3$) δ: 1.65(3H,d,J=5.6 Hz), 3.20(1H,q,J=5.6 Hz), 4.43(1H,d,J=14.6 Hz), 4.88(1H,d,J=14.6 Hz), 6.68~6.83(2H,m), 6.93~7.08(1H,m), 7.82(1H,s), 7.96(1H,s) Elemental Analysis for C$_{12}$H$_{11}$F$_2$N$_3$O: Calcd.: C, 57.37; H, 4.41; N, 16.73 Found: C, 56.98; H, 4.40; N, 16.53.

This product was subjected to analysis by means of a high performance liquid chromatography (mobile phase:hexane-isopropanol=9:1) using an optical isomer separating column [CHIRALCEL ® OF 0.46 cm×25 cm, manufactured by Daicel Chemical Industries, Ltd.]. The enantiomer excess was proved to be 97.9%.

Reference Example 33

Methyl (R)-(+)-lactate (25.0 g) was dissolved in dichloromethane (250 ml), to which was added, under ice-cooling, p-toluenesulfonic acid.hydrate (456 mg). To the mixture was then added dropwise 3,4-dihydro-2H-pyran (24.2 g) during 30 minutes, which was stirred for one hour under ice-cooling. To the reaction mixture was added a 5% aqueous solution of sodium hydrogen carbonate (50 ml), and the mixture was stirred vigorously, followed by separating the organic layer. The organic layer was further washed with a 5% aqueous solution of sodium hydrogen carbonate, which was dried over anhydrous magnesium sulfate, followed by distilling off the solvent under reduced pressure to leave methyl (2R)-2-(3,4,5,6-tetrahydro-2H-pyran-2-yloxy)-propionate (42.7 g) as a pale yellow oily product.

Reference Example 34

In ethanol (510 ml) was dissolved methyl (2R)-2-(3,4,5,6-tetrahydro-2H-pyran-2-yloxy)propionate (42.7 g), to which was added, under ice-cooling, a 2N solution of sodium hydroxide (170 ml), followed by stirring for one hour at room temperature. The reaction mixture was cooled with ice, to which was added a 26% aqueous solution of acetic acid (120 ml), followed by extraction with dichloromethane (200 ml) three times. Dichloromethane layers were combined, washed with a saturated aqueous sodium chloride solution (100 ml) twice, and dried over anhydrous magnesium sulfate, followed by distilling off the solvent under reduced pressure to leave (2R)-2-(3,4,5,6-tetrahydro-2H-pyran-2-yloxy)propionic acid (32 g) as a colorless waxy product.

Anhydrous tetrahydrofuran (250 ml) was added to (2R)-2-(3,4,5,6-tetrahydro-2H-pyran-2-yloxy)propionic acid (32 g). To the mixture was added by portions 1,1'-carbonyl-diimidazole (35.8 g), with stirring at room temperature during 10 minutes. The resultant mixture was stirred for 30 minutes at room temperature and, then, cooled with ice, to which was added dropwise morpholine (38.3 g) during 15 mintues, followed by stirring for 15 minutes in an ice-bath. The reaction mixture was concentrated under reduced pressure, and the concentrate was dissolved in dichloromethane (300 ml). The solution was washed with a saturated aqueous solution of sodium chloride (50 ml) and dried over anhydrous magnesium sulfate, followed by distilling off the solvent. The residue was purified by means of a silica gel chromatography (eluent: hexane-ethyl acetate=1:4) to afford N-[(2R)-2-(3,4,5,6-tetrahydro-2H-pyran-2-yloxy)propionyl]morpholine (25.7 g).

$^1$H-NMR (CDCl$_3$) δ: 1.39, 1.44(3H,d,J=6.8 Hz), 1.45~1.96(6H,m), 3.40~3.95(10H,m), 4.52, 4.68(1H,q,J=6.8 Hz), 4.59~4.65(1H,m) IR (film): 2945, 2855, 1662, 1650, 1462, 1438, 1370, 1270, 1230, 1112, 1030, 980cm$^{-1}$ Reference Example 35

In anhydrous tetrahydrofuran (50 ml) was dissolved 1-bromo-2,4-difluorobenzene (9.69 g). To the solution were added, at room temperature, magnesium (turnings, 1.22 g) and a small amount of iodine, and the mixture was stirred vigorously for about two hours to give a 1M solution of 2,4-difluorophenyl magnesium bromide. This solution was diluted with 50 ml of anhydrous tetrahydrofuran, which was added dropwise to an anhydrous tetrahydrofuran solution (125 ml) of N-[(2R)-2-(3,4,5,6-tetrahydro-2H-pyran-2-yloxy)propionyl]morpholine (12.7 g) at the temperature from −30° C. to −20° C. during 45 minutes. After completion of the addition, the temperature of the mixture was raised to 20° C. during one hour. The mixture was stirred for one further hour at 20° C. The reaction mixture was cooled with ice, to which was added a saturated aqueous solution of ammonium chloride (40 ml), followed by extraction with ethyl acetate (300 ml). The extract was dried over magnesium sulfate, then the solvent was distilled off under reduced pressure. The residue was purified by means of a silica gel chromatography (eluent: hexane-ethyl acetate=10:1) to afford (2R)-2',4'-difluoro-2-(3,4,5,6-tetrahydro-2H-pyran-2-yloxy)propiophenone (5.03 g) as a pale yellow oily product.

IR (film): 3075, 2950, 2875, 1695, 1605, 1500, 1422, 1370, 1266, 1235, 1138, 1090, 1030, 970, 850cm$^{-1}$ The optical purity of this compound was measured by the following method.

In ethanol (3 ml) was dissolved (2R)-2',4'-difluoro-2-(3,4,5,6-tetrahydro-2H-pyran-2-yloxy)propiophenone (121 mg), to which was added pyridinium p-toluenesulfonate (25 mg), and the mixture was stirred for one hour at 55° C. The solvent was distilled off under reduced pressure, and the residue was dissolved in ethyl acetate (20 ml). The solution was washed with water and dried over anhydrous magnesium sulfate, followed by distilling off the solvent. The residue was purified by means of a silica gel chromatography (eluent: hexane-ethyl acetate=5:1) to give (2R)-2',4'-difluoro-2-hydroxy-propiophenone (62 mg) as a pale yellow oily product. [α]$_D$+68.7 (c=1.8 in chloroform)

This product was subjected to analysis by means of a high performance liquid chromatography (mobile phase:hexane-isopropanol=9:1) using an optical isomer separating column [CHIRALCEL ® OF 0.46 cm×25 cm, manufactured by Daicel Chemical Industries, Ltd.]. The enantiomer with (2S)-configuration was not detected.

$^1$H-NMR (CDCl$_3$) δ: 1.41(3H,dd,J=7.0 Hz,J=1.6 Hz), 3.74(1H,d,J=7.0 Hz), 5.01(1H,m), 6.86~7.08(2H,m), 7.96~8.08(1H,m) IR (film): 3450, 1690, 1610, 1500, 1430, 1268, 1140, 1095, 1030, 980, 855 cm$^{-1}$ Reference Example 36

To dimethyl sulfoxide (50 ml) was added 60% sodium hydride (0.833 g) in mineral oil. While stirring the mixture at about 15° C., trimethylsulfoxonium iodide (4.80 g) was added thereto, which was stirred for 15 minutes at room temperature. The reaction mixture was cooled with ice, to which was added a dimethyl sulfoxide solution (10 ml) of (2R)-2',4'-difluoro-2-(3,4,5,6-tetrahydro-2H-pyran-2-yloxy)propiophenone (4.90 g). The resultant mixture was stirred for two hours at room temperature. The reaction mixture was poured into ice-water (120 ml), followed by extraction with ethyl acetate (150 ml, 100 ml, 100ml). Ethyl acetate layers were combined and washed with water (50 ml) and a saturated aqueous solution of sodium chloride (50 ml), followed by drying over anhydrous magnesium sulfate. The solvent was distilled off under reduced pressure, and the residue was purified by means of a silica gel chromatography (eluent: hexane-ethyl acetate=10:1) to afford 2-[(1R)-1-(3,4,5,6-tetrahydro-2H-pyran-2-yloxy)ethyl]-2-(2,4-difluorophenyl)oxirane (4.70 g) as a pale yellow oily product.

$^1$H-NMR (CDCl$_3$) δ: 1.10~1.30(3H,m), 1.40~1.95(6H,m), 2.83(1H,m), 3.05, 3.32(1H,d,J=5.2 Hz), 3.42~3.60(1H,m), 3.76~4.14(2H,m), 4.76, 4.93(1H,m), 6.72~6.95(2H,m), 7.32~7.60(1H,m) IR (film): 2950, 1618, 1600, 1510, 1425, 1270, 1140, 1120, 1075, 1020, 990, 985, 850cm$^{-1}$

Reference Example 37

In dimethylformamide (50 ml) was dispersed 60% sodium hydride (2.64 g) in mineral oil, to which was added, under ice-cooling, triazole (6.84 g), and the mixture was stirred for 15 minutes. To the mixture was added a dimethylformamide solution (10 ml) of 2-[(1R)-1-(3,4,5,6-tetrahydro-2H-pyran-2-yloxy)ethyl]-2-(2,4-difluorophenyl)oxirane (4.7 g). The resultant mixture was heated for 3 hours at 80° C. The reaction mixture was cooled, which was then poured into cold water (200 ml), followed by extraction with ethyl acetate (150 ml) three times. Ethyl acetate layers were combined, washed with water (100 ml×3) and a saturated aqueous solution (100 ml) of sodium chloride successively, and dried over anhydrous sodium sulfate, followed by distilling off the solvent. The residue was purified by means of a silica gel chromatography (eluent: dichloromethane-ethyl acetate-acetone=6:1:1) to afford (3R)-2-(2,4-difluorophenyl)-3-(3,4,5,6-tetrahydro-2H-pyran-2-yloxy)-1-(1H-1,2,4-triazol-1-yl)-2-butanol (4.4 g) as a colorless viscous oil.

$^1$H-NMR (CDCl$_3$) δ: 0.99, 1.12(3H,d,J=6.4 Hz), 1.40~2.00(6H,m), 3.40~3.65(1H,m), 3.80~4.06(1H,m), 4.25~4.45(1H,m), 4.29(1H,s), 4.62(1H,d,J=14.2 Hz), 4.71(1H,m), 4.90(1H,d,J=14.2 Hz), 6.65~6.83(2H,m), 7.35~7.50(1H,m), 7.71, 7.72(1H,s), 7.91, 7.94(1H,s)

Reference Example 38

In ethanol (50 ml) were dissolved (3R)-2-(2,4-difluorophenyl)-3-(3,4,5,6-tetrahydro-2H-pyran-2-yl)oxy-1-(1H-1,2,4-triazol-1-yl)-2-butanol (4.4 g) and pyridinium p-toluenesulfonate (0.93 g). The solution was stirred for two hours at 55° C. to which was further added pyridinium p-toluenesulfonate (0.20 g), followed by stirring for further two hours at 55° C. The reaction mixture was cooled, then the solvent was distilled off. To the residue was added ethyl acetate (250 ml), which was washed with water (50 ml) and a saturated aqueous solution of sodium chloride (50 ml) successively. The ethyl acetate layer was dried over anhydrous magnesium sulfate, then the solvent was distilled off under reduced pressure. To the residue was added ethyl ether, then precipitating crystals were collected by filtration to give (2R,3R)-2-(2,4-difluorophenyl)-1-(1H-1,2,4-triazol-1-yl)-2,3-butanediol (1.37 g). m.p. 115°-117° C. [α]$_D$=−80.3° C. (c=1.0 in methanol)

$^1$H-NMR (CDCl$_3$) δ: 0.97(3H,d,J=6.4 Hz), 4.33(1H,m), 4.82(2H,s), 6.69~6.82(2H,m), 7.35~7.48(1H,m), 7.84(1H,s), 7.85(1H,s)

Reference Example 39

In a mixture of ethyl acetate (40 ml) and dichloromethane (10 ml) was dissolved (2R,3R)-2-(2,4-difluorophenyl)-1-(1H-1,2,4-triazol-1-yl)-2,3-butanediol (1.25 g). To the solution were added, under ice-cooling, triethylamine (0.84 ml) and methanesulfonyl chloride (0.48 ml), which was stirred for 30 minutes at room temperature. To the reaction mixture was added ethyl acetate (50 ml), which was washed with water, dried (anhydrous magnesium sulfate) and concentrated to give (2R,3R)-2-(2,4-difluorophenyl)-3-methanesulfonyloxy-1-(1H-1,2,4-triazol-1-yl)-2-butanol as an oily product. The product was dissolved in methanol (40 ml), to which was added a 28% methanol solution of sodium methylate (1.16 ml) under ice-cooling. The mixture was stirred for 30 minutes at room temperature. The reaction mixture was concentrated under reduced pressure to a volume of about 10 ml. To the concentrate was added ethyl acetate (100 ml), and the mixture was washed with water, then dried (anhydrous magnesium sulfate), followed by distilling off the solvent under reduced pressure. The residue was purified by means of a silica gel chromatography (eluent: ethyl acetate-dichloromethane=4:1), which was then recrystallized from a mixture of ethyl acetate and hexane to afford (2R,3S)-2-(2,4-difluorophenyl)-3-methyl-2-[(1H-1,2,4-triazol-1-yl)methyl]oxirane (520 mg) as colorless needles. m.p. 89°-90° C. [α]$_D^{23}$=−8.3° (c=1.0 in MeOH)

$^1$H-NMR (CDCl$_3$) δ: 1.65(3H,d,J=5.6 Hz), 3.20(1H,q,J=5.6 Hz), 4.43(1H,d,J=14.6 Hz), 4.88(1H,d,J=14.6 Hz), 6.68~6.83(2H,m), 6.93~7.08(1H,m), 7.82(1H,s), 7.97(1H,s) Elemental Analysis for C$_{12}$H$_{11}$F$_2$N$_3$O: Calcd.: C, 57.37; H, 4.41; N, 16.73 Found: C, 57.27; H, 4.43; N, 16.83.

This product was subjected to analysis by means of a high performance liquid chromatography (mobile phase: hexane-isopropyl alcohol=9:1) using an optical isomer separating column [CHIRALCEL® OF 0.46 cm×25 cm, manufactured by Daicel Chemical Industries, Ltd.]The enantiomer excess was proved to be 99.2%.

Reference Example 40

A mixture of methyl (R)-lactate (104 g) and morpholine (260 ml) was heated for 60 hours at 85° C. The reaction mixture was concentrated under reduced pressure, and the concentrate was purified by means of a silica gel chromatography (silica gel 800 g, eluent: hexane-ethyl acetate=1:1→etyl acetate) to give N-[(2R)-2-hydroxypropionyl]morpholine (141 g) as a pale yellow oily product.

$^1$H-NMR (CDCl$_3$) δ: 1.34(3H,d,J=6.6 Hz), 3.43(2H,t,J=4.8 Hz), 3.55-3.80(6H,m), 3.79(1H,d), 4.45(1H,m) [α]$_D$=+0.98° (c=5.24 in CHCl$_3$)

Reference Example 41

To a dichloromethane (500 ml) solution of N-[(2R)-2-hydroxypropionyl]morpholine (141 g) was added p-toluenesulfonic acid mono hydrate (1.67 g). To the mixture was added dropwise (30 minutes) 3,4-dihydro-2H-pyran (89.3 g) under ice-cooling, which was stirred for 30 minutes at room temperature. The reaction mixture was washed with a 5% aqueous solution of sodium hydrogen carbonate (150 ml×2), which was dried (magnesium sulfate), then the solvent was distilled off under reduced pressure. The residue was purified by means of a silica gel chromatography [silica gel 800 g, eluent:

hexane-ethyl acetate=8:1→ethyl acetate] to give N-[(2R)-2-(3,4,5,6-tetrahydro-2H-pyran-2-yloxy)propionyl]morpholine (184 g) as a pale yellow oily product.

$^1$H-NMR (CDCl$_3$) δ: 1.39, 1.44(3H,d,J=6.8 Hz), 1.40–1.95(6H,m), 3.40–3.95(10H,m), 4.48–4.75(2H,m) [α]$_D$=+34.9° (c=6.3 in CHCl$_3$)

Reference Example 42

The mother liquor, which was left when (2RS,3RS)-2-(2,4-difluorophenyl)-1-(1H-1,2,4-triazol-1-yl)-2,3-butanediol was obtained by recrystallization in Reference Example 24, was subjected to distillation under reduced pressure. The residue was purified by means of a silica gel column chromatography (ethyl acetate:methanol=30:1) to afford (2RS,3SR)-2-(2,4-difluorophenyl)-1-(1H-1,2,4-triazol-1-yl)-2,3-butanediol as the first fraction of eluate, which was recrystallized from methanol to give colorless prisms (1.9 g) of 98% purity as diastereomer. m.p. 146°–148° C.

$^1$H-NMR (CDCl$_3$) δ: 1.26(3H,d,J=5.8 Hz), 2.41~2.52(1H,m), 3.92~4.07(1H,m), 4.57(1H,d,J=14 Hz), 5.03(1H,s), 5.04(1H,d,J=14 Hz), 6.68~6.87(2H,m), 7.50~7.68(1H,m), 7.79(1H,s), 8.05(1H,s) Elemental Analysis for C$_{12}$H$_{13}$F$_2$O$_2$: Calcd.: C, 55.53; H, 4.87; N, 15.61 Found: C, 53.70; H, 4.97; N, 15.59.

Reference Example 43

In a manner like that described in Reference Example 25, (2RS,3SR)-2-(2,4-difluorophenyl)-1-(1H-1,2,4-triazol-1-yl)-2,3-butanediol (1.1 g) obtained in Reference Example 42 was allowed to react with methanesulfonyl chloride (0.35 ml), followed by treatment with a 28% sodium methylate methanol solution to afford (2RS,3RS)-2-(2,4-difluorophenyl)-3-methyl-2-(1H-1,2,4-triazol-1-yl)methyl oxirane. The product was purified by means of a silica gel column chromatography (ethyl acetate: methylene chloride=4:1) to give a yellow oily product (0.8 g).

$^1$H-NMR (CDCl$_3$) δ: 1.06(3H,d,J=5.4 Hz), 3.18(1H,q,J=5.4, 10.7 Hz), 4.42(1H,d,J=15. Hz), 4.81(1H,d,J=15 Hz), 6.76~6.92(2H,m), 7.07~7.20(1H,m), 7.86(1H,s), 8.07(1H,s)

Reference Examples 44–50

By the same manner as in Reference Example 12, imidazole-2-carboxyaldehyde was allowed to react with the alkylating agent shown in Table 8 (Step 1), then the product was subjected, without purification, to the reduction with sodium borohydride (Step 2), followed by chlorination with thionyl chloride (Step 3) to give a 2-chloromethyl imidazole derivative (Table 8).

TABLE 8

| Ref. Ex. No. | Starting Material | Product |
|---|---|---|
| 44 | Step 1<br>Imidazole-2-carboxyaldehyde (2.0 g)<br>Ethyl iodide (2.5 ml)<br>Step 2<br>Sodium borohydride (0.23 g)<br>Step 3<br>1-Ethylimidazole-2-methanol (0.80 g)<br>Thionylchloride (8.0 ml) | 1-Ethylimidazole-2-methanol (1.6 g)<br>mp. 80–83° C. (colorless plates)<br>$^1$H-NMR(CDCl$_3$)δ:<br>1.44(3H, t, J=7.4Hz),<br>4.07(2H, q, J=7.4Hz),<br>4.63(2H, s), 6.30(1H, br.s),<br>6.85(2H, s)<br>2-Chloromethyl-1-ethylimidazole hydrochloride (1.1 g)<br>mp. 130–135° C. (colorless plates)<br>$^1$H-NMR(DMSO-d$_6$)δ:<br>1.44(3H, t, J=7.0Hz),<br>4.27(2H, q, J=7.0Hz),<br>5.26(2H, s),<br>7.70(1H, d, J=1.8Hz),<br>7.92(1H, d, J=1.8Hz) |
| 45 | Step 1<br>Imidazole-2-carboxyaldehyde (2.0 g)<br>Isopropyl iodide (3.1 ml)<br>Step 2<br>Sodium borohydride (0.23 g)<br>Step 3<br>1-Isopropyl-imidazole-2-methanol (0.80 g)<br>Thionylchloride (8.0 ml) | 1-Isopropylimidazole-2-methanol (1.6 g)<br>mp. 85–87° C. (colorless plates)<br>$^1$H-NMR(CDCl$_3$)δ:<br>1.45(6H, d, J=6.6Hz),<br>4.65(1H, sep., J=6.6Hz),<br>4.65(2H, s), 6.40(1H, br.s)<br>6.85(1H, d, J=1.2Hz),<br>6.91(1H, s)<br>2-Chloromethyl-1-isopropylimidazole hydrochloride (1.1 g)<br>mp. 124–130° C. (colorless plates)<br>$^1$H-NMR(DMSO-d$_6$)δ:<br>1.49(6H, d, 6.6Hz),<br>4.82(1H, sep., 6.6Hz),<br>5.28(2H, s),<br>7.81(1H, d, J=2.0Hz),<br>8.08(1H, d, J=2.0Hz), |
| 46 | Step 1<br>Imidazole-2-carboxyaldehyde (2.0 g)<br>2-Fluoroethyl-p-toluenesulfonate (5.5 g)<br>Step 2<br>Sodium borohydride (0.20 g)<br>Step 3<br>1-(2-Fluoroethyl)-imidazole-2-methanol (0.40 g)<br>Thionylchloride (3.0 ml) | 1-(2-Fluoroethyl)-imidazole-2-methanol (1.4 g)<br>mp. 65–66° C. (colorless prisms)<br>$^1$H-NMR(CDCl$_3$)δ: 4.25–4.86(4H, m), 4.65(2H, s), 5.70(1H, br.s),<br>6.86(1H, d, J=1.4Hz),<br>6.95(1H, d, J=1.4Hz)<br>2-Chloromethyl-1-(2-fluoroethyl)imidazole hydrochloride (0.44 g)<br>mp. 146–147° C. (in sealed tube) (colorless needles)<br>$^1$H-NMR(DMSO-d$_6$)δ: 4.56–4.98(4H, m), 5.23(2H, s),<br>7.79(1H, d, J=2.0Hz),<br>7.83(1H, s) |
| 47 | Step 1<br>Imidazole-2-carboxyaldehyde (2.0 g)<br>2,2,2-Trifluoroethyl p-toluenesulfonate (5.8 g)<br>Step 2<br>Sodium borohydride (0.23 g)<br>Step 3<br>1-(2,2,2-Trifluoroethyl)imidazole-2-methanol (0.8 g)<br>Thionylchloride (8.0 ml) | 1-(2,2,2-Trifluoroethyl)imidazole-2-methanol (1.2 g)<br>mp. 81–82° C. (colorless prisms)<br>$^1$H-NMR(CDCl$_3$)δ: 4.6–4.8(4H, m), 6.0(1H, br.s),<br>6.89(1H, d, J=1.4Hz),<br>6.94(1H, s)<br>2-(Chloromethyl)-1-(2,2,2-trifluoroethyl)imidazole hydrochloride (0.9 g)<br>mp. 163–166° C. (in sealed tube) (colorless needles)<br>$^1$H-NMR(DMSO-d$_6$)δ:<br>5.26(2H, s),<br>5.50(2H, q, J=8.8Hz),<br>7.80(1H, s), 7.84(1H, s) |
| 48 | Step 1<br>Imidazole-2-carboxyaldehyde (2.0 g)<br>Cyclopropylmethyl-bromide (3.3 g)<br>Step 2<br>Sodium borohydride (0.26 g)<br>Step 3<br>1-Cyclopropyl- | 1-Cyclopropylmethyl-imidazole-2-methanol (2.0 g)<br>mp. 76–77° C. (colorless plates)<br>$^1$H-NMR(CDCl$_3$)δ: 0.33–0.70(4H, m), 1.1–1.3(1H, m),<br>3.89(2H, d, J=7.0Hz),<br>4.63(2H, s), 6.85(1H, s),<br>6.90(1H, s), 6.98(1H, s)<br>2-Chloromethyl-1-cyclopropylmethylimidazole |

TABLE 8-continued

| Ref. Ex. No. | Starting Material | Product |
|---|---|---|
| | methylimidazole-2-methanol (0.80 g) Thionylchloride (8.0 ml) | hydrochloride (0.9 g) mp. 129–132° C. (colorless plates) $^1$H-NMR(DMSO-d$_6$)δ: 0.48–0.65(4H, m), 1.27–1.41(1H, m), 4.13(2H, d, J=7.4Hz), 5.25(2H, s), 7.78(1H, d, J=1.8Hz), 7.93(1H, d, J=1.8Hz) |
| 49 | Step 1 Imidazole-2-carboxyaldehyde (2.0 g) 2,2-Difluoroethyl p-toluenesufonate (5.9 g) Step 2 Sodium borohydride (0.3 g) Step 3 1-(2,2-Difluoroethyl)imidazole-2-methanol (0.80 g) Thionyl chloride (8.0 ml) | 1-(2,2-Difluoroethyl)imidazole-2-methanol (1.6 g) mp. 97–100° C. (colorless needles) $^1$H-NMR(DMSO-d$_6$)δ: 4.44–4.62(4H, m), 5.44(1H, t, J=5.6Hz), 6.31(1H, t, J=55.4Hz, t, J=3.2Hz), 6.82(1H, d, J=1.2Hz), 7.14(1H, s) 2-Chloromethyl-1-(2,2-difluoroethyl)imidazole hydrochloride (1.0 g) mp. 107–108° C. (colorless prisms) $^1$H-NMR(DMSO-d$_6$)δ: 4.91(2H, d, J=3.2Hz, t, J=15.4Hz), 5.25(2H, s), 6.55(1H, t, J=54Hz, t, J=3.2Hz), 7.81(1H, s), 7.82(1H, s |
| 50 | Step 1 Imidazole-2-carboxyaldehyde (1.0 g) 1,3-Difluoro-2-propyl p-toluenesufonate (2.6 g) Step 2 Sodium borohydride (0.20 g) Step 3 1-(1,3-Difluoro-2-propyl)imidazole-2-methanol (0.14 g) Thionyl chloride (0.8 ml) | 1-(1,3-Difluoro-2-propyl)imidazole-2-methanol (0.14 g): mp. 104–106° C. (colorless plates) $^1$H-NMR(CDCl$_3$)δ: 4.68(4H, s), 4.8–5.1(3H, m), 6.88(1H, d, J=1.4Hz), 7.06(1H, s) 2-Chloromethyl-1-(1,3-difluoro-2-propyl)imidazole hydrochloride (0.14 g) mp. 191–194° C. (in sealed tube) (colorless plates) $^1$H-NMR(DMSO-d$_6$)δ: 4.8–5.5(7H, m), 7.81(1H, d, J=2.0Hz), 8.00(1H, s) |

Reference Example 51

To an ethanol (100 ml) solution of 3-(p-methoxybenzylthio)propionaldehyde (5.7 g) was added a 40% aqueous solution of glyoxal (4.3 g), to which was further added a 30% aqueous solution of ammonia (4.1 ml) at −10° C. The mixture was stirred for one hour at room temperature, to which were added a 40% aqueous solution of glyoxal (4.0 ml) and a 30% aqueous solution of ammonia (4.1 ml), then the resultant mixture was stirred for further one hour. The reaction mixture was concentrated under reduced pressure. The concentrate was acidified with hydrochloric acid, which was washed with methylene chloride (30 ml×2). The aqueous layer was adjust to pH 8 with an aqueous solution of sodium hydroxide, which was subjected to extraction with methylene chloride (30 ml×3). The solution was dried over anhydrous sodium sulfate, which was concentrated under reduced pressure. To the concentrate was added a mixture of ethanol and ethyl acetate, whereupon 2-[2-(p-methoxybenzylthio)ethyl]-imidazole (2.7 g) was separated out as crystals. The mother liquor was subjected to a silica gel column chromatography (3 cm×15 cm), eluting with methanol-methylene chloride (1:9). The desired fraction was concentrated under reduced pressure to yield 1.1 g of product as crystals. m.p. 116°–118° C. (colorless plates)

$^1$H-NMR (DMSO-d$_6$) δ: 2.68(2H,t,J=7.0 Hz), 2.85(2H,t,J=7.0 Hz), 3.65(2H,s), 3.73(3H,s), 6.87(2H,d,J=8.8 Hz), 7.23(2H,d,J=8.8 Hz), 6.7~7.1(2H,br.), 11.73(1H,br.) Elemental Analysis for C$_{13}$H$_{16}$N$_2$OS: Calcd.: C, 62.87; H, 6.49; N, 11.28 Found: C, 62.86; H, 6.45; N, 11.29.

To a dimethylformamide (15 ml) solution of 2-[2-(p-methoxybenzylthio)ethyl]imidazole (1.5 g) was added 60% sodium hydride (0.29 g) in mineral oil at 0° C. To the mixture was added, 15 minutes later, methyl iodide (0.41 ml) at −20° C., followed by stirring for 10 minutes. The reaction mixture was poured into water (60 ml), which was subjected to extraction with methylene chloride (20 ml×three times). The organic layer was washed with water (20 ml), dried over anhydrous sodium sulfate, and concentrated under reduced pressure. The concentrate was subjected to a silica gel chromatography (3 cm×15 cm), eluting with methanol-methylene chloride (5:95). The desired fraction was concentrated under reduced pressure to afford 1-methyl-2-[2-(p-methoxybenzylthio)ethyl]imidazole (1.6 g) as a colorless oily product.

$^1$H-NMR (CDCl$_3$) δ: 2.8~2.95(4H,m), 3.54(3H,s), 3.65(2H,s), 3.79(3H,s), 6.78(1H,d,J=1.4 Hz), 6.54(2H,d,J=8.6 Hz), 6.94(1H,d,J=1.4 Hz), 7.24(2H,d,J=8.6 Hz)

In a mixture of trifluoroacetic acid (25 ml) and anisole (10 ml) was dissolved 1-methyl-2-[2-(p-methoxybenzylthio)ethyl]imidazole (1.4 g). To the solution was added mercury(II) acetate (1.9 g) at 0° C., and the mixture was stirred for one hour and 45 minutes. The reaction mixture was concentrated under reduced pressure. To the concentrate was added petroleum ether (50 ml). The supernatant was removed. To the precipitate was added diethyl ether (30 ml) followed by filtration to give white powder (2.6 g). This powder (1.0 g) was dissolved in N,N-dimethyl formamide (5.0 ml), into which was bubbled hydrogen sulfide for 10 minutes at 0° C. Into the reaction mixture was bubbled nitrogen to remove excess volume of hydrogen sulfide. Insoluble substances were filtered off, and the filtrate was concentrated under reduced pressure to afford 1-methyl-2-(2-mercaptoethyl)imidazole (0.5 g) as a colorless oily product.

$^1$H-NMR (DMSO-d$_6$) δ: 2.74(1H,t,J=7.0 Hz), 2.88(2H,d,J=7.0 Hz,d,J=12 Hz), 3.1~3.4(2H,m), 3.82(3H,s), 7.61(1H,d,J=2.0 Hz), 7.63(1H,d,J=2.0 Hz)

Reference Example 52

To a methanol (31 ml) solution containing a 37% aqueous solution of formaldehyde (8.9 g) and a 40% aqueous solution of glyoxal (16 g) was added, with stirring under ice-cooling, a methanol (5.0 ml) solution containing cyclopropylamine (6.3 g) and a 28% aqueous solution of ammonia (7.6 g), during 25 minutes. The resultant mixture was stirred for one hour at 0° C., which was concentrated under reduced pressure to a volume of about 10 ml. Insoluble substances were filtered off. To the filtrate was added water (200 ml). The aqueous solution was washed with hexane (100 ml×4) and then with a mixture of hexane (50 ml) and diethyl ether (30 ml). The resultant aqueous solution was saturated with sodium chloride, which was subjected to extraction with ethyl acetate (100 ml×8). The ethyl acetate layer was washed with a saturated aqueous solution of sodium chloride (50 ml), which was dried over anhydrous magnesium sulfate, followed by distilling off the solvent under reduced pressure to give crude 7-cyclopropyl imidazole (4.2 g) as colorless powder. A mixture of this crude product (3.5 g) and paraformaldehyde (3.0 g) was heated for 30 minutes at 170° C., to which was further added paraformaldehyde (2.0 g), and the mixture was heated for 20 minutes at 170° C. To the resultant mixture was further added paraformaldehyde (2.0 g), which was heated for 20 minutes at 170° C. The reaction mixture was cooled with ice and dissolved in methanol (20 ml), to which was added a saturated aqueous solution of sodium chloride (20 ml), followed by extraction with ethyl acetate (40 ml×2). The ethyl acetate layer was dried over anhydrous magnesium sulfate, followed by concentration under reduced pressure. The concentrate was subjected to a silica gel chromatography (3×15 cm), eluting with methanol-dichloromethane (1:9), then the desired fraction was concentrated under reduced pressure. To the concentrate was added a mixture of ethyl acetate and diethyl ether to yield 1-cyclopropyl-2-hydroxymethylimidazole (0.7 g) as colorless crystals. This compound (0.7 g) was added to thionyl chloride (7 ml) at 0° C., which was stirred for 5 minutes. Then the reaction mixture was refluxed for 15 minutes. Excess thionyl chloride was distilled off under reduced pressure. To the residue was added diethyl ether, and the powder was collected by filtration, which was recrystallized from a mixture of ethanol and diethyl ether to afford 1-cyclopropyl-2-chloromethylimidazole hydrochloride (0.75 g).

1-Cyclopropyl-2-hydroxymethylimidazole m.p. 90°–95° C. (colorless needles)

$^1$H-NMR (CDCl$_3$) δ: 0.9~1.2(4H,m), 3.25~3.40(1H,m), 4.76(2H,s), 5.9(1H,br.), 6.86(2H,s) Elemental Analysis for C$_7$H$_{10}$N$_2$O: Calcd.: C, 60.85; H, 7.29; N, 20.27 Found: C, 60.83; H, 7.29; N, 20.24

1-Cyclopropyl-2-chloromethylimidazole hydrochloride m.p. 100°–101° C. (colorless prisms)

$^1$H-NMR (DMSO-d$_6$) δ: 1.1~1.3(4H,m), 3.65~3.80(1H,m), 5.21(2H,s), 7.72(1H,d,J=2.0 Hz), 7.80(1H,d,J=2.0 Hz). Elemental Analysis for C$_7$H$_9$ClN$_2$.HCl: Calcd.: C, 43.55; H, 5.22; N, 14.51 Found: C, 43.61; H, 5.22; N, 14.37.

Reference Example 53

To a methanol (50 ml) solution of glycolic acid hydrazide (5.0 g) was added cyclopropyl isothiocyanate (5.5 g) at 20° C. The mixture was stirred for one hour, to which was then added water (30 ml) at 0° C. To the resultant mixture was added dropwise a 5N aqueous solution of NaOH (11 ml), the temperature of which was raised to 20° C., followed by stirring for 3 hours. The reaction mixture was concentrated under reduced pressure to make its volume about 10 ml. The concentrate was diluted with ethanol (100 ml), to which was added dropwise a 5N aqueous solution of HCl (11 ml) under ice-cooling. Insoluble substances were filtered off, and the filtrate was concentrated to dryness under reduced pressure to give crude crystals (6.4 g) of 4-cyclopropyl-5-hydroxymethyl-3-mercapto-4H-1,2,4-triazole. This compound (3.0 g) was added to a mixture of concentrated nitric acid (d=1.38) (4.6 ml), water (12 ml) and sodium nitrite (10 mg) at 60° C. Then, concentrated nitric acid (1.0 ml) was added. When a portion of nitric acid was contacted with small amount of a triazole compound on the inside wall of the reaction vessel, the reaction started and the reaction temperature reached 90° C.~100° C., then the reaction was completed. The reaction mixture was cooled with ice, neutralized with an aqueous solution of NaOH, and concentrated under reduced pressure. The concentrate was subjected to a silica gel chromatography (3×10 cm), eluting with methanol-dichloromethane (1:4). The desired fraction was concentrated to give 4-cyclopropyl-3-hydroxymethyl-4H-1,2,4-triazole (2.0 g). This product (1.0 g) was added to thionyl chloride (10 ml) at 0° C., which was refluxed for 20 minutes. The mixture was cooled, then excess volume of thionyl chloride was distilled off under reduced pressure. To the residue was added diethyl ether, and the resulting powder was collected by filtration. This product was recrystallized from a mixture of ethanol and ethyl acetate to give 4-cyclopropyl-3-chloromethyl-1,2,4-triazole hydrochloride (1.34 g).

4-Cyclopropyl-5-hydroxymethyl-3-mercapto-4H-1,2,4-triazole m.p. 159°–160° C. (Colorless prisms)

$^1$H-NMR (DMSO-d$_6$) δ: 1.0~1.2(4H,m), 2.9~3.0(1H,m), 3.37(1H,br.), 4.51(2H,s), 5.60(1H,br.) Elemental Analysis for C$_6$H$_9$N$_3$OS: Calcd.: C, 42.09; H, 5.30; N, 24.54 Found: C, 42.11; H, 5.34; N, 24.50 4-Cyclopropyl-3-hydroxymethyl-4H-1,2,4-triazole $^1$H-NMR (DMSO-d$_6$) δ: 1.01(4H,d,J=5.4 Hz), 3.3~3.5(1H,m), 4.64 (2H,d,J=5.8 Hz), 5.50(1H,t,J=5.8 Hz), 8.42(1H,s) SIMS (m/z): 140 (MH)$^+$ 4-Cyclopropyl-3-chloromethyl-4H-1,2,4-triazole hydrochloride m.p. 60°–65° C. (Colorless needles)

$^1$H-NMR (DMSO-d$_6$) δ: 1.0~1.3(4H,m), 3.5~3.7 (1H,m), 5.12 (2H,s), 9.51(1H,s) Elemental Analysis for C$_6$H$_8$ClN$_3$.HCl.0.5H$_2$O: Calcd.: C, 35.49; H, 4.96; N, 20.69 Found: C, 35.86; H, 4.55; N, 20.30.

Reference Example 54

A mixture of ethyl bromopyruvate (6.82 g), 2,2,2-trifluorothioacetamide (4.52 g) and ethanol (30 ml) was refluxed for 3 hours. The reaction mixture was cooled, then ethanol was distilled off under reduced pressure. To the residue was added water (40 ml), which was subjected to extraction with ethyl acetate (60 ml×2). The extract solution was washed with water (40 ml) and dried over magnesium sulfate, then the solvent was distilled off under reduced pressure. The residue was subjected to a silica gel chromatography (2.5×45 cm), eluting with ethyl acetate-hexane (1:5). The desired fraction was concentrated to give ethyl 2-trifluoromethyl-4-thiazolecarboxylate (2.2 g) as pale yellow needles.

$^1$H-NMR (CDCl$_3$) δ: 1.43(3H,t,J=7 Hz), 4.48(2H,q,J=7 Hz), 8.40(1H,s)

To anhydrous ether (40 ml) was added lithium aluminium hydride (0.33 g). To this mixture was added dropwise an anhydrous ether (20 ml) solution of ethyl 2-trifluoromethyl-4-thiazole carboxylate (2 g). The mixture was stirred for 3 hours at room temperature. To the reaction mixture was added dropwise water (20 ml) under cooling with ice to decompose excess amount of the reducing agent. To the resultant reaction mixture were added ethyl acetate (50 ml) and water (25 ml), which was subjected to extraction with ethyl acetate. The organic layer was washed with water (25 ml) and a saturated aqueous solution of sodium chloride (25 ml) successively, followed by drying over magnesium sulfate. The solvent was distilled off, and the residue was subjected to a silica gel chromatography (2.5×30 cm), eluting with ethyl acetate-hexane (3:1). The desired fraction was concentrated to give 2-trifluoromethyl-4- hydroxymethylthiazole (1.1 g) as a pale yellow oily product.

¹H-NMR (CDCl₃) δ: 2.50(1H,bs), 4.87(2H,d,J=5 Hz), 7.50(1H,s)

In chloroform (10 ml) was dissolved 2-trifluoromethyl-4-hydroxymethylthiazole (1 g), to which was added dropwise thionyl chloride (2.0 ml). The mixture was refluxed for 4 hours. The reaction mixture was cooled and, then, excess volume of thionyl chloride was distilled off under reduced pressure. To the residue was added dichloromethane (30 ml), which was washed with an aqueous solution of sodium hydrogen carbonate (20 ml) and water (20 ml), successively, followed by drying over magnesium sulfate. The solvent was distilled off, and the residue was subjected to a silica gel chromatography (2.5×20 cm), eluting with ethyl acetate-hexane (1:3). The desired fraction was concentrated to give 2-trifluoromethyl-4-chloromethyl thiazole (0.66 g) as a pale reddish oily product.

¹H-NMR (CDCl₃) δ: 4.62(2H,s), 7.57(1H,s)

Reference Example 55

A mixture of ethyl bromopyruvate (3.6 g), cyclopropanethioamide (2.2 g) and ethanol (30 ml) was refluxed for two hours. The reaction mixture was cooled, then ethanol was distilled off under reduced pressure. To the residue was added water (30 ml), which was subjected to extraction with ethyl acetate (50 ml) twice. The extract solution was washed with water (30 ml), followed by drying over magnesium sulfate. The solvent was distilled off under reduced pressure. The residue was subjected to a silica gel chromatography (2.5×30 cm), eluting with ethyl acetate-hexane (1:3). The desired fraction was concentrated to give ethyl 2-cyclopropyl-4-thiazolcarboxylate (0.84 g) as pale yellow needles.

¹H-NMR (CDCl₃) δ: 1.01~1.24(4H,m), 1.40(3H,t,J=7 Hz), 2.32~2.50(1H,m), 4.41(2H,q,J=7 Hz), 7.95(1H,s)

To a mixture of lithium aluminium hydride (0.32 g) and anhydrous ether (40 ml) was added dropwise an anhydrous ether (10 ml) solution of ethyl 2-cyclopropyl-4-thiazolecarboxylate (1.65 g), followed by stirring for one hour at room temperature. To the reaction mixture was added dropwise water (20 ml) under cooling with ice to decompose excess amount of the reducing agent. To the resultant mixture were added ethyl acetate (50 ml) and water (25 ml), followed by extraction with ethyl acetate. The organic layer was washed with water (25 ml) and a saturated aqueous solution of sodium chloride (25 ml), successively, followed by drying over magnesium sulfate. The solvent was distilled off, and the residue was subjected to a silica gel chromatography (2.5×30 cm), eluting with ethyl acetate-hexane (2:1). The desired fraction was concentrated to give 2-cyclopropyl-4-hydroxymethyl thiazole (0.94 g) as pale yellow needles. ¹H-NMR (CDCl₃) δ: 0.98~1.18(4H,m), 2.24~2.39(1H,m), 3.20(1H,bs.), 4.70(2H,d,J=5 Hz), 6.93(1H,s)

In chloroform (10 ml) was dissolved 2-cyclopropyl-4-hydroxymethylthiazole (0.9 g), to which was added dropwise, under ice-cooling, thionyl chloride (0.68 ml), followed by stirring for 30 minutes at room temperature. Excess thionyl chloride was distilled off under reduced pressure. To the residue was added diethyl ether to yield 2-cyclopropyl-4-chloromethyl thiazole hydrochloride (1.1 g) as pale brown powder. m.p. 108°–110° C.

¹H-NMR (d₆-DMSO) δ: 0.93~1.18(4H,m), 2.32~2.48(1H,m), 4.72(2H,s), 7.47(1H,s)

Reference Example 56

The mother liquor, which remained when (2R,3R)-2-(2,4-difluorophenyl)-1-(1H-1,2,4-triazole-1-yl)-2,3-butanediol was obtained by recrystallization in Reference Example 31, was concentrated under reduced pressure. The concentrate was purified by means of a silica gel chromatography (eluent: ethyl acetate) to give (2S,3R)-2-(2,4-difluorophenyl)-1-(1H-1,2,4-triazol-1-yl)-2,3-butanediol as the first fraction of eluate. m.p. 154°–156° C.

¹H-NMR (CDCl₃) δ: 1.27(3H,dd,J=6.4 Hz,J=1.6 Hz), 2.44(1H,d,OH), 3.99(1H,m), 4.56(1H,dd,J=14 Hz,J=1.6 Hz), 5.05(1H,dd,J=14 Hz,1.6 Hz), 6.65~6.86(2H,m), 7.50~7.62(1H,m), 7.80(1H,s), 8.05(1H,s) IR (KBr) cm⁻¹: 3400, 1615, 1500, 1420, 1275, 1200, 1135.

Reference Example 57

In ethyl acetate (40 ml) was dissolved (2S,3R)-2-(2,4-difluorophenyl)-1-(1H-1,2,4-triazol-1-yl)-2,3-butanediol (2.5 g). To the solution were added, under ice-cooling, triethylamine (1.82 ml) and methanesulfonyl chloride (1.51 g). The mixture was stirred for 30 minutes at room temperature. To the reaction mixture was added ethyl acetate (40 ml), which was washed with water and dried (anhydrous magnesium sulfate), followed by concentration to give (2S,3R)-2-(2,4-difluorophenyl)-3-methanesulfonyloxy-1-(1H-1,2,4-triazol-1-yl)-2-butanol as an oily product. This product was dissolved in methanol (40 ml), to which was added, under ice-cooling, a 28% methanol solution of sodium methylate (2.04 g). The mixture was stirred for 30 minutes at room temperature, then the reaction mixture was concentrated under reduced pressure. To the concentrate was added ethyl acetate (100 ml), which was washed with water, followed by drying (anhydrous magnesium sulfate). The solvent was distilled off under reduced pressure, and the residue was purified by means of a silica gel chromatography (eluent: ethyl acetate-dichloromethane=4:1) to give (2S,3S)-2-(2,4-difluorophenyl)-3-methyl-2-[(1H-1,2,4-triazol-1-yl)methyl]oxirane (1.62 g) as a colorless oily product. This product became a colorless solid in a freezer. m.p. 41°–43° C. [α]$_D^{23}$= +5.8° (c=1.0 in methanol)

NMR (CDCl₃) δ: 1.06(3H,d,J=5.4 Hz), 3.18(1H,q,J=5.4 Hz), 4.42(1H,d,J=15 Hz), 4.80(1H,d,J=15 Hz), 6.76~6.90(2H,m), 7.07~7.20(1H,m), 7.85(1H,s), 8.06(1H,s) IR (KBr) cm⁻¹: 3150, 1615, 1595, 1502, 1420, 1270, 1130

Reference Example 58

The mother liquor, which remained when (2S,3S)-2-(2,4-difluorophenyl)-1-(1H-1,2,4-triazol-1-yl)-2,3-butanediol was obtained by recrystallization in Reference Example 38, was concentrated under reduced pressure. The concentrate was purified by means of a silica gel chromatography (eluent: ethyl acetate) to give (2R,3S)-2-(2,4-difluorophenyl)-1-(1H-1,2,4-triazol-1-yl)-2,3-butanediol as the first fraction of eluate. m.p. 156°–157° C.

¹H-NMR (CDCl₃) δ: 1.27(3H,dd,J=6.4 Hz,J=1.6 Hz), 2.42(1H,d,OH), 3.99(1H,m), 4.57(1H,dd,J=14 Hz,J=1.6 Hz), 5.05(1H,dd,J=14 Hz,1.6 Hz), 6.67~6.86(2H,m), 7.50~7.62(1H,m), 7.80(1H,s), 8.04(1H,s) IR (KBr) cm$^{-1}$: 3350, 1615, 1510, 1420, 1275, 1200, 1130.

Reference Example 59

In ethyl acetate (4 ml) was dissolved (2R,3S)-2-(2,4-difluorophenyl)-1-(1H-1,2,4-triazol-1-yl)-2,3-butanediol (0.18 g). To the solution were added triethylamine (0.10 ml) and methanesulfonyl chloride (84 mg) under ice-cooling. The mixture was stirred for 30 minutes at room temperature, to which was added ethyl acetate (10 ml). The reaction mixture was washed with water and dried (anhydrous magnesium sulfate), followed by concentration to give (2R,3S)-2-(2,4-difluorophenyl)-3-methanesulfonyloxy-1-(1H-1,2,4-triazol-1-yl)-2-butanol as an oily product. This product was dissolved in methanol (6 ml), to which was added a 5.6% methanol solution of sodium methylate (0.76 ml) under ice-cooling. The mixture was stirred for 30 minutes at room temperature, which was then concentrated under reduced pressure. To the concentrate was added ethyl acetate (30 ml), which was washed with water and dried (anhydrous magnesium sulfate). The solvent was then distilled off, and the residue was purified by means of a silica gel chromatography (eluent: hexane-ethyl acetate=1:2) to afford (2R,3R)-2-(2,4-difluorophenyl)-3-methyl-2-[(1H-1,2,4-triazol-1-yl)methyl]oxirane (0.15 g) as a colorless oily product.

NMR (CDCl$_3$) δ: 1.06(3H,d,J=5.4 Hz), 3.18(1H,q,J=5.4 Hz), 4.42(1H,d,J=15 Hz), 4.80(1H,d,J=15 Hz), 6.76~6.90(2H,m), 7.07~7.20(1H,m), 7.85(1H,s), 8.06(1H,s) IR (film) cm$^{-1}$: 1615, 1595, 1505, 1420, 1270, 1140

Reference Example 60

2′,4′-Difluoro-2-hydroxypropiophenone (2.8 g) was dissolved in methylene chloride (28 ml), to which were added triethylamine (2.5 ml) and methanesulfonyl chloride (1.3 ml) at 0° C. After stirring for 15 minutes, the mixture was washed with water (30 ml), and the organic layer was dried over anhydrous sodium sulfate and concentrated under reduced pressure. The residue was subjected to silica gel column chromatography (3 cm×10 cm) and eluted with methylene chloride. The desired fraction was concentrated, to give 2′,4′-difluoro-2-methanesulfonyloxypropiophenone (3.0 g) as a colorless oil. This compound (3.0 g) was dissolved in 30 ml of N,N-dimethylformamide, to which were added 1H-1,2,4-triazole (0.94 g) and then 60% sodium hydride suspension in oil (0.5 g) at −10° C. After stirring at 0° C. for 50 minutes, the reaction mixture was added to a mixture of ethyl acetate (100 ml) and water (200 ml) for extraction. The water layer was extracted with ethyl acetate (100 ml) and the ethyl acetate layers were combined, washed with saturated aqueous solution of sodium chloride (30 ml×2), dried over anhydrous magnesium sulfate, and concentrated under reduced pressure. The residue was subjected to silica gel column chromatography (3 cm×10 cm) and eluted with ethyl acetate. The desired fraction was concentrated, to give 2′,4′-difluoro-2-(1H-1,2,4-triazol-1-yl)propiophenone (1.5 g) as a colorless oil. This compound (1.24 g) was added to a mixture of dimethyl sulfoxide (30 ml), 60% sodium hydride suspension in oil (0.25 g) and trimethylsulfoxonium iodide (1.38 g) at 10° C. and then the temperature was raised to 25° C. Two hours later, the reaction mixture was added to a mixture of diethyl ether (100 ml) and water (150 ml), diethyl ether layer was separated, and the water layer was extracted with diethyl ether (100 ml×2). The organic layers were combined, washed with saturated aqueous solution of sodium chloride (50 ml×2), dried over anhydrous magnesium sulfate, and concentrated under reduced pressure. The residue was subjected to silica gel column chromatography (3 cm×10 cm) and eluted with ethyl acetate-hexane (3:1), to give 2-(2,4-difluorophenyl)-2-[1-(1H-1,2,4-triazol-1-yl)ethyl]oxirane as a colorless oil (0.87 g).

$^1$H-NMR (CDCl$_3$) δ: 1.61 (3H, d, J=7.0 Hz), 1.62 (3H, d, J=6.0 Hz), 2.64 (1H, d, J=4.6 Hz), 2.81 (1H, d, J=4.6 Hz), 2.87 (1H, d, J=4.6 Hz), 3.18 (1H, d, J=4.6 Hz), 4.92 (2H, q, J=7.0 Hz), 6.7-7.2 (6H, m), 7.87 (1H, s), 7.94 (1H, s), 8.04 (1H, s), 8.12 (1H, s)

Reference Example 61

To a solution of 2-(2,4-difluorophenyl)-2-[(1R)-1-(3,4,5,6-tetrahydro-2H-pyran-2-yloxy)ethyl]oxirane (1.7 g) and imidazole (0.49 g) in N,N-dimethylformamide (17 ml) was added 60% oily sodium hydride in mineral oil (0.29 g) by portions at 20° C. with constant stirring. After 5 minutes, the mixture was heated at 70° C. for 3 hours. The reaction mixture was cooled, then poured into water (50 ml) and extracted with ethyl acetate (20 ml×3). The ethyl acetate layers were combined, washed with saturated aqueous sodium chloride solution (20 ml), dried over anhydrous magnesium sulfate and concentrated under reduced pressure. The residue was subjected to silica gel chromatography (3 cm×15 cm) using methanol-ethyl acetate (5:95) as the eluent. The desired fraction was concentrated under reduced pressure to give (3R)-2-(2,4-difluorophenyl)-1-(1-imidazolyl)-3-(3,4,5,6-tetrahydro-2H-pyran-2-yloxy)-2-butanol (1.8 g) as a colorless syrup.

$^1$H-NMR (CDCl$_3$) δ: 0.92, 1.03(3H,d,J=6.2 Hz, J=6.4 Hz), 1.5-2.0(6H,m), 3.5-4.8(6H,m), 6.6-7.5(6H,m) IR(neat)cm$^{-1}$: 3300, 2900, 1650, 1600, 1490 SIMS(m/z): 353 (MH+)

In ethanol (8.5 ml) was dissolved (3R)-2-(2,4-difluorophenyl)-1-(1-imidazolyl)-3-(3,4,5,6-tetrahydro-2H-pyran-2-yloxy)-2-butanol (1.7 g) followed by addition of trifluoroacetic acid (8.5 ml) at 0° C. After 10 minutes, the temperature was adjusted to 20° C. and the mixture was allowed to stand for 1 hour. The reaction mixture was then concentrated under reduced pressure and the residue was subjected to silica gel chromatography (2 cm×10 cm) using methanol-methylene chloride (1:9) as the eluent. The desired fraction was concentrated to give (3R)-2-(2,4-difluorophenyl)-1-(1-imidazolyl)-2,3-butanediol (1.7 g).

$^1$H-NMR (DMSO-d$_6$) δ: 0.83, 1.03(3H,d,J=6.2 Hz, J=6.4 Hz), 4.15-4.35(1H,m ), 4.62(1H,d,J=14.2 Hz), 4.71(1H,d,J=14.2 Hz), 5.5 (1H,br.), 5.71(1H,s), 6.9-7.0(1H,m), 7.15-8.8(5H,m ) IR(neat)cm$^{-1}$: 3300, 1660, 1495, 1410, 1190, 1120 SIMS(m/z): 269 (MH+)

To a methylene chloride (60 ml) solution containing (3R)-2-(2,4-difluorophenyl)-1-(1-imidazolyl)-2,3-butanediol (1.7 g), triethylamine (0.88 ml) and tetrahydrofurane (2.0 ml) was added methanesulfonyl chloride (0.50 ml) dropwise at 0° C. with constant stirring. After 10 minutes, the temperature was adjusted to 20° C. and the mixture was further stirred for 50 minutes. Then, methanesulfonyl chloride (0.50 ml) and triethylamine (0.88 ml) were added and the reaction mixture was stirred for 1 hour. The reaction mixture was poured into water (100 ml) and extracted with methylene chloride (50 ml×3). The methylene chloride layers were combined, dried over anhydrous sodium sulfate and concentrated under reduced pressure. To the residue was added methanol (30 ml) followed by addition of 28% methanol solution of sodium methoxide (1.3 ml) at 0° C. After 5 minutes, the temperature was adjusted to 20° C. and the reaction mixture was stirred for 20 minutes. The reaction mixture was then poured into water (100 ml) and extracted with ethyl acetate (30 ml×3). The ethyl acetate layers were combined, washed with saturated aqueous sodium chloride solution (20 ml), dried over anhydrous magnesium sulfate and concentrated under reduced pressure. The residue was subjected to silica gel chromatography (3 cm×15 cm) using ethyl acetate as the eluent. The desired fraction was concentrated under reduced pressure. To this residue was added isopropyl ether-n-hexane, whereby (2R,3S)-2-(2,4-difluorophenyl)-2-(1-imidazolyl)methyl-3-methyloxirane (0.14 g) was crystalized as colorless prisms. m.p. 73°-76° C.

Reference Example 62

To a N,N-dimethylformamide (35 ml) solution containing (2R,3R)-3-(2,4-difluorophenyl)-3,4-epoxy-2-butyl methanesulfonate (3.5 g) and imidazole (1.2 g) was added 60% sodium hydride in mineral oil (0.70 g) at 0° C. with constant stirring. After 10 minutes, the temperature was adjusted to 20° C. and the mixture was stirred for 20 hours. The reaction mixture was then poured into water (100 ml) and extracted with ethyl acetate (30 ml×4). The ethyl acetate layers were combined, washed with saturated aqueous sodium chloride solution (30 ml), dried over anhydrous magnesium sulfate and concentrated under reduced pressure. The residue was purified by silica gel chromatography (3 cm×15 cm) using methanol-ethyl acetate (5:95) as the eluent. The desired fraction was concentrated under reduced pressure and the residue was crystallized by addition of isopropyl ether and n-hexane to give (2R,3S)-2-(2,4-difluorophenyl)-2-(1-imidazolyl)methyl-3-methyloxirane (1.7 g) as colorless prisms. m.p. 73°-76° C.

$^1$H-NMR (CDCl$_3$) δ: 1.61(3H,d,J=5.6 Hz), 3.15(1H,q,J=5.6 Hz), 4.13(1H,d,J=14.8 Hz), 4.63(1H,d,J=14.8 Hz), 6.66-6.78(2H.m), 6.83(1H,s), 6.94(1H,s), 6.92-7.04(1H,m), 7.29(1H,s) Elemental Analysis for C$_{13}$H$_{12}$F$_2$N$_2$O.$\frac{1}{4}$H$_2$O Calcd.: C, 61.29; H, 4.95; N, 11.00 Found: C, 61.46; H, 4.73; N, 10.89 IR(KBr)cm$^{-1}$: 1600, 1585, 1495, 1415, 1270, 1260, 1210, 1110, 1090

Example 1

In dimethylformamide (20 ml) were dissolved 2-(2,4-difluorophenyl)-2-(1H-1,2,4-triazol-1-ylmethyl)oxirane (1.2 g) and 1-(2-mercaptoethyl)benzimidazole (1.1 g). To this solution was added sodium hydride (60% in oil, 0.36 g) under ice-cooling and the mixture was stirred for 90 minutes. The dimethylformamide was then distilled off under reduced pressure and the residue was diluted with water (50 ml) and extracted with ethyl acetate. The extract was washed with water and saturated aqueous sodium chloride solution successively and dried (MgSO$_4$) and the solvent was distilled off. The residue was subjected to silica gel chromatography (2.5×40 cm) and elution was carried out with ethyl acetate-acetone-methanol (6:2:1). The desired fraction was concentrated to give compound 1 (1.1 g) as a colorless powder.

Elemental Analysis for C$_{20}$H$_{19}$F$_2$N$_5$OS.0.5H$_2$O Calcd.: C, 56.59; H, 4.75; N, 16.50 Found: C, 57.07; H, 4.96; N, 15.98 $^1$H-NMR (CDCl$_3$) δ: 2.81-3.12(4H,m), 4.30-4.37(2H,m), 4.64 (2H,s), 6.74-6.82(2H,m), 7.28-7.50(5H,m), 7.71 -7.83(1H,b), 7.81(1H,s), 7.88(1H,s), 7.93 (1H,s) SIMS (m/z): 416 (M+H)$^+$ Example 2

A mixture of 2-(1H-1,2,4-triazol-1-yl)ethanethiol (4.5 g), 2-(2,4-difluorophenyl)-2-(1H-1,2,4-triazol-1-ylmethyl)oxirane methanesulfonate (4 g), potassium carbonate (6.5 g) and dimethylformamide (20 ml) was stirred at 70° C. for 1 hour. After cooling, the reaction mixture was diluted with water (150 ml), saturated with sodium chloride and extracted with ethyl acetate (150 ml×3). The extract was washed with water (50 ml×3) and dried (anhydrous sodium sulfate) and the solvent was distilled off to give a yellow oil. This product was purified by silica gel chromatography (ethyl acetate-acetonemethanol=6:2:1) and the resulting oil was crystallized from ethyl ether-ethyl acetate to give compound 2 (0.85 g) as colorless prisms. m.p. 114°-115° C.

Elemental Analysis for C$_{15}$H$_{16}$F$_2$N$_6$OS Calcd.: C, 49.17; H, 4.40; N, 22.94 Found: C, 48.93; H, 4.40; N, 22.87.

Example 3

In methylene chloride (10 ml) was dissolved compound 2 (0.2 g), and with stirring at room temperature, m-chloroperbenzoic acid (purity 85%, 0.29 g) was added. The mixture was stirred at room temperature for 16 hours. The mixture was washed with 5% aqueous sodium hydrogen carbonate solution, and the organic layer was dried (MgSO$_4$) and concentrated under reduced pressure. The residue was subjected to silica gel column chromatography (1.5×15 cm) and elution was carried out with ethyl acetate-acetone-methanol (8:2:1). The desired fraction was concentrated to give compound 3 (0.12 g) as a colorless powder.

$^1$H-NMR (CDCl$_3$) δ: 3.36-3.79(4H,m), 4.63-4.79(3H,m), 4.89(1H,d,J=14.2 Hz), 5.61(1H,s), 6.78-6.92(2H,m), 7.38-7.53(1H,m), 7.86(1H,s), 7.91-7.95(2H,m), 8.18(1H,s) SIMS(m/z): 399(M+H)$^+$

Example 4

In methylene chloride (15 ml) was dissolved compound 2 (0.3 g), and with stirring under ice-cooling, m-chloroperbenzoic acid (purity 85%, 0.22 g) was added. The mixture was stirred under ice-cooling for 2 hours, and washed with 5% aqueous sodium hydrogen carbonate solution. The organic layer was dried (MgSO$_4$) and concentrated under reduced pressure. The residue was subjected to silica gel column chromatography (1.5×20 cm) and elution was carried out with ethyl acetate-acetone-methanol (5:4:1). The desired fraction was concentrated to give compound 4 (0.07 g) as a colorless powder.

$^1$H-NMR (CDCl$_3$) δ: 2.87-3.48(4H,m), 4.36-4.72(4H,m), 5.48(1H,bs), 6.81-7.02(2H,m), 7.59-7.75 (1H,m), 7.85-7.99(2H,m), 8.11(1H,s), 8.15(1H,s)

Example 5

A mixture of 2-(1-imidazolyl)ethanethiol (4.5 g), 2-(2,4-difluorophenyl)-2-(1H-1,2,4-triazol-1-ylmethyl)oxirane methanesulfonate (4 g), potassium carbonate (6.5 g) and dimethylformamide (30 ml) was stirred at 70° C. for 1 hour. After cooling, the reaction mixture was diluted with water (100 ml), saturated with sodium chloride and extracted with ethyl acetate (100 ml×3). The extract was washed with water (30 ml×3) and dried (anhydrous sodium sulfate) and the solvent was distilled off to give a colorless oil. This product was purified by silica gel column chromatography (ethyl acetate-acetone-methanol=6:2:1) and the resulting oil was crystallized from ethyl ether to give compound 5 (1.28 g) as a colorless powder. m.p. 103°–105° C.

Elemental Analysis for $C_{16}H_{17}F_2N_5OS$ Calcd.: C, 52.59; H, 4.69; N, 19.17 Found: C, 52.32; H, 4.69; N, 19.03.

Example 6

In a manner like that described in Example 3, compound 5 (0.3 g) was oxidized with m-chloroperbenzoic acid to give compound 6 (0.17 g, 51%) as a colorless powder.

$^1$H-NMR (CDCl$_3$) δ: 3.51–3.73(4H,m), 4.37–4.43(2H,m), 4.59(1H,d,J=14.2 Hz), 4.80(1H,d,J=14.2 Hz), 6.44(1H,bs). 6.80–6.99(4H,m), 7.40–7.54(2H,m), 7.81(1H,s), 8.11(1H,s) SIMS(m/z): 398(M+H)+

Examples 7–12

In a similar manner to that described in Example 1, 2-(2,4-difluorophenyl)-2-(1H-1,2,4-triazol-1-ylmethyl)oxirane ("Epoxy compound" in Table 9) was reacted with the various thiols in Table 9 to give compounds 7, 8, 9 (10, 11), 17, 19 and 21.

TABLE 9

| Ex. No. | Starting compounds | Reaction conditions | Products |
|---|---|---|---|
| 7 | Epoxy compound (0.74 g) 2-[2-(1-imidazolyl)-ethylthio]-ethanethiol (0.70 g) | Dimethyl-formamide (8 ml) 60% sodium hydride (in oil: 0.15 g) 0° C. 1 hour | Compound 7 (1.03 g, 78%) oily substance $^1$H-NMR(CDCl$_3$)δ: 2.40–2.65(4H, m), 2.83(2H, t, J=6.6Hz), 2.91(1H, d, J=14.2Hz), 3.25(1H, d, J=14,2Hz), 4.12(2H, t, J=6.6Hz), 4.69(2H, s), 6.70–6.87(2H, m), 6.93(1H, d, J=1.2Hz), 7.01(1H, d, J=1.2Hz), 7.51(1H, m), 7.55(1H, s), 7.81(1H, s), 8.04(1H, s) Treatment of 7 (1.0 g) with a hydrogen chloride-ethylacetate solution in ethyl acetate gave 1.0 g of hydrochloride as colorless powder. |
| 8 | Epoxy compound (2.0 g) 2-(4-Pyridyl)-ethanethiol (1.2 g) | Dimethyl-formamide (20 ml) 60% sodium hydride (in oil: 0.41 g) 0° C. 20 min. | Compound 8 (2.6 g, 81%) oily substance $^1$H-NMR(CDCl$_3$)δ: 2.60–2.90(4H, m), 2.89(1H, d, J=14.0Hz), 3.27(1H, d, J=14.0Hz), 4.57(1H, bs), 4.68(2H, s), 6.70–6.90(2H, m), 7.04(2H, d, J=6.2Hz), 7.40–7.55(1H, m), 7.82(1H, s), 7.98(1H, s), 8.49(2H, d, J=6.2Hz) |
| 9 | Epoxy compound (1.9 g) 1-(4-Pyridyl)-ethanethiol (1.1 g) | Dimethyl-formamide (30 ml) 60% sodium hydride (in oil: 0.38 g) 0° C. 15 min. | Compound 9 (1.89 g, 63%) oily substance $^1$H-NMR(CDCl$_3$)δ: 1.47(3H, d, J=7.0Hz), 1.49(3H, d, J=7.20Hz), 2.71(2H, d, J=13.4Hz), 2.93(1H, d, J=13.4Hz), 3.05(1H, d, J=13.4Hz), 3.84(1H, q, J=7.0Hz), 3.92(1H, q, J=7.2Hz), 4.51–4.76(6H, m), 6.69–6.87(4H, m), 7.16(2H, d, J=6.2Hz), 7.18(2H, d, J=6.0Hz), 7.41–7.54(2H, m), 7.81(1H, s), 7.82(1H, s), 7.93(1H, s), 7.94(1H, s), 8.53(4H, d, J=6.0Hz) This product was a mixture of diastereomers and was fractionally crystallized from a mixture of diethyl ether and isopropyl ether to afford two types of diastereomer. Compound 10 (0.90 g): Diastereomer (high polarity) mp. 98–99° C. Compound 11 (0.41 g): Diastereomer (low polarity) mp. 39–44° C. |
| 10 | Epoxy compound (1.2 g) 2-(1-Methyl-2-imida-zolyl-methylthio)-ethane thiol (0.95 g) | Dimethyl-formamide (15 ml) 60% sodium hydride (in oil: 0.22 g) 0° C. 10 min. | Compound 17 (1.66 g, 77%) mp. 134–135° C. $^1$H-NMR(CDCl$_3$)δ: 2.53(2H, t, J=8.0Hz), 2.74–2.89(1H, m), 3.10–3.30(3H, m), 3.68(3H, s), 3.82(1H, d, J=15.0Hz), 3.92(1H, d, J=15.0Hz), 4.70(1H, d, J=14.0Hz), 4.89(1H, d, J=14.0Hz), 6.54(1H, s), 6.76–6.84(3H, m), 7.48–7.60(1H, m), 7.71(1H, s), 7.99(1H, s), 8.08(1H, s) |
| 11 | Epoxy compound (1.41 g) 2-(4-Pyridyl-methylthio)-ethanethiol (1.33 g) | Dimethyl-formamide (20 ml) 60% sodium hydride (in oil: 0.36 g) 0° C. 1 hour | Compound 19 (1.6 g, 63%) $^1$H-NMR(CDCl$_3$)δ: 2.54–2.64(4H, m), 2.89(1H, d, J=14.0Hz), 3.24(1H, d, J=14.0Hz), 3.65(2H, s), 4.68(2H, s), 4.90(1H, bs), 6.71–6.89(2H, m), 7.22(2H, d, J=6.2Hz), 7.41–7.59(2H, m), 7.82(1H, s), 8.01(1H, s), 8.53(2H, d, J=6.2Hz) Treatment of this product (1.6 g), in ethyl acetate, with hydrogen chloride-ethylacetate gave hydrochloride (1.2 g) as colorless powder. |
| 12 | Epoxy compound (1.42 g) 2-[2-(1H-1,2,4-triazol-1-yl)ethyl-thio]-ethanethiol (1.36 g) | Dimethyl-formamide (15 ml) 60% sodium hydride (in oil: 0.29 g) 0° C. 1 hour | Compound 21 (1.07 g, 43%) oily substance $^1$H-NMR(CDCl$_3$)δ: 2.44–2.65(4H, m), 2.89(1H, d, J=14Hz), 2.97(2H, t, J=6.5Hz), 3.25(1H, d, J=14Hz), 4.34(2H, t, J=6.5Hz), 4.70(2H, s), 6.72–6.90(2H, m), 7.42–7.55(1H, m), 7.83(1H, s), 7.95(1H, s), 7.99(1H, s), 8.14(1H, s) This product (0.6 g) was processed with a hydrogen chloride-ethyl acetate solution to afford 21• hydrochloride (0.57 g) as colorless powder. |

Example 13

A mixture of (2RS,3SR)-2-(2,4-difluorophenyl)-3-methyl-2-(1H-1,2,4-triazol-1-ylmethyl)oxirane (0.5 g), 2-mercapto-5,6-dihydro-4H-cyclopentathiazole (0.38 g) and 1M tetrabutylammonium fluoride (2.2 ml) in ethanol (15 ml) was refluxed for 4 hours. The ethanol was then distilled off under reduced pressure and the residue was diluted with water (25 ml) and extracted with ethyl acetate. The extract was washed with water and saturated aqueous sodium chloride solution successively and dried (MgSO4), and the solvent was distilled off under reduced pressure. The residue was subjected to silica gel column chromatography (2.5×40 cm) and elution was carried out with ethyl acetate-n-hexane (3:2). The desired fraction was concentrated, and ether-hexane (2:1) was added to the residue, whereupon compound 12 (0.34 g) separated out as colorless prisms. m.p. 70°–72° C.

Elemental Analysis for $C_{18}H_{18}F_2N_4OS_2$ Calcd.: C, 52.93; H, 4.44; N, 13.72 Found: C, 52.65; H, 4.38; N, 13.70 $^1$H-NMR (CDCl$_3$) δ: 1.22(3H,d,J=7.2 Hz), 2.43–2.62(2H,m), 2.87–2.99(4H,m), 4.02(1H,q,J=7.2 Hz), 4.98(2H,s), 6.64–6.82(2H,m), 7.08(1H,s), 7.39–7.52(1H,m), 7.67(1H,s), 8.06(1H,s)

Example 14

A mixture of (2RS,3SR)-2-(2,4-difluorophenyl)-3-methyl-2-(1H-1,2,4-triazol-1-ylmethyl)oxirane (0.5 g), 1-(2-mercaptoethyl)-1H-1,2,4-triazole (0.31 g) and 1M tetrabutylammonium fluoride (2.2 ml) in ethanol (20 ml) was refluxed for 12 hours. The ethanol was then distilled off under reduced pressure and the residue was diluted with water (25 ml) and extracted with ethyl acetate. The extract was washed with water and saturated aqueous sodium chloride solution successively and dried (MgSO4), and the solvent was distilled off under reduced pressure. The residue was subjected to silica gel column chromatography (2.5×40 cm) and elution was carried out with ethyl acetate-acetone-methanol (10:2:1). The desired fraction was concentrated to give compound 13 (0.4 g) as oil.

$^1$H-NMR (CDCl$_3$) δ: 1.11(3H,d,J=7.2 Hz), 3.09–3.38(3H,m), 4.37–4.59(2H,m), 4.73(1H,d,J=14 Hz), 4.93 (1H,d,J=14 Hz ), 5.03(1H,bs), 6.69–6.78(2H,m), 7.29 –7.41(1H,m), 7.78(1H,s), 7.79(1H,s), 8.02 (1H,s), 8.19(1H, s)

This product (0.14 g) was treated with hydrogen chloride in ethyl acetate to give the hydrochloride (0.11 g) as colorless powder. m.p. 179°–181° C.

Elemental Analysis for $C_{16}H_{18}F_2N_6OS\cdot 2HCl\cdot 0.5H_2O$ Calcd.: C, 41.57; H, 4.58; N, 18.18 Found: C, 41.87; H, 4.41; N, 18.45.

Example 15

In a manner like that described in Example 3, compound 13 (0.2 g) was oxidized with m-chloroperbenzoic acid (0.28 g) to give compound 14 (0.8 g, 37%) as a colorless powder.

$^1$H-NMR (CDCl$_3$) δ: 1.22(3H,d,J=7.2 Hz), 3.56–4.08(3H,m), 4.76–4.82(2H,m), 4.91(1H,d,J=14.2 Hz), 5.36(1H,d,J=14.2 Hz), 5.71(1H,s), 6.71–6.81(2H,m), 7.18–7.32(1H,m), 7.75(1H,s), 7.77(1H,s), 8.00(1H,s), 8.25(1H,s) SIMS(m/z): 413(M+H)+

Example 16

A mixture solution of (2RS,3SR)-2-(2,4-difluorophenyl)-3-methyl-2-(1H-1,2,4-triazol-1-ylmethyl)oxirane (0.60 g), pyridine-4-methanethiol (0.45 g) and 28% sodium methoxide-methanol (0.55 g) in ethanol (12 ml) was refluxed for 1 hour. The ethanol was then distilled off under reduced pressure and the residue was subjected to silica gel chromatography (2.5× 15 cm), and elution was carried out with methanol-ethyl acetate (5:95). The desired was concentrated and a mixture of ethyl acetate and diethyl ether was added to the residue to give compound 15 (0.67 g) as colorless needles. m.p. 98°–99° C.

Elemental Analysis for $C_{18}H_{18}F_2N_4OS$ Calcd.: C, 57.43; H, 4.82; N, 14.88 Found: C, 57.12; H, 4.70; N, 14.78 $^1$H-NMR (CDCl$_3$) δ: 1.14(3H,d,J=6.80 Hz), 3.16(1H,q,J=6.80 Hz), 3.80(1H,d,J=13.8 Hz), 3.92(1H,d,J=13.8 Hz), 4.57(1H,d,J=14.2 Hz), 4.97(1H,d,J=14.2 Hz), 5.04(1H,s), 6.64–6.77(2H,m), 7.28–7.40(1H,m), 7.31(2H,d,J=6.0 Hz), 7.74(1H,s), 7.76(1H,s), 8.59(2H,d,J=6.0 Hz)

Examples 17–19

In a manner like that described in Example 16, (2RS,3SR)-2-(2,4-difluorophenyl)-3-methyl-2-(1H-1,2,4-triazol-1-ylmethyl)oxirane ("Methyl-epoxy compound" in Table 10) was reacted with the various thiols in Table 10 to give compound 16, 22 and 23.

TABLE 10

| Ex. No. | Starting compounds | Reaction conditions | Products |
|---|---|---|---|
| 17 | Methyl-epoxy compound (0.50 g) 1-Methyl-2-imidazolyl-methane thiol (0.38 g) | Ethanol (15 ml) 28% sodium methylate-methanol solution (0.46 g) 90° C. 2 hours | Compound 16 (0.60 g, 80%) colorless powder $^1$H-NMR(CDCl$_3$)δ: 1.20(3H, d, J=7.0Hz), 3.51(1H, q, J=7.0Hz), 3.69(3H, s), 3.80(1H, d, J=15.2Hz), 4.04(1H, d, J=15.2Hz), 4.56(1H, d, J=14.0Hz), 4.77(1H, bs), 4.84(1H, d, J=14.0Hz), 6.68–6.80(2H, m), 6.86(1H, d, J=1.2Hz), 6.98(1H, d, J=1.2Hz), 7.35–7.50(1H, m), 7.68(1H, s), 7.95(1H, s) |
| 18 | Methyl-epoxy compound (0.67 g) 2-[2-(1H-1,2,4-triazole-1-yl)ethyl-thio]ethane thiol (0.61 g) | Ethanol (10 ml) 28% sodium methylate-methanol solution (0.5 ml) Reflux 2.5 hours | Compound 22 (0.59 g, 50%) oily substance $^1$H-NMR(CDCl$_3$)δ: 1.16(3H, d, J=7Hz), 2.58–3.00(4H, m), 3.07(2H, t, J=6.5Hz), 3.27(1H, q, J=7Hz), 4.40(2H, t, J=6.5Hz), 4.85(1H, d, J=14Hz), 4.89(1H, s), 5.06(1H, d, J=14Hz), 6.75(2H, m), 7.30–7.45(1H, m), 7.78(1H, s), 7.84(1H, s), 7.98(1H, s), 8.08(1H, s) This product was treated with a hydrogen chloride-ethyl acetate solution to afford 22•hydrochloride as colorless powder. |
| 19 | Methyl-epoxy compound (1.11 g) 2-[2-(1-Imidazolyl)ethylthio]ethane thiol (0.83 g) | Ethanol (10 ml) 28% sodium methylate-methanol (0.9 ml) Reflux 3 hours | Compound 23 (1.21 g, 62%) oily substance $^1$H-NMR(CDCl$_3$)δ: 1.16(3H, d, J=7Hz), 2.65(2H, t, J=6.8Hz), 2.75–3.02(4H, m), 3.28(1H, q, J=7Hz), 4.18(2H, t, J=6.8Hz), 4.84(1H, d, J=15Hz), 5.05(1H, d, J=15Hz), 6.65–6.80(2H, m), 6.99(1H, t, J=1.2Hz), 7.07(1H, d, J=1.2Hz), 7.28–7.45(1H, m), 7.57(1H, s), 7.76(1H, s), 7.86(1H, s) This product was treated with a hydrogen chloride-ethyl acetate solution to afford 23•hydrochloride as colorless powder. |

Example 20

A mixture solution of 2-(2,4-difluorophenyl)-3-mercapto-1-(1H-1,2,4-triazol-1-yl)propan-2-ol (1.2 g), 2-(2-chloroethylthio)-1-methylimidazole (1.2 g) and 28% sodium methoxide-methanol (0.94 g) in ethanol (30 ml) was refluxed for 2 hours. The ethanol was then distilled off under reduced pressure and the residue was subjected to silica gel chromatography (3.5×15 cm) using methanol-ethyl acetate (5:95) as the eluent. The desired fraction was concentrated and dichloromethane and diethyl ether were added to the residue, whereby compound 18 (0.90 g) was obtained as colorless needles. m.p. 92°–93° C.

Elemental Analysis for $C_{17}H_{19}F_2N_5OS_2$ Calcd.: C, 49.62; H, 4.65; N, 17.02 Found: C, 49.45; H, 4.71; N, 16.84 $^1$H-NMR (CDCl$_3$) δ: 2.89(2H,b.t,J=7.40 Hz), 3.22–3.30(2H,m), 3.20(1H,d,J=14.8 Hz), 3.39(1H,d,J=14.8 Hz), 3.57(3H,s), 4.65(1H,d,J=14.2 Hz), 4.75(1H,d,J=14.2 Hz), 6.19(1H,s), 6.74–6.85(2H,m), 6.92(1H,s), 6.98(1H,s), 7.47–7.60(1H,m), 7.76(1H,s), 8.07 (1H,s)

Examples 21–22

In a manner like that described in Example 20, 2-(2,4-difluorophenyl)-3-mercapto-1-(1H-1,2,4-triazol-1-yl)propane-2-ol (simply referred to "thiol derivative" in Table 11) was allowed to react with a chloro-derivative shown in Table 11 to afford Compounds 20 and 24.

TABLE 11

| Ex. No. | Starting compounds | Reaction conditions | Products |
|---|---|---|---|
| 21 | Thiol deriv. (0.69 g) 2-(1-methyl-5-tetrazolyl-thio)ethyl-chloride (1.0 g) | Ethanol (15 ml) 28% sodium methylate-methanol solution (0.54 g) 2 hours reflux | Compound 20 (0.53 g, 50%) oily substance $^1$H-NMR(CDCl$_3$)δ: 2.91–2.99(2H, m), 3.07(1H, d, J=14.2Hz), 3.33(1H, d, J=14.2Hz), 3.47–3.54(2H, m), 3.92(3H, s), 4.73(2H, s), 4.96(1H, bs), 6.78–6.89(2H, m), 7.43–7.59(1H, m), 7.81(1H, s), 8.03(1H, s) This product was treated with a hydrogen chloride-ethyl acetate solution to afford 20•hydrochloride (0.59 g) as colorless powder. |
| 22 | Thiol deriv. (1.08 g) 2-(4-Pyridyl-thio)ethyl chloride hydrochloride (0.88 g) | Ethanol (30 ml) 28% sodium methylate-methanol solution (1.54 g) 2 hours reflux | Compound 24 (0.95 g, 58%) oily substance $^1$H-NMR(CDCl$_3$)δ: 2.71–2.82(2H, m), 2.98(1H, d, J=14Hz), 3.09–3.21(2H, m), 3.31(1H, d, J=14Hz), 4.71(2H, s), 4.84(1H, bs), 6.71–6.89(2H, m), 7.09(2H, d, J=6.2Hz), 7.42–7.58(1H, m), 7.83(1H, s), 7.97(1H, s), 8.41(2H, d, J=6.2Hz) This product (0.95 g) was treated with a hydrogen chloride-ethylacetate solution to afford 24•hydrochloride as colorless powder (0.75 g). |

Example 23

In diethyl ether (30 ml) was dissolved compound 16 (0.52 g) prepared in Example 17 followed by addition of hydrogen chloride in ethyl acetate. The resulting mixture was allowed to stand and the supernatant was removed by decantation. The residue was diluted with diethyl ether (30 ml) and allowed to stand and the supernatant was removed by decantation. The residue was dissolved in ethanol (10 ml) followed by addition of ethyl acetate (100 ml) and the mixture was allowed to stand for a day for crystallization. The resulting crystals were collected by filtration and dried under reduced pressure to give compound 16.dihydrochloride (0.49 g). m.p. 114°–116° C.

Elemental Analysis for $C_{17}H_{19}F_2N_5OS \cdot 2HCl \cdot H_2O$ Calcd.: C, 43.41; H, 4.93; N, 14.89 Found: C, 43.76; H, 4.72; N, 14.96 $^1$H-NMR (DMSO-d$_6$) δ: 1.05(3H,d,J=6.6 Hz), 3.43(1H,q,J=6.6 Hz), 3.90(3H,s), 4.32(1H,d,J=15.4 Hz), 4.45(1H,d,J=15.4 Hz), 4.56(1H,d,J=14.4 Hz), 4.86(1H,d,J=14.4 Hz), 6.95(1H,m), 7.10–7.40(2H,m), 7.68(1H,s), 7.73(1H,s), 7.82(1H,s), 8.54(1H,s)

Example 24

A mixture of (2RS,3SR)-2-(2,4-difluorophenyl)-3-methyl-2-(1H-1,2,4-triazol-1-yl)methyloxirane (0.3 g), 2-methyl-1,3,4-thiadiazole-5-thiol (0.19 g) and 1M tetrabutylammonium fluoride (1.3 ml) in ethanol (10 ml) was refluxed for 4.5 hours. The ethanol was then distilled off under reduced pressure and the residue was diluted with water (15 ml) and extracted with ethyl acetate.

The extract was washed with water and saturated aqueous sodium chloride solution successively and dried (MgSO$_4$). The solvent was then distilled off under reduced pressure and the residue was subjected to silica gel column chromatography (2.5×30 cm) using ethyl acetate-dichloromethane (3:2) as the eluent. The desired fraction was concentrated, and ether and isopropyl ether (1:2) were added to the residue, whereupon compound 26 (0.07 g) was obtained as colorless prisms. m.p. 130°–131° C.

Elemental Analysis for $C_{15}H_{15}F_2N_5OS$ Calcd.: C, 46.99; H, 3.94; N, 18.26 Found: C, 46.77; H, 3.86; N, 18.06 $^1$H-NMR (CDCl$_3$) δ: 1.29(3H,d,J=7 Hz), 2.77(3H,s), 4.62(1H,q,J=7 Hz), 4.89(1H,d,J=13.8 Hz), 5.12(1H,d,J=13.8 Hz), 5.97(1H,s), 6.72–6.86(2H,m), 7.41–7.52(1H,m), 7.75(1H,s), 7.91(1H,s)

Example 25

A mixture of (2RS,3SR)-2-(2,4-difluorophenyl)-3-methyl-2-(1H-1,2,4-triazol-1-yl)methyloxirane (0.25 g), 2-imidazo[1,2-a]pyridinemethanethiol (0.25 g), 28% sodium methoxide-methanol (0.25 ml) and ethanol (7.5 ml) was refluxed for 2 hours. The reaction mixture was then concentrated under reduced pressure and the residue was diluted with methylene chloride (20 ml) and water (20 ml), and extracted with methylene chloride. The methylene chloride layer was dried over anhydrous sodium sulfate and concentrated under reduced pressure and the residue was subjected to silica gel chromatography (2.5 cm×7.0 cm) using ethyl acetate as the eluent. The desired fraction was concentrated to give compound 27 (0.25 g) as syrup. This syrup (0.19 g) was dissolved in diethyl ether (30 ml) followed by addition of hydrogen chloride in ethyl acetate. The resulting mixture was allowed to stand and the supernatant was removed by decantation. The residue was diluted with 30 ml of diethyl ether and the supernatant was removed by decantation again. To the residue was added diethyl ether-ethanol for crystallization to yield compound 27.dihydrochloride (0.17 g). m.p. 123°–125° C.

Elemental Analysis for $C_{20}H_{19}F_2N_5OS \cdot 2HCl \cdot \frac{1}{2}H_2O$
Calcd.: C, 48.30; H, 4.46; N, 14.08 Found: C, 48.38; H, 4.44; N, 13.92 $^1$H-NMR (DMSO-d$_6$) δ: 1.08(3H,d,J=8.2 Hz), 3.43(1H,q,J=8.2 Hz), 4.22(1H,d,J=14.4 Hz), 4.32(1H,d,J=14.4 Hz), 4.68(1H,d,J=14.6 Hz), 4.99(1H,d,J=14.6 Hz), 6.92(1H,m), 7.12(1H,m), 7.29(1H,m), 7.50(1H,m), 7.77(1H,s), 7.97(2H,m), 8.37(1H,s), 8.64(1H,s), 8.98(1H,d,J=6.6 Hz)

Example 26

To a solution of (2RS, 3RS)-2-(2,4-difluorophenyl)-3-mercapto-1-(1H-1,2,4-triazol-1-yl)-2-butanol (0.30 g) in ethanol (3.0 ml) was added 28% sodium methoxide-methanol (0.98 ml) at room temperature. After addition of 1-methyl-5-chloromethylimidazole hydrochloride (0.48 g), the mixture was stirred for 10 minutes. This reaction mixture was diluted with diethyl ether (30 ml) and water (30 ml) and extracted with diethyl ether (30 ml×3). The diethyl ether layers were combined, washed with saturated aqueous sodium chloride solution (20 ml) and dried over anhydrous sodium sulfate, followed by concentration under reduced pressure. To the residue was added diethyl ether, whereupon (2RS,3RS)-2-(2,4-difluorophenyl)-3-(1-methylimidazol-5-yl)methylthio-1-(1H-1,2,4-triazol-1-yl)-2-butanol (29:0.30 g) separated out as crystals. These crystals were recrystallized from ethanol-diethyl ether to give colorless needles (0.27 g). m.p. 159°–160° C.

Elemental Analysis for $C_{17}H_{19}F_2N_5OS$ Calcd.: C, 53.81; H, 5.05; N, 18.46 Found: C, 53.40; H, 5.23; N, 18.22 $^1$H-NMR (CDCl$_3$) δ: 1.13(3H,d,J=7.0 Hz), 3.20(1H,q,J=7.0 Hz), 3.73(3H,s), 3.82(1H,d,J=14.8 Hz), 3.91(1H,d,J=14.8 Hz), 4.45(1H,d,J=14.2 Hz), 4.83(1H,d,J=14.2 Hz), 5.00(1H,br.s), 6.72(2H,m), 7.01(1H,s), 7.35(1H,m), 7.48(1H,s), 7.72(1H,s), 7.77(1H,s)

Examples 27–37

In a manners like that described in Example 26, (2RS,3RS)-2-(2,4-difluorophenyl)-3-mercapto-1-(1H-1,2,4-triazol-1-yl)-2-butanol (Methylthiol derivative in Table 12) was reacted with the chloro-compounds in Table 12 to give compounds 25, 28, and 30 to 38.

TABLE 12

| Ex. No. | Starting compounds | Reaction conditions | Products |
|---|---|---|---|
| 27 | Methylthiol deriv. (0.17 g) 2-chloromethyl-4H-5,6-dihydrocyclopenta[d]thiazol hydrochloride (0.22 g) | Ethanol (10 ml) 28% sodium methylate-methanol solution (0.37 ml) 0.5 hour 80° C. | Compound 25 (0.16 g, 65%) mp. 75–77° C. $^1$H-NMR(CDCl$_3$)δ: 1.22(3H, d, J=7Hz), 2.48–2.61(2H, m), 2.85–2.95(4H, m), 3.50(1H, q, J=7Hz), 4.04(1H, d, J=15.6Hz), 4.23(1H, d, J=15.6Hz), 4.71(1H, d, J=14.2Hz), 5.04(1H, d, J=14.2Hz), 5.85(1H, s), 6.68–6.77(2H, m), 7.31–7.47(1H, m), 7.72(1H, s), 7.86(1H, s) Elemental Analysis for $C_{19}H_{20}F_2N_4OS_2$: Calcd.: C, 54.01; H, 4.77; N, 13.26 Found: C, 53.83; H, 4.72; N, 13.18 |
| 28 | Methylthiol deriv. (0.30 g) 4-Chloromethyl-1-methyl-imidazole hydrochloride (0.25 g) | Ethanol (6.0 ml) 28% sodium methylate-methanol solution (0.54 ml) 5 min. room temperature | Compound 28 (0.09 g, 23%) mp. 140–141° C. $^1$H-NMR(CDCl$_3$)δ: 1.29(3H, d, J=6.2Hz), 3.54(1H, q, J=6.2Hz), 3.61(1H, d, J=15.2Hz), 3.69(3H, s), 4.00(1H, d, J=15.2Hz), 4.74(1H, d, J=15.2Hz), 5.16(1H, d, J=15.2Hz), 6.7–6.8(3H, m), 7.4–7.6(2H, m), 7.68(1H, s), 7.87(1H, br.s), 8.07(1H, s) |
| 29 | Methylthiol deriv. (0.30 g) 2-Chloromethyl-1-(2,2,3,3-tetrafluoropropyl)imidazole hydrochloride | Ethanol (3.0 ml) 28% sodium methylate-methanol solution (1.0 ml) 7 min. room temperature | Compound 30 (0.31 g, 53%) 2-hydrochloride (powders) $^1$H-NMR(DMSO-d$_6$)δ: 1.09(3H, d, J=7.0Hz), 3.51(1H, q, J=7.0Hz), 4.41(1H, d, J=16Hz), 4.51(1H, d, J=16Hz), 4.63(1H, d, J=14.8Hz), 4.94(1H, d, J=14.8Hz), 5.31(2H, t, J=16Hz), 6.6–7.4(4H, m), 7.82(1H, s), 7.84(1H, s), 7.87(1H, s), 8.63(1H, s) |
| 30 | Methylthiol deriv. (0.25 g) 5-Chloromethyl-1-methyl-1H-1,2,4-triazole hydrochloride (0.13 g) | Ethanol (2.5 ml) 28% sodium methylate-methanol solution (0.36 ml) 30 min. room temperature | Compound 31 (0.25 g, 74%) mp. 108–109° C. $^1$H-NMR(CDCl$_3$)δ: 1.18(3H, d, J=7.0Hz), 3.48(1H, q, J=7.0Hz), 3.94(1H, d, J=15Hz), 3.95(3H, s), 4.06(1H, d, J=15Hz), 4.62(1H, d, J=14Hz), 4.94(1H, d, J=14Hz), 5.75(1H, s), 6.68–6.78(2H, m), 7.33–7.45(1H, m), 7.75(1H, s), 7.83(1H, s), 7.86(1H, s) Elemental Analysis for $C_{16}H_{18}F_2N_6OS$: Calcd.: C, 50.52; H, 4.77; N, 22.09 Found: C, 50.76; H, 4.83; N, 22.27 |
| 31 | Methylthiol deriv. (0.25 g) 3-Chloromethyl-1-methyl-1H-1,2,4-triazole hydrochloride (0.13 g) | Ethanol (2.5 ml) 28% sodium methylate-methanol solution (0.36 ml) 20 min. room temperature | Compound 32 (0.22 g, 65%) mp. 147–148° C. $^1$H-NMR(CDCl$_3$)δ: 1.25(3H, d, J=6.2Hz), 3.51(1H, q, J=6.2Hz), 3.86(1H, d, J=15Hz), 3.93(3H, s), 4.02(1H, d, J=15Hz), 4.72(1H, d, J=15.2Hz), 5.10(1H, d, J=15.2Hz), 6.08(1H, s), 6.69–6.81(2H, m), 7.39–7.51(1H, m), 7.72(1H, s), 7.89(1H, s), 8.04(1H, s) Elemental Analysis for $C_{16}H_{18}F_2N_6OS$: Calcd.: C, 50.52; H, 4.77; N, 22.09 Found: C, 50.59; H, 4.86; N, 21.90 |
| 32 | Methylthiol deriv. (0.25 g) 3-Chloromethyl-4-methyl-4H-1,2,4-triazole hydrochloride (0.13 g) | Ethanol (2.5 ml) 28% sodium methylate-methanol solution (0.36 ml) 15 min. room temperature | Compound 33 (0.21 g, 62%) mp. 197–198° C. $^1$H-NMR(CDCl$_3$)δ: 1.13(3H, d, J=7.0Hz), 3.48(1H, q, J=7.0Hz), 3.77(3H, s), 3.99(1H, d, J=15.2Hz), 4.08(1H, d, J=15.2Hz), 4.60(1H, d, J=14Hz), 4.82(1H, d, J=14Hz), 5.35(1H, s), 6.67–6.79(2H, m), 7.27–7.41(1H, m), 7.75(1H, s), 7.81(1H, s) 8.14(1H, s) Elemental Analysis for $C_{16}H_{18}F_2N_6OS$: Calcd.: C, 50.52; H, 4.77; N, 22.09 |

TABLE 12-continued

| Ex. No. | Starting compounds | Reaction conditions | Products |
|---|---|---|---|
| 33 | Methylthiol deriv. (0.25 g) 3-Chloromethyl-4-methyl-5-methylthio-4H-1,2,4-triazole hydrochloride (0.19 g) | Ethanol (2.5 ml) 28% sodium methylate-methanol solution (0.36 ml) 15 min. room temperature | Found: C, 50.32; H, 4.78; N, 22.09<br>Compound 34 (0.21 g, 55%) mp. 165–166° C.<br>$^1$H-NMR(CDCl$_3$)δ: 1.14(3H, d, J=7.0Hz), 2.74(3H, s), 3.48(1H, q, J=7.0Hz), 3.59(3H, s), 3.94(1H, d, J=15Hz), 4.05(1H, d, J=15Hz), 4.64(1H, d, J=14.2Hz), 4.84(1H, d, J=14.2Hz), 5.41(1H, s), 6.67–6.78(2H, m), 7.28–7.41(1H, m), 7.75(1H, s), 7.84(1H, s)<br>Elemental Analysis for C$_{17}$H$_{20}$F$_2$N$_6$OS$_2$: Calcd.: C, 47.87; H, 4.73; N, 19.70<br>Found: C, 47.93; H, 4.82; N, 19.76 |
| 34 | Methylthiol deriv. (0.25 g) 3-Chloromethyl-5H-6,7-dihydropyrrolo[1,2-c]imidazole hydrochloride (0.17 g) | Ethanol (2.5 ml) 28% sodium methylate-methanol solution (0.36 ml) 15 min. room temperature | Compound 35 (0.18 g, 50%) mp. 150–151° C.<br>$^1$H-NMR(CDCl$_3$)δ: 1.25(3H, d, J=6.6Hz), 2.61–2.73(2H, m), 2.87(2H, t, J=7.8Hz), 3.56(1H, q, J=6.6Hz), 3.62(1H, d, J=15.8Hz), 3.946(2H, t, J=7Hz), 4.05(1H, d, J=15.8Hz), 4.66(1H, d, J=15.2Hz), 4.91(1H, d, J=15.2Hz), 6.66(1H, s), 6.66–6.79(2H, m), 7.39–7.52(1H, m), 7.65(1H, s), 7.87(1H, br.s), 8.06(1H, s)<br>Elemental Analysis for C$_{19}$H$_{21}$F$_2$N$_5$OS: Calcd.: C, 56.28; H, 5.22; N, 17.27<br>Found: C, 56.47; H, 5.29; N, 17.14 |
| 35 | Methylthiol deriv. (0.3 g) 2-Chloromethyl-4,5-dimethylthiazole hydrochloride (0.25 g) | Ethanol (10 ml) 28% sodium methylate-methanol solution (0.43 ml) 30 min. 50° C. | Compound 36 (0.3 g, 69%) mp. 84–86° C.<br>$^1$H-NMR(CDCl$_3$)δ: 1.22(3H, d, J=7Hz), 2.36(6H, s), 3.51(1H, q, J=7Hz), 3.97(1H, d, J=15.4Hz), 4.15(1H, d, J=15.4Hz), 4.70(1H, d, J=14.2Hz), 5.03(1H, d, J=14.2Hz), 5.99(1H, s), 6.68–6.77(2H, m), 7.33–7.49(1H, m), 7.72(1H, s), 7.86(1H, s)<br>Elemental Analysis for C$_{18}$H$_{20}$F$_2$N$_4$OS$_2$: Calcd.: C, 52.67; H, 4.91; N, 13.65<br>Found: C, 52.32; H, 5.08; N, 13.42 |
| 36 | Methylthiol deriv. (0.3 g) 2-Chloromethyl-4-methylthiazole hydrochloride (0.23 g) | Ethanol (10 ml) 28% sodium methylate-methanol solution (0.43 ml) 30 min. 50° C. | Compound 37 (214 mg, 54%) mp. 67–69° C.<br>$^1$H-NMR(CDCl$_3$)δ: 1.22(3H, d, J=7Hz), 2.49(3H, s), 3.49(1H, q, J=7Hz), 4.08(1H, d, J=15.6Hz), 4.21(1H, d, J=15.6Hz), 4.67(1H, d, J=14Hz), 5.02(1H, d=14Hz), 5.74(1H, s) 6.64–6.86(3H, m), 7.33–7.48(1H, m), 7.74(1H, s), 7.82(1H, s) |
| 37 | Methylthiol deriv. (0.3 g) 2-Chloromethylthiazole hydrochloride (0.22 g) | Ethanol (10 ml) 28% sodium methylate-methanol solution (0.43 ml) 30 min. 50° C. | Compound 38 (0.26 g, 65%) oily substance<br>$^1$H-NMR(CDCl$_3$)δ: 1.20(3H, d, J=7Hz), 3.46(1H, q, J=7Hz), 4.16(1H, d, J=15.4Hz), 4.29(1H, d, J=15.4Hz), 4.66(1H, d, J=14.2Hz), 5.02(1H, d, J=14.2Hz), 6.63–6.77(2H, m), 7.33–7.48(2H, m), 7.74–7.77(2H, m), 7.82(1H, s)<br>This product (0.25 g) was treated with a hydrogen chloride-ethyl acetate solution to afford 38 hydrochloride as colorless powder (0.23 g). |

Example 38

A mixture of (2RS,3SR)-2-(2,4-difluorophenyl)-3-methyl-2-(1H-1,2,4-triazol-1-yl)methyloxirane (7 g), methyl 3-mercaptopropionate (30.8 ml) and 28% sodium methoxide-methanol (19.6 ml) in methanol (210 ml) was refluxed for 2 hours. Then, 28% sodium methoxide-methanol (9.8 ml) was added and the mixture was refluxed for another hour. Thereafter, methyl 3-mercaptopropionate was added and the mixture was further refluxed for 2 hours. The reaction mixture was then cooled, diluted with water (100 ml), neutralized with 5% aqueous phosphoric acid solution and extracted with methylene chloride (200 ml×2). The extract was dried over anhydrous sodium sulfate and the solvent was distilled off under reduced pressure. The residue was subjected to silica gel chromatography (4×50 cm) using ethyl acetate-hexane (3:1) as the eluent and the desired fraction was concentrated. To the residue was added ether to give compound 39 (5.5 g) as colorless needles. $^1$H-NMR (CDCl$_3$) δ: 1.17(3H,d,J=7.0 Hz), 1.96(1H,d,J=10.2 Hz), 3.45(1H,d,q,J=7.0 Hz,J=10.2 Hz), 4.77(1H,s), 4.82(1H,d,J=14.4 Hz), 5.01(1H,d,J=14.4 Hz), 6.70–6.81(2H,m), 7.33–7.45(1H,m), 7.79(1H,s), 7.80(1H,s) m.p. 145°–147° C.

Example 39

To dichloromethane (5 ml) was added (2RS,3RS)-2-(2,4-difluorophenyl)-3-mercapto-1-(1H-1,2,4-triazol-1-yl)-2-butanol (0.3 g), followed by addition of triethylamine (0.16 ml) under ice-cooling. Then, acetyl chloride (0.082 ml) was added dropwise and the mixture was stirred at room temperature for 30 minutes. The solvent was then distilled off under reduced pressure and the residue was subjected to silica gel chromatography (2.5×20 cm) using ethyl acetate-hexane (2:1) as the eluent. The desired fraction was concentrated and hexane was added to the residue to give compound 40 (0.2 g) as colorless needles. m.p. 73°–75° C.

Elemental Analysis for C$_{14}$H$_{15}$F$_2$N$_3$O$_2$ Calcd.: C, 51.37; H, 4.62; N, 12.84 Found: C, 51.19; H, 4.53; N, 12.84 $^1$H-NMR (CDCl$_3$) δ: 1.10(3H,d,J=7.2 Hz), 2.42(3H,s), 4.29(1H,q,J=7.2 Hz), 4.67(1H,d,J=15.2 Hz), 4.91(1H,d,J=15.2 Hz), 5.09(1H,s), 6.69–6.88(2H,m), 7.26–7.43(1H,m), 7.77(1H,s), 7.78(1H,s)

Example 40

A mixture of (2S,3R)-2-(2,4-difluorophenyl)-3-methyl-2-(1H-1,2,4-triazol-1-yl)methyloxirane (30 mg), methyl 3-mercaptopropionate (0.09 ml) and 28% sodium methoxide-methanol (0.08 ml) in methanol (2 ml) was refluxed for 2 hours, after which 28% sodium methoxide-methanol (0.04 ml) was added and the mixture was refluxed for another hour. Then, methyl 3-mercaptopropionate (0.04 ml) was added and the mixture was further refluxed for 2 hours. The reaction mixture was cooled, diluted with water (2 ml), neutralized with 5% aqueous phosphoric acid solution and extracted with methylene chloride (3 ml×2). The extract was dried over anhydrus sodium sulfate and the solvent was distilled off under reduced pressure. The residue was subjected to silica gel chromatography (1×5 cm) using ethyl acetate-hexane (3:1) as the eluent. The desired fraction was concentrated and the residue was crystallized from ethyl acetate-isopropyl ether to give (2S,3S)-2-(2,4-difluorophenyl)-3-mercapto-1-(1H-1,2,4-triazol-1-yl)-2-butanol (compound 42:11 mg) as colorless prisms.

$[\alpha]_D^{25} +55.7°$ (C=1.0, methanol) $^1$H-NMR (CDCl$_3$) δ: 1.17(3H,d,J=6.8 Hz), 1.96(1H,d,J=10.4 Hz), 3.39–3.54(1H,m), 4.75(1H,s), 4.81(1H,d,J=14.4 Hz), 5.01(1H,d,J=14.4 Hz), 6.69–6.81(2H,m), 7.33–7.46(1H,m), 7.79(1H,s), 7.80(1H,s) m.p. 175°–178° C.

To determine the enantiomer excess (ee), this product was S-acetylated (compound 44 in Example 43) and analyzed by high performance liquid chromatography using a chiral column (Chiralcel® OF, 0.46 cm×25 cm, Daicel Chemical) (mobile phase: hexane-isopropyl alcohol=7:3). At a flow rate of 1 ml/minute, compound 44 gave a substantially single peak at a retention time of 10 minutes and the enanthiomer excess was determined to be 97.4%.

[The corresponding racemic compound (compound 40 in Example 39) showed two peaks in a ratio of 1:1 at retention times of 10 and 17 minutes under the same conditions]

Example 41

In methanol (10 ml) were dissolved (2R,3S)-2-(2,4-difluorophenyl)-3-methyl-2-[(1H-1,2,4-triazol-1-yl)methyl]oxirane (0.40 g), methyl 3-mercaptopropionate (1.42 ml) and 28% sodium methoxide-methanol (1.25 ml) and the solution was refluxed. After 2 and after 3.5 hours, (0.53 ml and 0.32 ml each of) methyl 3-mercaptopropionate were added, and after 2.5 minutes, 28% sodium methoxide-methanol (0.63 ml) was added. At 4.5 hours after the beginning of heating, the oil bath was removed and the reaction mixture was cooled, neutralized with 1N hydrochloric acid (9.6 ml) and extracted with dichloromethane (100 ml). The extract was washed with saturated aqueous sodium chloride solution (20 ml) and dried over anhydrous sodium sulfate and the solvent was distilled off under reduced pressure. The residue was purified by silica gel chromatography (eluent: hexane-ethyl acetate=1:3). The desired fraction was concentrated and the resulting crystals were collected and washed with isopropyl ether to give (2R,3R)-2-(2,4-difluorophenyl)-3-mercapto-1-(1H-1,2,4-triazol-1-yl)-2-butanol (compound 43:0.22 g) as colorless needles. m.p. 176°–178° C.

$[\alpha]_D^{25} -56.8°$ (c=0.7, methanol) Elemental Analysis for $C_{12}H_{13}F_2N_3OS$ Calcd.: C, 50.52; H, 4.59; N, 14.73

Found: C, 50.81; H, 4.64; N, 14.64 $^1$H-NMR (CDCl$_3$) δ: 1.17 (3H,d,J=7.0 Hz), 1.96(1H,d,J=10.2 Hz), 3.45(1H,m), 4.76(1H,s), 4.82(1H,d,J=14.4 Hz), 5.01(1H,d,J=14.4 Hz), 6.74(2H,m), 7.33–7.45(1H,m), 7.79(2H,s)

To determine its enantiomer excess (ee), this product was S-acetylated (compound 45 in Example 44) and analyzed by high performance liquid chromatography using a chiral column (Chiralcel® OF, 0.46 cm×25 cm, Daicel Chemical) (mobile phase: hexane-isopropyl alcohol=7:3). At a flow rate of 1 ml/minute, compound 45 gave a substantially single peak at a retention time of 17 minutes and the enanthiomer excess was determined to be 99.7%. [The corresponding racemic compound (compound 40 in Example 39) showed two peaks in a ratio of 1:1 at retention times of 10 and 17 minutes under the same conditions]

Example 42

To dichloromethane (1 ml) was added (2S,3S)-2-(2,4-difluorophenyl)-3-mercapto-1-(1H-1,2,4-triazol-1-yl)-2-butanol (3 mg), followed by addition of a dichloromethane solution of triethylamine (10%, 16 μl) with ice-cooling. Then, a dichloromethane solution of acetyl chloride (10%, 8.2 μl) was added and the mixture was stirred at room temperature for 30 minutes. The solvent was then distilled off under reduced pressure and the residue was subjected to silica gel chromatography (1×1 cm) using ethyl acetate-hexane (2:1) as the eluent. The desired fraction was concentrated to give (2S,3S)-3-acetylthio-2-(2,4-difluorophenyl)-1-(1H-1,2,4-triazol-1-yl)-2-butanol (compound 44:1.2 mg) as a colorless solid.

Example 43

In dichloromethane (1.5 ml) was dissolved (2R,3R)-2-(2,4-difluorophenyl)-3-mercapto-1-(1H-1,2,4-triazol-1-yl)-2-butanol (60 mg), followed by addition of triethylamine (33 ml) and acetyl chloride (13 ml) under ice-cooling. The mixture was then stirred at room temperature for 30 minutes, and then the solvent was distilled off under reduced pressure. The residue was purified by silica gel chromatography (eluent: hexane-ethyl acetate=1:2) and the desired fraction was concentrated to give (2R,3R)-3-acetylthio-2-(2,4-difluorophenyl)-1-(1H-1,2,4-triazol-1-yl)-2-butanol (compound 45:59 mg) as a colorless solid.

$^1$H-NMR (CDCl$_3$) δ: 1.11(3H,d,J=7.2 Hz), 2.42(3H,s), 4.31(1H,d,J=7.2 Hz), 4.67(1H,d,J=14.4 Hz), 4.92(1H,d,J=14.4 Hz), 5.11(1H,d,J=1.8 Hz), 6.69–6.88(2H,m), 7.27–7.43(1H,m), 7.78(2H,s)

The enantiomer excess of this product was determined to be 99.7 %.

Examples 44–53

In a manner like that described in Example 26, (2RS,3RS)-2-(2,4-difluorophenyl)-3-mercapto-1-(1H-1,2,4-triazol-1-yl)-2-butanol [(2RS,3RS)-methylthiol derivative in Table 13] was reacted with the chlorocompounds Table 13 to give compounds 46–49, 51–55 and 59.

TABLE 13

| Ex. No. | Starting compounds | Reaction conditions | Products |
|---|---|---|---|
| 44 | (2RS,3RS)-Methylthiol deriv. | Ethanol (2.5 ml) 28% sodium | Compound 46 (0.20 g, 57%): Colorless prisms (recrystallized from |

TABLE 13-continued

| Ex. No. | Starting compounds | Reaction conditions | Products |
|---|---|---|---|
|  | (0.25 g) 2-Chloromethyl-1-ethyl-imidazole hydrochloride (0.16 g) | methylate-methanol solution (0.36 ml) 15 min. 20° C. | diethyl ether mp. 121–122° C. $^1$H-NMR(CDCl$_3$)δ: 1.24(3H, d, J=6.6Hz), 1.46(3H, t, J=7.2Hz), 3.55(1H, q, J=6.6Hz), 3.75(1H, d, J=15.6Hz), 4.00(2H, q, J=7.2Hz), 4.07(1H, d, J=15.6Hz), 4.60(1H, d, J=15.2Hz), 4.85(1H, d, J=15.2Hz), 6.68–6.80(2H, m), 6.91(1H, d, J=1.2Hz), 7.01(1H, d, J=1.2Hz), 7.41(1H, br.s), 7.43–7.52(1H, m), 7.67(1H, s), 8.01(1H, s) |
| 45 | (2RS,3RS)-Methylthiol deriv. (0.25 g) 2-Chloromethyl-1-isopropyl imidazole hydrochloride (0.17 g) | Ethanol (2.5 ml) 28% sodium methylate-methanol solution (0.36 ml) 13 min. 20° C. | Compound 47 (0.24 g, 67%): Colorless prisms (recrystallized from diethylether-hexane) mp. 95–96° C. $^1$H-NMR(CDCl$_3$)δ: 1.23(3H, d, J=6.4Hz), 1.47(3H, d, J=6.6Hz), 1.48(3H, d, J=6.8Hz), 3.55(1H, q, J=6.4Hz), 3.77(1H, d, J=15.4Hz), 4.08(1H, d, J=15.4Hz), 4.44(1H, sep., J=6.6Hz), 4.63(1H, d, J=15.2Hz), 4.83(1H, d, J=15.2Hz), 6.68–6.79(2H, m), 6.97(1H, d, J=1.4Hz), 7.02(1H, d, J=1.4Hz), 7.38(1H, br.s), 7.38–7.52(1H, m), 7.66(1H, s), 8.01(1H, s) |
| 46 | (2RS,3RS)-Methylthiol deriv. (0.25 g) 2-Chloromethyl-1-(2-fluoroethyl)-imidazole hydrochloride (0.18 g) | Ethanol (2.5 ml) 28% sodium methylate-methanol solution (0.36 ml) 10 min. 20° C. | Compound 48 (0.28 g, 65%): Dihydrochloride, colorless needles (recrystallized from ethanol-diethyl ether) mp. 113–115° C. $^1$H-NMR(CDSO-d$_6$)δ: 1.06(3H, d, J=6.8Hz), 3.49(1H, q, J=6.8Hz), 4.38(1H, d, J=15.4Hz), 4.50(1H, d, J=15.4Hz), 4.58–5.03(6H, m), 6.89–7.30(3H, m), 7.75(1H, d, J=2.0Hz), 7.78(1H, s), 7.89(1H, s), 8.66(1H, s), 8.5(1H, br.) |
| 47 | (2RS,3RS)-Methylthiol deriv. (0.25 g) 2-Chloromethyl-1-(2,2,2-trifluoroethyl)imidazole hydrochloride (0.21 g) | Ethanol (2.5 ml) 28% sodium methylate-methanol solution (0.36 ml) 10 min. 20° C. | Compound 49 (0.13 g, 28%): Dihydrochloride, colorless needles (recrystallized from methanol) mp. 115–118° C. $^1$H-NMR(CDSO-d$_6$)δ: 1.06(3H, d, J=7.0Hz), 3.52(1H, q, J=7.0Hz), 4.41(1H, d, J=15.4Hz), 4.52(1H, d, J=15.4Hz), 4.63(1H, d, J=14.2Hz), 4.91(1H, d, J=14.2Hz), 5.48(1H, q, J=8.8Hz), 6.4(1H, br.), 6.89–7.33(3H, m), 7.84(3H, s), 8.55(1H, s) |
| 48 | (2RS,3RS)-Methylthiol deriv. (0.25 g) 2-Chloromethyl-1-cyclopropyl-methyl imidazole hydrochloride (0.18 g) | Ethanol (2.5 ml) 28% sodium methylate methanol solution (0.36 ml) 10 min. 20° C. | Compound 51 (0.29 g, 78%): Colorless needles (recrystallized from diethyl ether) mp. 118–121° C. $^1$H-NMR(CDCl$_3$)δ: 0.38(2H, m), 0.70(2H, m), 1.17(1H, m), 1.23(3H, d, J=7.2Hz), 3.55(1H, q, J=7.2Hz), 3.77(1H, d, J=15.4Hz), 3.79(2H, d, J=6.8Hz), 4.07(1H, d, J=15.4Hz), 4.59(1H, d, J=14.4Hz), 4.85(1H, d, J=14.4Hz), 6.68–6.79(2H, m), 7.02(2H, s), 7.40(1H, br.), 7.40–7.52(1H, m), 7.67(1H, s), 8.01(1H, s) |
| 49 | (2RS,3RS)-Methylthiol deriv. (0.5 g) 4-Chloromethyl-2-methyl thiazole hydrochloride (0.39 g) | Ethanol (15 ml) 28% sodium methylate methanol solution (0.72 ml) 0.5 hour 50° C. | Compound 52 (0.45 g, 65%): $^1$H-NMR(CDCl$_3$)δ: 1.24(3H, d, J=6.8Hz), 2.78(3H, s), 3.52(1H, q, J=6.8Hz), 3.82(1H, d, J=14.6Hz), 4.07(1H, d, J=14.6Hz), 4.72(1H, d, J=14.4Hz), 5.08(1H, d, J=14.4Hz), 6.26(1H, s), 6.68–6.78(2H, m), 6.93(1H, s), 7.38–7.51(1H, m), 7.72(1H, s), 7.83(1H, s) This product was processed, in ethyl acetate, with hydrogen chloride-ethyl acetate to afford hydrochloride (0.28 g), mp. 144–146° C. Elemental Analysis for C$_{17}$H$_{18}$F$_2$N$_4$OS$_2$•2HCl•H$_2$O: Calcd.: C, 41.89; H, 4.55; N, 11.49 Found: C, 42.11; H, 4.29; N, 11.32 |
| 50 | (2RS,3RS)-Methylthiol deriv. (0.4 g) 5-Chloromethyl-2-methyl thiazole hydrochloride (0.3 g) | Ethanol (10 ml) 28% sodium methylate methanol solution (0.58 ml) 0.5 hour 50° C. | Compound 53 (0.4 g, 72%): $^1$H-NMR(CDCl$_3$)δ: 1.15(3H, d, J=7Hz), 2.70(3H, s), 3.21(1H, q, J=7Hz), 3.98(1H, d, J=14.6Hz), 4.08(1H, d, J=14.6Hz), 4.67(1H, d, J=14.2Hz), 4.92(1H, s), 4.99(1H, d, J=14.2Hz), 6.65–6.81(2H, m), 7.28–7.41(1H, m), 7.47(1H, s), 7.76(1H, s), 7.77(1H, s) mp. 123–124° C. |
| 51 | (2RS,3RS)-Methylthiol deriv. (0.25 g) 2-Chloromethyl-1-(2,2-difluoroethyl)imidazole hydrochloride (0.19 g) | Ethanol (2.5 ml) 28% sodium methylate methanol solution (0.36 ml) 10 min. 20° C. | Compound 54 (0.34 g, 77%): Dihydrochloride, colorless needles (recrystallized from ethanol-diethyl ether) mp. 112–114° C. $^1$H-NMR(CMSO-d$_6$)δ: 1.18(3H, d, J=7.0Hz), 3.49(1H, q, J=7.0Hz), 3.85(1H, d, J=15.2Hz), 4.10(1H, d, J=15.2Hz), 4.36(2H, t, J=14.2Hz, d, J=3.6Hz), 4.62(1H, d, J=14.2Hz), 4.88(1H, d, J=14.2Hz), 6.06(1H, t, J=55Hz, t, J=3.6Hz), 6.52(1H, s), 6.69–6.78(2H, m), 6.97(1H, s), 7.05(1H, d, J=1.2Hz), 7.37–7.49(1H, m), 7.71(1H, s), 7.19(1H, s) |
| 52 | (2RS,3RS)-Methylthiol deriv. (0.25 g) 2-Chloromethyl-1-cyclopropyl imidazole hydrochloride (0.17 g) | Ethanol (2.5 ml) 28% sodium methylate methanol solution (0.36 ml) 10 min. 20° C. | Compound 55 (0.26 g, 72%): Colorless prisms (recrystallized from diethyl ether) mp. 105–106° C. $^1$H-NMR(CDCl$_3$)δ: 0.95–1.17(4H, m), 1.26(3H, d, J=7.0Hz), 3.21–3.32(1H, m), 3.59(1H, q, J=7.0Hz), 3.94(1H, d, J=15.4Hz), 4.03(1H, d, J=15.4Hz), |

TABLE 13-continued

| Ex. No. | Starting compounds | Reaction conditions | Products |
|---|---|---|---|
| | | | 4.63(1H, d, J=14.8Hz), 4.88(1H, d, J=14.8Hz), 6.67–6.80(2H, m), 6.87(1H, d, J=1.4Hz), 6.93(1H, d, J=1.4Hz), 7.40–7.53(1H, m), 7.65(1H, s), 7.69(1H, s), 8.03(1H, s) |
| 53 | (2RS,3RS)-Methylthiol deriv. (0.12 g) 2-Chloromethyl-1-(1,3-difluoro-2-propyl) imidazole hydrochloride (0.10 g) | Ethanol (2.0 ml) 28% sodium methylate methanol solution (0.17 ml) 10 min. 20° C. | Compound 59 (0.15 g, 79%): Colorless needles (recrystallized from diethyl ether) mp. 141–142° C. $^1$H-NMR(CDCl$_3$)$\delta$: 1.16(3H, d, J=6.4Hz), 3.47(1H, q, J=6.4Hz), 3.88(1H, d, J=15.2Hz), 4.11(1H, d, J=15.2Hz), 4.61–4.94(1H, m), 6.28(1H, s), 6.67–6.79(2H, m), 7.06(1H, d, J=1.4Hz), 7.11(1H, d, J=1.4Hz), 7.36–7.48(1H, m), 7.72(1H, s), 7.89(1H, s) |

Example 54

A mixture of (2RS,3SR)-2-(2,4-difluorophenyl)-1-methyl-2-(1H-1,2,4-triazol-1-ylmethyl)oxirane (0.18 g), 1-methyl-2-(2-mercaptoethyl)imidazole (0.10 g), 28% sodium methoxide-methanol (0.20 ml) and ethanol (5.4 ml) was refluxed for 1 hour. The reaction mixture was then diluted with water (10 ml) and extracted with diethyl ether (20 ml×3). The extract was washed with saturated aqueous sodium chloride solution (10 ml), dried over anhydrous magnesium sulfate and concentrated under reduced pressure. To the residue was added diethyl ether to give crude crystals of (2RS,3RS)-2-(2,4-difluorophenyl)-3-[2-(1-methylimidazol-2-yl)ethyl]thio-1-(1H-1,2,4-triazol-1-yl)-2-butanol (0.098 g). The crystals were recrystallized from ethyl acetate to give 0.050 g of the compound (compound 50). m.p. 175°–176° C.

$^1$H-NMR (CDCl$_3$) $\delta$: 1.20(3H,d,J=6.6 Hz), 2.7–3.6(5H,m), 3.60(3H,s), 4.71(1H,d,J=14.2 Hz), 5.03(1H,d,J=14.2 Hz), 6.67–6.77(2H,m), 6.87(1H,s), 7.08(1H,s), 7.43–7.55(1H,m), 7.69(1H,s), 7.82(1H,s), 8.03(1H,s) Elemental Analysis for C$_{18}$H$_{21}$F$_2$N$_5$OS Calcd.: C, 54.95; H, 5.38; N, 17.80 Found: C, 55.04; H, 5.39; N, 17.62.

Example 55

To a solution of (2RS,3RS)-2-(2,4-difluorophenyl)-3-mercapto-1-(1H-1,2,4-triazol-1-yl)-2-butanol (0.060 g), 4-bromomethyl-5-methyl-2-oxo-1,3dioxol (0.049 g) in N,N-dimethylformamide (2.0 ml) was added anhydrous potassium carbonate (0.20 g) at −20° C. and the mixture was stirred for 10 minutes. To the reaction mixture were added ethyl acetate (10 ml) and water (10 ml), and organic layer was separated. The mixture was further extracted with ethyl acetate (10 ml×2). The organic layers were combined, washed with saturated aqueous sodium chloride solution (10 ml), dried over anhydrous sodium sulfate and concentrated under reduced pressure. The residue was subjected to silica gel chromatography (1 cm×5 cm), and elution was carried out with ethyl acetate-hexane (1:1). The desired fraction was concentrated and the residue was crystallized from chloroform-diethyl ether to give (2RS,3RS)-2-(2,4-difluorophenyl)-3-(5-methyl-2-oxo-1,3-dioxol-4-yl)methylthio-1-(1H-1,2,4-triazol-1-yl)-2-butanol (compound 56, 0.065 g). m.p. 173°–174° C.

$^1$H-NMR (CDCl$_3$) $\delta$: 1.20(3H,d,J=7.0 Hz), 2.15(3H,s), 3.32(1H,q,J=7.0 Hz), 3.67(1H,d,J=15.4 Hz), 3.77(1H,d ,J=15.4 Hz), 4.83(1H,d,J=14.2 Hz), 5.04(1H,d ,J=14.2 Hz), 5.11(1H,d,J=1.6 Hz), 6.68–6.79(2H,m ), 7.30–7.42(1H,m), 7.79(1H,s), 7.80(1H,s ) Elemental Analysis for C$_{17}$H$_{17}$F$_2$N$_3$O$_4$S Calcd.: C, 51.38; H, 4.31; N, 10.57 Found: C, 51.39; H, 4.30; N, 10.55.

Example 56

In 1,2-dichloroethane (5.0 ml) was dissolved N-(2-pyrazinylmethyl)chloroacetamide (0.50 g) followed by addition of phosphorus oxychloride (5.0 ml) at room temperature. The mixture was refluxed for 40 minutes and, then, concentrated under reduced pressure. The residue was dissolved in methanol (1.0 ml) followed by addition of diethyl ether to give crude 3-chloromethylimidazo[1,5-a]pyrazine hydrochloride as powder (0.46 g). This powder (0.18 g) was added to a mixture of (2RS,3RS)-2-(2,4-difluorophenyl)-3-mercapto-1-(1H-1,2,4-triazol-1-yl)-2-butanol (0.25 g), ethanol (2.5 ml) and 28% sodium methoxide-methanol (0.36 ml) at room temperature and the mixture was stirred for 7 minutes. The reaction mixture was poured into water (20 ml) and extracted with ethyl acetate (20 ml×3). The organic layers were combined, washed with saturated aqueous sodium chloride solution (10 ml), dried over anhydrous magnesium sulfate and concentrated under reduced pressure. The residue was subjected to silica gel chromatography (2 cm×8 cm), and elution was carried out with methanol-methylene chloride (5:95). The desired fractions were combined and further subjected to silica gel chromatography (2 cm×8 cm) and elution was carried out with methylene chloride-ethylacetate (1:2). The desired fractions were combined and concentrated. To the residue were added to a mixture of diethyl ether and hexane, whereupon (2RS,3RS)-2-(2,4-difluorophenyl)-3-(imidazo[1,5-a]pyradin-3-yl)methylthio-1-(1H-1,2,4-triazol-1-yl)-2-butanol (compound 5.7:0.02 g) was separated out as a colorless powder.

$^1$H-NMR (CDCl$_3$) $\delta$: 1.14(3H,d,J=7.0 Hz), 3.34(1H,q,J=7.0 Hz), 4.28(1H,d,J=15 Hz), 4.38(1H,d,J=15 Hz), 4.49(1H,d,J=14.4 Hz), 4,86(1H,d,J=14.4 Hz), 5.56(1H,br.s), 6.66–6.77(2H,m), 7.27–7.44(1H,m), 7.62(1H,d,J=5.0 Hz), 7.74(1H,s), 7.77(1H,s), 7.80(1H,s), 7.86(1H,d,J=5.0 Hz), 9.01(1H,d,J=1.4 Hz) SIMS(m/z): 417 (MH+)

Example 57

A methanol (25 ml) solution containing (2RS,3RS)-2-(2,4-difluorophenyl)-3-methyl-2-(1H-1,2,4-triazol-1-yl)methyloxirane (1.1 g), methyl 3-mercaptopropionate (2.5 ml), 28% sodium methoxide-methanol (2.4 ml) was refluxed for 3 hours. After addition of 28% sodium methoxide-methanol (1.2 ml) the mixture was refluxed for 2 hours. After cooling, the reaction mixture was diluted with water (25 ml), neutralized with 5% aqueous phosphoric acid solution and extracted with methylene chloride (25 ml×3). The extract was dried over anhydrous sodium sulfate and concentrated under reduced pressure. The residue was subjected to silica gel chromatography (4×50 cm) and elution was carried out with ethyl acetate-hexane (3:1). The desired fraction was concentrated, and ether was added to the residue to give compound 60 (0.5 g) as colorless needles.

The above product (0.5 g) was recrystallized from ethyl acetate (40 ml) to give colorless prisms (0.2 g) of compound 60. m.p. 107°–109° C.

$^1$H-NMR (CDCl$_3$) δ: 1.47(3H,d,J=7 Hz), 2.11(1H,d,J=8.4 Hz), 3.61(1H,q,J=7 Hz), 6.42(1H,d,J=14.2 Hz), 4.71(1H,d,J=14.2 Hz), 5.84(1H,s ), 6.81–6.92(1H,m), 6.99–7.15(1H,m), 7.21–7.37 (1H,m), 7.65(1H,s), 8.23(1H,s) Elemental Analysis for C$_{12}$H$_{13}$F$_2$N$_3$OS Calcd.: C, 50.52; H, 4.59; N, 14.73 Found: C, 50.31; H, 4.59; N, 14.60.

Example 58

To dichloromethane (5 ml) was added (2RS,3SR)-2-(2,4-difluorophenyl)-3-mercapto-1-(1H-1,2,4-triazol-1-yl)-2-butanol (0.35 g), followed by addition of triethylamine (0.18 ml) under ice-cooling. Then, acetyl chloride (0.1 ml) was added dropwise and the mixture was stirred at room temperature for 30 minutes. The solvent was then distilled off under reduced pressure and the residue was subjected to silica gel chromatography (2.5×20 cm), and elution was carried out with ethyl acetate-hexane (2:1). The desired fraction was concentrated, and hexane was added to the residue to give compound 61 (0.22 g) as colorless needles. m.p. 128°–130° C.

$^1$H-NMR (CDCl$_3$) δ: 1.57(3H,d,J=7 Hz), 2.14(3H,s), 4.22(1H,q,J=7 Hz), 4.55(1H,d,J=14 Hz), 4.99(1H,d,J=14 Hz), 5.13(1H,s), 6.62–6.79(2H,m), 7.31–7.42(1H,m), 7.77(1H,s), 7.87(1H,s) Elemental Analysis for C$_{14}$H$_{15}$F$_2$N$_3$O$_2$S Calcd.: C, 51.37; H, 4.62; N, 12.84 Found: C, 51.32; H, 4.61; N, 12.71.

Example 59

In dichloromethane (5 ml) was dissolved (2R,3R)-2-(2,4-difluorophenyl)-3-mercapto-1-(1H-1,2,4-triazol-1-yl)-2-butanol (143 mg), followed by addition of triethylamine (0.076 ml) and isobutyryl chloride (58.6 mg) under ice-cooling. The mixture was stirred at room temperature for 15 minutes, and then the solvent was distilled off under reduced pressure. The residue was purified by silica gel chromatography (eluent:hexane-ethyl acetate=1:2). The desired fraction was concentrated to give (2R,3R)-2-(2,4-difluorophenyl)-3-isobutyrylthio-1-(1H-1,2,4-triazol-1-yl)-2-butanol (compound 62, 140 mg) as a colorless syrup. This product was treated with 4N hydrochloric acid (in ethyl acetate) to give the hydrochloride, which was then crystallized from ether to give compound 62 hydrochloride (156 mg) as a colorless powder. m.p. 129°–138° C.

$^1$H-NMR (CDCl$_3$) δ: 1.03(3H,d,J=7.0 Hz), 1.18(6H,dd,J=6.8 Hz,J=4.0 Hz), 2.84(1H,m), 4.33(1H,q,J=7.0 Hz), 4.67(2H,s), 6.92(1H,m), 7.08–7.30(2H,m), 7.76(1H,s), 8.42(1H,s)

Example 60

Methyl 3-mercaptopropionate (0.88 ml) was added to N,N-dimethylformamide (14 ml) containing 60% sodium hydride in oil (0.32 g) under ice-cooling. After 5 minutes, a solution of 2-(2,4-difluorophenyl)-2-[1-(1H-1,2,4-triazol-1-yl)ethyl]oxirane (0.67 g) in N,N-dimethylformamide (3.5 ml) was added over 5 minutes with ice-cooling. After 15 minutes, the reaction mixture was poured into water (150 ml), neutralized with hydrochloric acid and extracted with ethyl acetate (50 ml×3). The organic layers were combined, washed with saturated aqueous sodium chloride solution (30 ml× 2), dried over anhydrous sodium sulfate and concentrated under reduced pressure. The residue was subjected to silica gel chromatography (3 cm×10 cm) and elution was carried out with ethyl acetate-hexane (1:1). The desired fraction was concentrated and diethyl ether was added to the residue to give crude crystals (0.25 g) of 2-(2,4-difluorophenyl)-1-mercapto-3-[(1H)-1,2,4-triazol-1-yl]-2-butanol (of low polarity; compound 116, diastereomer B). The crystals were recrystallized from a mixture of chloroform and diethyl ether to give 0.21 g of compound 116. The mother liquor of the above crude crystals was further subjected to silica gel chromatography (2 cm×12 cm) and elution was carried out with ethyl acetate-hexane (1:1). The desired fraction was concentrated and diethyl ether and hexane were added to the residue to give crude crystals (0.25 g) of 2-(2,4-difluorophenyl)-1-mercapto-3-[(1H)-1,2,4-triazol-1-yl]-2-butanol (of high polarity; compound 115, diastereomer A). The crystals were recrystallized from a mixture of chloroform and diethyl ether to give crystals of compound 115 (0.11 g). Compound 115 (diastereomer A) m.p. 112°–117° C. (colorless prism)

$^1$H-NMR (CDCl$_3$) δ: 1.19(1H,t,J=8.2 Hz), 1.69 (3H,d,J=7.0 Hz), 3.05(1H,d,J=8.2 Hz,d,J=14 Hz), 3.31 (1H,d,J=8.2 Hz,d,J=14 Hz), 4.55(1H,s), 5.06 (1H,q,J=7.0 Hz), 6.68–6.79(2H,m), 7.23–7.35 (1H,m), 7.73(1H,s), 7.88(1H,s) Compound 116 (diastereomer B) m.p. 183°–184° C.

$^1$H-NMR (CDCl$_3$) δ: 0.93(1H,d,J=6.8 Hz,d,J=10.2 Hz), 1.36(3H,d,J=7.0 Hz), 2.18(1H,d,J=14 Hz,d,J=10.2 Hz), 3.28(1H,d,J=6.8 Hz,d,J=14 Hz), 4.19(1H,s), 5.09(1H,q,J=7.0 Hz), 6.80–7.04(2H,m), 7.67–7.79(1H,m), 7.99(1H,s), 8.29(1H,s)

Example 61

To ethanol (25 ml) were added (2R,3R)-2-(2,4-difluorophenyl)-3-mercapto-1-(1H-1,2,4-triazol-1-yl)-2-butanol (0.9 g) and 4-chloromethyl-2-methylthiazole hydrochloride (0.7 g), followed by addition of 28% sodium methoxide-methanol (1.3 ml) with constant stirring at room temperature. The mixture was further stirred at room temperature for 30 minutes, and then ethyl acetate (100 ml) and water (100 ml) were added. The ethyl acetate layer was separated and the aqueous layer was extracted with ethyl acetate (50 ml ). The ethyl acetate layers were combined, washed with water (50 ml), dried (MgSO$_4$) and concentrated under reduced pressure. The residue was purified by silica gel column chromatography (2.9×100 cm; eluent:ethyl acetate-acetone=4:1). The desired fraction was concentrated to give compound 107 (0.8 g) as a colorless oil.

$^1$H-NMR (CDCl$_{33}$) δ: 1.24(3H,d,J=7.2 Hz), 2.79(3H,s), 3.49(1H,q,J=7.2 Hz), 3.82(1H,d,J=14.6 Hz), 4.07(1H,d,J=14.6 Hz), 4.68(1H,d,J=14.6 Hz), 5.08(1H,d,J=14.6 Hz), 6.25(1H,s), 6.69–6.78(2H,m), 6.93(1H,s), 7.36–7.50(1H,m), 7.72(1H,s), 7.83(1H,s)

This product (0.8 g) was treated with 4N HCl-ethyl acetate to give the hydrochloride as colorless crystals (0.64 g). m.p. 165°–167° C.

[α]$_D^{23}$ −83.1° (c=1.0, methanol) Elemental Analysis for C$_{17}$H$_{18}$F$_2$N$_4$OS$_2$.2HCl.½H$_2$O Calcd.: C, 42.68; H, 4.42; N, 11.71 Found: C, 42.64; H, 4.37; N, 11.59.

Example 62

In ethanol (7.5 ml) was dissolved (2R,3R)-2-(2,4-difluorophenyl)-3-mercapto-1-(1H-1,2,4-triazol-1-yl)-2-butanol (0.74 g), followed by addition of 28% sodium methoxide-methanol (1.06 ml) and 2-chloromethyl-1-cyclopropylimidazole hydrochloride (0.5 g) with stirring at room temperature. The mixture was stirred at room temperature for 10 minutes, then diluted with water (20 ml) and extracted with ethyl ether (20 ml×3). The extract was washed with saturated aqueous sodium chloride solution, dried (MgSO4) and concentrated under reduced pressure. The residue was purified by silica gel column chromatography (ethyl acetate→ethyl acetate-methanol=95:5) and crystallized from ethyl ether to give compound 110 (0.82 g) as colorless prisms.

$[\alpha]_D^{23}$ −119.5° (c=1.0, methanol) m.p. 127°–128° C. Elemental Analysis for $C_{19}H_{21}F_2N_5O_1S_1$ Calcd.: C, 56.28; H, 5.22; N, 17.27 Found: C, 56.34; H, 5.26; N, 17.14 $^1$H-NMR (CDCl3) δ: 0.95–1.17(4H,m), 1.26(3H,d,J=7.0 Hz), 3.20–3.33(1H,m), 3.60(1H,q,J=7.0 Hz), 3.94(1H,d,J=15.4 Hz), 4.03(1H,d,J=15.4 Hz), 4.62(1H,d,J=14.2 Hz), 4.88(1H,d,J=14.2 Hz), 6.67–6.80(2H,m), 6.87(1H,s), 6.93(1H,s), 7.40–7.53(1H,m), 7.65(1H,s), 7.68(1H,s), 8.03(1H,s)

Example 63

In N,N-dimethylformamide (30 ml) were dissolved (2R,3R)-2-(2,4-difluorophenyl)-3-mercapto-1-(1H-1,2,4-triazol-1-yl)-2-butanol (1.0 g) and 4-bromomethyl-5-methyl-1,3-dioxol-2-one (0.81 g) followed by addition of potassium carbonate (3.0 g) at room temperature with stirring. The mixture was further stirred for 7 minutes, then diluted with water (100 ml) and extracted with ethyl acetate (50 ml×3). The organic layers were combined, washed with saturated aqueous sodium chloride solution (30 ml×2), dried (MgSO4) and concentrated under reduced pressure. The residue was purified by silica gel column chromatography (ethyl acetate-hexane=1:1→2:1) and the resulting oil was crystallized from a mixture of chloroform and ethyl ether to give compound 111 (1.0 g) as colorless needles. m.p. 133°–134° C.

$[\alpha]_D^{23}$ −77.8° (c=1.0, methanol) Elemental Analysis for $C_{17}H_{17}F_2N_3O_4S_1$ Calcd.: C, 51.38; H, 4.31; N, 10.57 Found: C, 51.20; H, 4.35; N, 10.52 $^1$H-NMR (CDCl3) δ: 1.20(3H,d,J=7.2 Hz), 2.15(3H,s), 3.32 (1H,q,J=7.2 Hz), 3.67(1H,d,J=15.2 Hz), 3.77 (1H,d,J=15.2 Hz), 4.83(1H,d,J=14.2 Hz), 5.04(1H,d,J=14.2 Hz), 5.11(1H,d,J=1.4 Hz), 6.68–6.79(2H,m), 7.30–7.42(1H,m), 7.79(1H,s), 7.80(1H,s)

Example 64

(2R,3R)-2-(2,4-difluorophenyl)-3-mercapto-1-(1H-1,2,4-triazol-1-yl)-2-butanol (0.25 g) was dissolved in ethanol (2.5 ml), followed by addition of 28% sodium methoxide-methanol (0.36 ml) and 3-chloromethyl-4-cyclopropyl-4H-1,2,4-triazole hydrochloride (0.17 g) with stirring at room temperature. The mixture was stirred for 10 minutes, then diluted with saturated aqueous sodium chloride solution (3 ml) and extracted with ethyl acetate (10 ml×3). The organic layers were combined and dried (MgSO4) and the solvent was distilled off under reduced pressure. The residue was purified by silica gel column chromatography (methylene chloride:methanol=98:2→95:5→1:9) to give compound 114 (0.29 g) as a colorless oil.

$^1$H-NMR (CDCl3) δ: 1.0–1.1(4H,m), 1.18 (3H,d,J=6.8 Hz ), 3.28–3.40(1H,m), 3.57 (1H,q,J=6.8 Hz ), 4.04 (1H,d,J=15 Hz), 4.16 (1H,d,J=15 Hz), 4.64(1H,d,J=14.2 Hz), 4.84 (1H,d,J=14.2 Hz ), 5.58(1H,s), 6.66–6.80(2H,m), 7.30–7.43(1H,m), 7.73(1H,s), 7.86(1H,s), 8.12(1H,s)

The above product was dissolved in ethyl acetate followed by addition of hydrogen chloride-ethyl acetate. The precipitate was crystallized from ethanol-ethyl acetate to give compound 114 dihydrochloride (0.31 g) as a colorless powder.

$[\alpha]_D^{23}$ −75.6° (c=1.0, methanol)

Examples 65–75

In a manner like that described in Example 64, (2R,3R)-2-(2,4-difluorophenyl)-3-mercapto-1-(1H-1,2,4-triazol-1-yl)-2-butanol [in Table 14, simply referred to "(2R,3R)-methyl thiol deriv.] was allowed to react with the chloro-derivative shown in Table 14 to afford Compounds 78, 97, 99, 108, 109, 112, 121–125.

TABLE 14

| Ex. No. | Starting compounds | Reaction conditions | Products |
|---|---|---|---|
| 65 | (2R,3R)-Methylthiol deriv. (0.4 g) 5-Chloromethyl-2-methyl thiazole hydrochloride (0.3 g) | Ethanol (15 ml) 28% sodium methylate-methanol solution (0.58 ml) 15 min. 20° C. | Compound 108•dihydrochloride(0.45 g, 81%): Colorless powder (crystallized from ethanol-ethyl ether) mp. 52–54° C. $^1$H-NMR(DMSO-d6)δ: 1.02(3H, d, J=7Hz), 2.69(3H, s), 3.32(1H, q, J=7Hz), 4.02(1H, d, J=15Hz), 4.17(1H, d, J=15Hz), 4.61(1H, d, J=14Hz), 4.95(1H, d, J=14Hz), 6.82–6.94(1H, m), 7.06–7.28(2H, m), 7.67(1H, s), 7.88(1H, s), 8.65(1H, s). $[\alpha]_D^{23}$ −74.1° (c = 1.0, in methanol) |
| 66 | (2R,3R)-Methylthiol deriv. (0.4 g) 2-Chloromethyl-4-methyl thiazole hydrochoride (0.3 g) | Ethanol (15 ml) 28% sodium methylate methanol solution (0.57 ml) 15 min. 20° C. | Compound 99•dihydrochloride(0.36 g, 65%): Colorless powder (crystallized from a mixture of ethanol and ethyl ether) mp. 158–160° C. $^1$H-NMR(DMSO-d6)δ: 1.03(3H, d, J=7Hz), 2.37(3H, s), 3.55(1H, q, J=7Hz), 4.07(1H, d, J=15Hz), 4.21(1H, d, J=15Hz), 4.62(1H, d, J=14Hz), 4.95(1H, d, J=14Hz), 6.80–6.93(1H, m), 7.02–7.29(2H, m), 7.20(1H, s), 7.71(1H, s), 8.46(1H, s) $[\alpha]_D^{23}$ −70.0° (c = 1.0, in methanol) |
| 67 | (2R,3R)-Methylthiol deriv. (0.4 g) 2-Amino-4-chloromethyl thiazole hydrochoride (0.3 g) | Ethanol (15 ml) 28% sodium methylate-methanol solution (0.58 ml) 30 min. 20° C. | Compound 121•dihydrochloride(0.32 g, 57%): Colorless powder (crystallized from ethyl ether) mp. 178–180° C. $^1$H-NMR(DMSO-d6)δ: 1.03(3H, d, J=7Hz), 3.33(1H, q, J=7Hz), 3.83(1H, d, J=15Hz), 3.99(1H, d, J=15Hz), 4.61(1H, d, J=14Hz), 4.99(1H, d, J=14Hz), 6.02(2H, bs), 6.84(1H, s), 6.86–6.94(1H, m), 7.08–7.31(2H, m), 7.90(1H, s), 8.71(1H, s) |
| 68 | (2R,3R)-Methylthiol deriv. (0.05 g) 3-Chloromethyl-imidazo[1,5-a]pyrazine hydro- | Ethanol (5.0 ml) 28% sodium methylate-methanol solution (0.72 ml) 25 min. 20° C. | Compound 112•dihydrochloride(0.61 g, 70%): Colorless powder (crystallized from a mixture of ethanol and ethylether) mp. 102–105° C. $^1$H-NMR(DMSO-d6)δ: 0.99(3H, d, J=6.6Hz), |

TABLE 14-continued

| Ex. No. | Starting compounds | Reaction conditions | Products |
|---|---|---|---|
| | chloride (0.36 g) | | 3.52(1H, q, J=6.6Hz), 4.50(1H, d, J=14Hz), 4.55(1H, d, J=15Hz), 4.69(1H, d, J=15Hz), 4.85(1H, d, J=14Hz), 6.80–7.30(3H, m), 7.89(1H, d, J=5.4Hz), 8.12(1H, s), 8.62(1H, s), 8.89(1H, d, J=5.4Hz), 8.98(1H, s), 9.73(1H, s) SIMS(m/z): 417(MH$^+$) $[\alpha]_D^{23}$ −130.3° (c = 1.0, in methanol) |
| 69 | (2R,3R)-Methylthiol deriv. (0.60 g) 2-Chloromethyl-1-(2,2-difluoroethyl)imidazole hydrochloride (0.46 g) | Ethanol (6.0 ml) 28% sodium methylate methanol solution (0.86 ml) 25 min. 20° C. | Compound 109•dihydrochloride(0.88 g, 83%): Colorless prisms (crystallized from a mixture of ethanol and ethylether) mp. 105–110° C. $^1$H-NMR(DMSO-d$_6$)δ: 1.07(3H, d, J=7Hz), 3.51(1H, q, J=7Hz), 4.42(1H, d, J=15Hz), 4.55(1H, d, J=15Hz), 4.65(1H, d, J=14Hz), 4.94(2H, dt, J=3Hz, 14Hz), 4.97(1H, d, J=14Hz), 6.60(1H, tt, J=3Hz, 55Hz), 6.80–7.30(3H, m), 7.79(2H, s), 8.00(1H, s), 8.85(1H, s) Elemental Analysis for C$_{18}$H$_{19}$F$_4$N$_5$OS•2HCl: Calcd.: C, 43.04; H, 4.21; N, 13.94 Found: C, 43.06; H, 4.23; N, 13.96 $[\alpha]_D^{25}$ −51.8° (c = 1.0, in methanol) |
| 70 | (2R,3R)-Methylthiol deriv. (0.7 g) 4-Chloromethyl-2-trifluoromethyl thiazole (0.66 g) | Ethanol (15 ml) 28% sodium methylate methanol solution (0.46 ml) 30 min. 20° C. | Compound 122 hydrochloride (0.9 g, 82%): Colorless powder (crystallized from ethyl ether) mp. 55–58° C. $^1$H-NMR(DMSO-d$_6$)δ: 1.03(3H, d, J=7Hz), 3.50(1H, q, J=7Hz), 4.08(1H, d, J=15Hz), 4.19(1H, d, J=15Hz), 4.49(1H, d, J=14Hz), 4.90(1H, d, J=14Hz), 6.83–6.95(1H, m), 7.07–7.26(2H, m), 7.84(1H, s), 8.07(1H, s), 8.60(1H, s) SIMS(m/z): 451(MH$^+$) |
| 71 | (2R,3R)-Methylthiol deriv. (0.4 g) 4-Chloromethyl-2-cyclopropyl thiazole hydrochloride (0.35 g) | Ethanol (20 ml) 28% sodium methylate methanol solution (0.58 ml) 30 min. 20° C. | Compound 123•dihydrochloride(0.35 g, 61%): Colorless prisms (crystallized from ethyl ether) mp. 123–125° C. $^1$H-NMR(DMSO-d$_6$)δ: 0.95–1.21(7H, m), 2.36–2.50(1H, m), 3.33–3.55(2H, m), 3.86(1H, d, J=15Hz), 3.99(1H, d, J=15Hz), 4.45(1H, d, J=14Hz), 4.92(1H, d, J=14Hz), 6.83–6.92(1H, m), 7.08–7.26(2H, m), 7.31(1H, s), 7.92(1H, s), 8.76(1H, s) SIMS(m/z): 423(MH$^+$) $[\alpha]_D^{23}$ −89.0° (c = 1.0, in methanol) |
| 72 | (2R,3R)-Methylthiol deriv. (1.0 g) | Ethanol (10 ml) 28% sodium methylate | Compound 78•dihydrochloride (1.1 g, 69%): colorless powder $^1$H-NMR(DMSO-d$_6$)δ: |
| | 2-Chloromethyl-1-methyl imidazole hydrochloride (0.60 g) | methanol solution (1.44 ml) 22 min. 20° C. | 1.06(3H, d, J=7.0Hz), 3.44(1H, q, J=7.0Hz), 3.91(3H, s), 4.40(1H, d, J=15Hz), 4.52(1H, d, J=15Hz), 4.62(1H, d, J=14.2Hz), 4.98(1H, d, J=14.2Hz), 6.9–7.4(3H, m), 7.67(1H, s), 7.75(1H, s), 8.12(1H, s), 9.04(1H, s) SIMS(m/z): 380(MH$^+$) $[\alpha]_D^{25}$ −57.9° (c = 1.0, in methanol) |
| 73 | (2R,3R)-Methylthiol deriv. (0.50 g) 2-Chloromethyl imidazole[1,2-a]pyrazine (0.30 g) | Ethanol (5.0 ml) 28% sodium methylate methanol solution (0.36 ml) 20 min. 20° C. | Compound 124•dihydrochloride (0.60 g, 70%): colorless powder (crystallized from ethyl acetate) mp. 93–96° C. $^1$H-NMR(DMSO-d$_6$)δ: 1.09(3H, d, J=6.6Hz), 3.54(1H, q, J=6.6Hz), 4.20(1H, d, J=15Hz), 4.30(1H, d, J=15Hz), 4.70(1H, d, J=14.2Hz), 5.01(1H, d, J=14.2Hz), 6.9–7.4(3H, m), 7.98(1H, s), 8.23(1H, d, J=4.4Hz), 8.55(1H, s), 8.86(1H, s), 9.02(1H, d, J=4.4Hz), 9.49(1H, s), 11.4(1H, br.) $[\alpha]_D^{25}$ −72.0° (c = 0.94, in methanol) |
| 74 | (2R,3R)-Methylthiol deriv. (0.50 g) 2-Chloromethyl imidazole[1,2-a]pyrimidine (0.30 g) | Ethanol (5.0 ml) 28% sodium methylate methanol solution (0.36 ml) 15 min. 20° C. | Compound 125•dihydrochloride (0.60 g, 70%): colorless powder (crystallized from ethyl acetate) mp. 105–110° C. $^1$H-NMR(DMSO-d$_6$)δ: 1.11(3H, d, J=6.8Hz), 3.49(1H, q, J=6.8Hz), 4.20(1H, d, J=14.8Hz), 4.32(1H, d, J=14.8Hz), 4.76(1H, d, J=13.8Hz), 4.99(1H, d, J=13.8Hz), 6.8–7.4(3H, m), 7.69(1H, d, d, J=4.4Hz, 6.6Hz), 7.83(1H, s), 8.34(1H, s), 8.69(1H, s), 9.04(1H, d, d, J=1.6Hz, 4.4Hz), 9.41(1H, d, d, J=1.6Hz, 6.6Hz) $[\alpha]_D^{25}$ −66.2° (c = 1.0, in methanol) |
| 75 | (2R,3R)-Methylthiol deriv. (0.50 g) 3-Chloromethyl-5H-6,7-dihydropyrrolo[1,2-c]imidazole hydrochloride (0.34 g) | Ethanol (5.0 ml) 28% sodium methylate methanol solution (0.72 ml) 10 min. 20° C. | Compound 97•dihydrochloride (0.47 g, 56%): Colorless powder $^1$H-NMR(DMSO-d$_6$)δ: 1.11(3H, d, J=6.8Hz), 2.62(2H, m), 2.98(2H, t, J=7.0Hz), 3.42(1H, q, J=6.8Hz), 4.2–4.5(4H, m), 4.69(1H, d, J=14Hz), 4.93(1H, d, J=14Hz), 6.9–7.3(3H, m), 7.38(1H, s), 7.92(1H, s), 8.67(1H, s). $[\alpha]_D^{25}$ −54.5° (c = 0.60, in methanol) Elemental Analysis for C$_{19}$H$_{21}$F$_2$N$_5$OS•2HCl•H$_2$O: Calcd.: C, 45.97; H, 5.08; N, 14.11 Found: C, 46.11; H, 5.44; N, 13.67 |

Example 76

In methanol (25 ml) were dissolved (2S,3S)-2-(2,4-difluorophenyl)-3-methyl-2-[(1H-1,2,4-triazol-1-yl)methyl]oxirane (1.0 g), methyl 3-mercaptopropionate (3.5 ml) and 28% sodium methoxide-methanol (3.07 g) and the solution was refluxed in an oil bath. After 2 and after 3 hours, methyl 3-methylpropionate (1.75 ml) and 28% sodium methoxide-methanol (1.5 g) were added at each time. The oil bath was removed after heating for 4 hours and the reaction mixture was neutralized with cold 1N hydrochloric acid (32 ml) and extracted with dichloromethane (200 ml). The extract was washed with saturated aqueous sodium chloride solution and dried over anhydrous magnesium sulfate and the solvent was distilled off under reduced pressure. The residue was purified by silica gel chromatography (eluent: hexane-ethyl acetate=1:3). The desired fraction was concentrated and the resulting crystals were recrystallized from ethyl acetate-hexane to give (2S,3R)-2-(2,4-difluorophenyl)-3-mercapto-1-(1H-1,2,4-triazol-1-yl)-2-butanol (compound 117, 472 mg) as colorless needles.

m.p. 141–144° $[\alpha]_D^{25}+64.1°$ (c=1.0, methanol) Elemental Analysis for $C_{12}H_{13}F_2N_3OS$ Calcd.: C, 50.52; H, 4.59; N, 14.73 Found: C, 50.51; H, 4.59; N, 14.49 NMR (CDCl$_3$) δ: 1.52(3H,d,J=7 Hz), 1.54(1H,d,J=6 Hz), 3.69(1H,m), 4.56(1H,s), 4.62(1H,d,J=14 Hz), 4.94(1H,dd,J=14 Hz,J=1.8 Hz), 6.68–6.81(2H,m), 7.30–7.43(1H,m), 7.73(1H,s), 7.95(1H,s) IR (KBr) cm$^{-1}$: 3260, 1615, 1500, 1420, 1260, 1200, 1125

Example 77

In trifluoroacetic acid (75 ml) were dissolved 1-[1-(2,4-difluorophenyl)-1-hydroxy-2-(1H-1,2,4-triazol-1-yl)-ethyl]-1-(4-methoxybenzylthio)cyclopropane (4.26 g), anisole (26 ml) and mercury (II) acetate (3.58 g) and the solution was stirred at room temperature for 2 hours. The reaction mixture was then concentrated under reduced pressure, the residue was diluted with petroleum ether (50 ml), and the supernatant layer was removed. To the residue was added ether (30 ml), whereupon the mercuric compound separated out as a colorless powder. The powder was collected by filtration and washed with a small amount (10 ml) of ether. This product (6.2 g) was suspended in dichloromethane (150 ml) and hydrogen sulfide was bubbled into the suspension at room temperature for 30 minutes. The resulting precipitate was filtered off and the filtrate was concentrated under reduced pressure. The residue was subjected to silica gel chromatography (2.5×40 cm), and elution was carried out with ethyl acetate-hexane (3:1). The desired fraction was concentrated and the residue was treated with isopropyl ether to give compound 120 (2 g) as colorless needles. m.p. 92°–94° C.

$^1$H-NMR (CDCl$_3$) δ: 0.72–1.28(4H,m), 2.26(1H,s), 4.80(1H,d,d,J=1.6 Hz,14 Hz), 5.19(1H,bs), 5.31(1H,d,d,J=1.6 Hz,14 Hz), 6.63–6.88(2H,m), 7.54–7.66(1H,m), 7.81(1H,s), 8.14(1H,d,J=1.6 Hz) Elemental Analysis for $C_{13}H_{13}F_2N_3OS$ Calcd.: C, 52.52; H, 4.41; N, 14.13 Found: C, 52.41; H, 4.45; N, 13.97.

Example 78

In methanol (25 ml) were dissolved (2R,3R)-2-(2,4-difluorophenyl)-3-methyl-2-[(1H-1,2,4-triazol-1-yl)methyl]oxirane (0.98 g), methyl 3-mercaptopropionate (3.3 ml) and 28% sodium methoxide-methanol (3.0 g) and the solution was refluxed on an oil bath. After 2 and after 3 hours, methyl 3-methylpropionate (0.83 ml) and 28% sodium methoxide-methanol (0.75 g) were added at each time. The oil bath was removed after heating for 4 hours and the reaction mixture was neutralized with cold 1N-HCl (23.4 ml) and extracted with dichloromethane (200 ml). The extract was washed with saturated aqueous sodium chloride solution and dried over anhydrous magnesium sulfate and the solvent was distilled off under reduced pressure. The residue was purified by silica gel chromatography (eluent: hexane-ethyl acetate=1:3). The desired fraction was concentrated and the resulting crystals were recrystallized from ethyl acetate-hexane to give (2R,3S)-2-(2,4-difluorophenyl)-3-mercapto-1-(1H-1,2,4-triazol-1-yl)-2-butanol (compound 118, 461 mg) as colorless needles. m.p. 141°–143° C.

$[\alpha]_D^{25}-63.4°$ (c=1.0, methanol) Elemental Analysis for $C_{12}H_{13}F_2N_3OS$ Calcd.: C, 50.52; H, 4.59; N, 14.73 Found: C, 50.51; H, 4.68; N, 14.53 NMR (CDCl$_3$) δ: 1.52(3H,d,J=7 Hz), 1.54(1H,d,J=6 Hz), 3.69(1H,m), 4.55(1H,s), 4.62(1H,d,J=14 Hz), 4.93(1H,dd,J=14 Hz,J=1.8 Hz), 6.68–6.82(2H,m), 7.29–7.45(1H,m), 7.72(1H,s), 7.95(1H,s) IR(KBr)cm$^{-1}$: 3260, 1615, 1500, 1420, 1260, 1200, 1120

Example 79

In trifluoroacetic acid (20 ml) were dissolved 3-(4-methoxybenzylthio)-2-(2,4-difluorophenyl)-3-methyl-1-(1H-1,2,4-triazol-1-yl)-2-butanol (1.23 g), anisole (7.5 ml) and mercury (II) acetate (1.03 g) and the solution was stirred at room temperature for 2 hours. The reaction mixture was then concentrated under reduced pressure, the residue was diluted with petroleum ether (20 ml), and the supernatant layer was removed. To the residue was added ether (20 ml). The resulting colorless powder was collected by filtration and washed with a small quantity (5 ml) of ether to give the mercuric compound (1.6 g). This product (1.6 g) was suspended in dichloromethane (50 ml) and hydrogen sulfide was bubbled into the suspension at room temperature for 20 minutes. After the precipitate was filtered off, N$_2$ gas was bubbled into the filtrate for 15 minutes and the solvent was then distilled off under reduced pressure. The residue was subjected to silica gel chromatography (2.5×20 cm), elution being carried out with ethyl acetate-hexane (3:1). The desired fraction was concentrated and isopropyl ether was added to the residue to give compound 119 (0.6 g) as colorless needles. m.p. 95°–96° C.

$^1$H-NMR (CDCl$_{33}$) δ: 1.39(3H,s), 1.42–1.48(3H,m), 2.39(1H,s), 4.93(1H,d,d,J=2.6 Hz,14 Hz), 5.32(1H,d,d,J=2.6 Hz,14 Hz), 5.44(1H,s), 6.59–6.85(2H,m), 7.62–7.71(1H,m), 7.75(1H,s), 8.08(1H,d,J=2.6 Hz) Elemental Analysis for $C_{13}H_{15}F_2N_3OS$ Calcd.: C, 52.16; H, 5.05; N, 14.04 Found: C, 52.13; H, 5.10; N, 14.03.

Examples 80–85

In a manner like that described in Example 64, (2R,3R)-2-(2,4-difluorophenyl)-3-mercapto-1-(1H-1,2,4-triazole-1-yl)-2-butanol [in Table 15, simply referred to "(2R,3R)-methyl thiol deriv."] was allowed to react with the chloro-compound shown in Table 15 to afford Compound 90, 91, 126–129.

TABLE 15

| Ex. No. | Starting compounds | Reaction conditions | Products |
|---|---|---|---|
| 80 | (2R,3R)- | Ethanol | Compound 126 (0.37 g, |

TABLE 15-continued

| Ex. No. | Starting compounds | Reaction conditions | Products |
|---|---|---|---|
|  | Methylthiol deriv. (0.50 g) 4-Chloromethyl pyrimidine (0.22 g) | (5.0 ml) 28% sodium methylate-methanol solution (0.36 ml) 17 min. 20° C. | 56%): Colorless needles (crystallized from a mixture of diethylether and diisopropylether) mp. 113–113.5° C. $^1$H-NMR(CDCl$_3$)δ: 1.19(3H, d, J=7.0Hz), 3.48(1H, q, J=7.0Hz), 3.86(1H, d, J=14.2Hz), 4.07(1H, d, J=14.2Hz), 4.66(1H, d, J=14.2Hz), 5.04(1H, d, J=14.2Hz), 5.84(1H, s), 6.68–6.78(2H, m), 7.33–7.45(1H, m), 7.44(1H, d, J=5.2Hz), 7.76(2H, s), 8.73(1H, d, J=5.2Hz), 9.23(1H, s) $[α]_D^{25}$ −86.8° (c = 1.0, in methanol) Elemental Analysis for C$_{17}$H$_{17}$F$_2$N$_5$OS: Calcd.: C, 54.10; H, 4.54; N, 18.56 Found: C, 54.13; H, 4.55; N, 18.39 |
| 81 | (2R,3R)-Methylthiol deriv. (0.50 g) 4-Chloromethyl pyrimidine hydrochloride (0.31 g) | Ethanol (5.0 ml) 28% sodium methylate-methanol solution (0.72 ml) 12 min. 20° C. | Compound 127•2HCl (0.54 g, 67%) pale brown powder $^1$H-NMR(DMSO-d$_6$)δ: 1.05(3H, d, J=6.6Hz), 2.74(3H, s), 3.64(1H, q, J=6.6Hz), 3.96(1H, d, J=13.8Hz), 4.11(1H, d, J=13.8Hz), 4.58(1H, d, J=14.4Hz), 4.93(1H, d, J=14.4Hz), 6.9–7.0(1H, m), 7.1–7.3(2H, m), 7.68(1H, d, J=4.8Hz), 8.05(1H, s), 8.85(1H, d, J=4.8Hz), 8.89(1H, s) |
| 82 | (2R,3R)-Methylthiol deriv. (0.6 g) 5-Amino-3-chloromethyl-1,2,4-thiadiazole (0.34 g) | Ethanol (15 ml) 28% sodium methylate-methanol solution (0.4 ml) 30 min. 20° C. | Compound 128•dihydrochloride (0.38 g, 39%): colorless powder $^1$H-NMR(DMSO-d$_6$)δ: 1.02(3H, d, J=7Hz), 3.61(1H, q, J=7Hz), 3.73(1H, d, J=15Hz), 3.86(1H, d, J=15Hz), 4.58(1H, d, J=14Hz), 4.97(1H, d, J=14Hz), 6.83–6.96(1H, m), 7.08–7.28(2H, m), 7.95(1H, s), 8.74(1H, s) |
| 83 | (2R,3R)-Methylthiol deriv. (0.50 g) 3-Chloromethyl-imidazo[1,2-a]pyridazine | Ethanol (5.0 ml) 28% sodium methylate-methanol solution (0.72 ml) 25 min. 20° C. | Compound 129•dihydrochloride (0.63 g, 73%) Colorless powder (crystallized from a mixture of ethanol, methylene chloride and ethylether. mp. 95–99° C. $^1$H-NMR(DMSO-d$_6$)δ: 1.01(3H, d, J=7.8Hz), 3.47(1H, q, J=7.8Hz), 4.30(2H, s), 4.31(1H, d, J=13.8Hz), 4.74(1H, d, J=13.8Hz), 5.94(1H, s), 6.8–7.0(1H, m), 7.0–7.4(3H, m), 7.59(1H, s), 7.83(1H, s), 8.15(1H, d, J=9.2Hz), 8.21(1H, s), 8.61(1H, d, J=2.6Hz) $[α]_D^{25}$ −87.7° (c = 0.56, in methanol) |
| 84 | (2R,3R)-Methylthiol | Ethanol (5.0 ml) | Compound 90•dihydrochloride (0.41 g, 51%) |
|  | deriv. (0.50 g) 4-Chloromethyl-1-methyl imidazole hydrochloride (0.27 g) | 28% sodium methylate methanol solution (0.72 ml) 10 min. 20° C. | colorless powder $^1$H-NMR(DMSO-d$_6$)δ: 1.07(3H, d, J=7.0Hz), 3.38(1H, q, J=7.0Hz), 3.88(3H, s), 3.98(1H, d, J=14.8Hz), 4.11(1H, d, J=14.8Hz), 4.69(1H, d, J=14.2Hz), 5.05(1H, d, J=14.2Hz), 6.9–7.4(3H, m), 7.66(1H, s), 7.97(1H, s), 8.85(1H, s), 9.14(1H, s) |
| 85 | (2R,3R)-Methylthiol deriv. (0.50 g) 5-Chloromethyl-1-methyl imidazole hydrochloride (0.27 g) | Ethanol (5.0 ml) 28% sodium methylate methanol solution (0.72 ml) 10 min. 20° C. | Compound 91 (0.40 g, 60%): colorless needles (crystallized from diethylether) mp. 133–134° C. $^1$H-NMR(CDCl$_3$)δ: 1.11(3H, d, J=7.2 Hz), 3.19(1H, q, J=7.2Hz), 3.72(3H, s), 3.80(1H, d, J=14.6Hz), 3.89(1H, d, J=14.6Hz), 4.45(1H, d, J=14.6Hz), 4.82(1H, d, J=14.6Hz), 5.00(1H, br.), 6.66–6.75(2H, m), 6.99(1H, s), 7.27–7.38(1H, m), 7.46(1H, s), 7.72(1H, s), 7.75(1H, s) |

Example 86

In ethyl acetate (20 ml) was dissolved (2R,3R)-2-(2,4-difluorophenyl)-3-mercapto-1-(1H-1,2,4-triazol-1-yl)-2-butanol (compound 43, 0.2 g) and the solution was concentrated to about 10 ml under reduced pressure. The concentrate was allowed to stand at room temperature, whereupon compound 43 separated out as colorless prisms. X-ray crystallography of this product gave the following findings.

| Crystal Data | |
|---|---|
| Formula | C$_{12}$H$_{13}$N$_3$OF$_2$S |
| Formula Weight | 285.31 |
| Crystal System | orthorhombic |
| Cell Dimensions | a = 10.754(1)Å |
|  | b = 13.771(2)Å |
|  | c = 9.069(1)Å |
| Cell Volume | 1343.2(3)Å$^3$ |
| Space Group | P2$_1$2$_1$2$_1$ |
| Number of Formula Units in the Unit Cell | 4 |
| Calculated Density | 1.411 g/cm$^3$ |
| Radiation | Mo-Kα (λ = 0.71069Å) |
| Final R-value | 0.041 |

Example 87

In ethyl acetate (10 ml) was dissolved (2R,3R)-2-(2,4-difluorophenyl)-3-mercapto-1-(1H-1,2,4-triazol-1-yl)-2-butanol (compound 43, 0.2 g) followed by addition of 4 N HCl-ethyl acetate (1 ml). The mixture was concentrated under reduced pressure to about 1 ml, whereupon crystals separated out. Then, ethyl ether (2 ml) was added and the mixture was filtered to give compound 43 hydrochloride (0.15 g) as colorless needles. m.p. 155°–162° C.

Elemental Analysis for C$_{12}$H$_{13}$F$_2$N$_3$OS.HCl Calcd.: C, 44.79; H, 4.39; N, 13.06 Found: C, 44.77; H, 4.48; N, 12.85

X-ray powder diffraction pattern: FIG. 1

Example 88

In ethyl acetate (20 ml) was dissolved (2R,3R)-2-(2,4-difluorophenyl)-3-mercapto-1-(1H-1,2,4-triazol-1-yl)-2-butanol (compound 43, 0.48 g) followed by addition of 25% hydrogen bromide-acetic acid (0.7 ml). The reaction mixture was diluted with 100 ml of hexane and the resulting powder was collected by filtration and dissolved in ethyl acetate (10 ml). The solution was allowed to stand after addition of ethyl ether (20 ml) and the resulting crystals were collected by filtration to yield compound 43 hydrobromide (0.35 g) as colorless platelets. m.p. 180°–185° C.

Elemental Analysis for $C_{12}H_{13}F_2N_3OS \cdot HBr$ Calcd.: C, 39.36; H, 3.85; N, 11.47 Found: C, 39.28; H, 3.85; N, 11.32.

Figure 2:
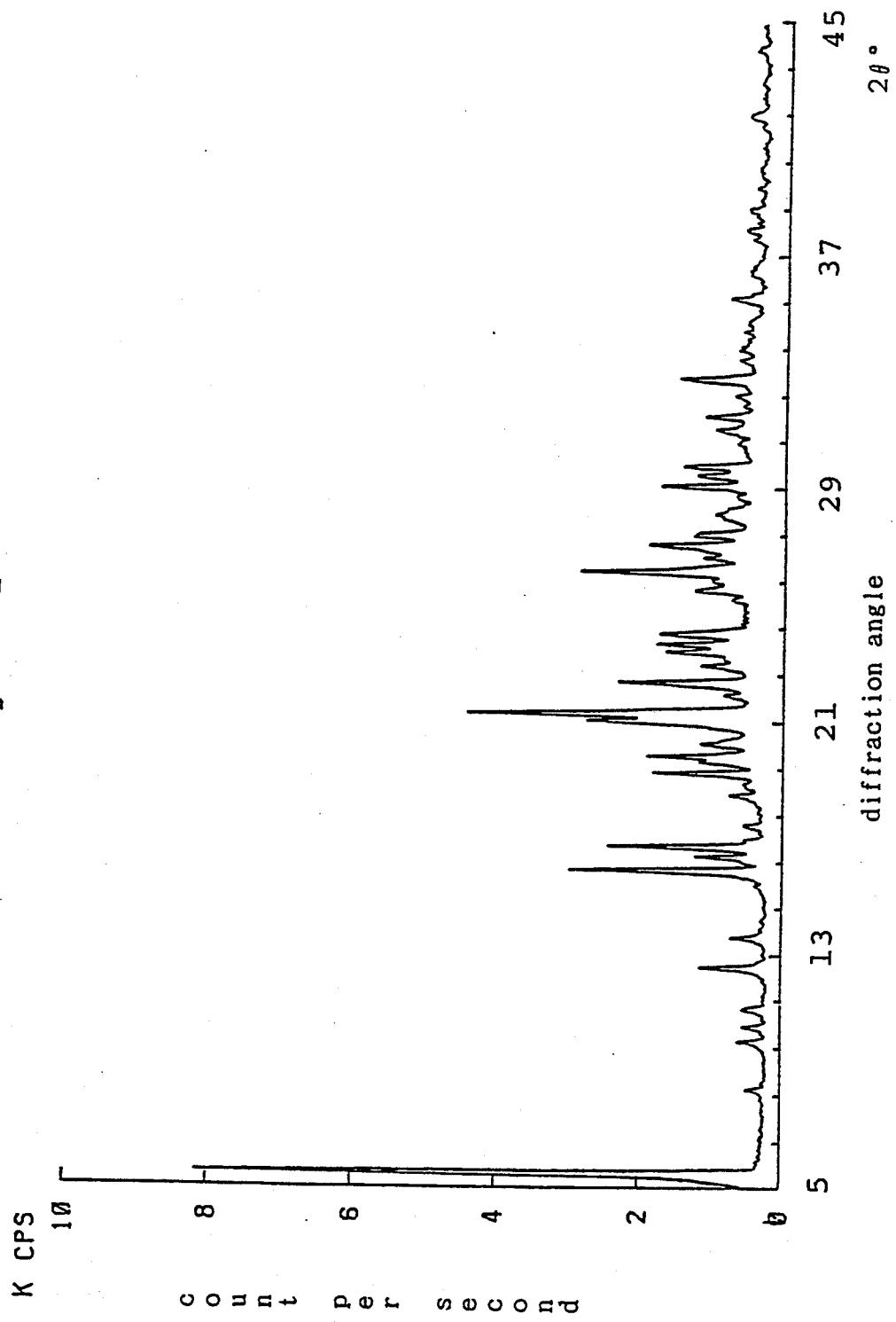
FIG. 2 shows an X-ray powder diffraction pattern of compound 43 hydrobromide.

X-ray powder diffraction pattern: FIG. 2

Examples 89–93

In a manner like that described in Example 64, (2R,3R)-2-(2,4-difluorophenyl)-3-mercapto-1-(1H-1,2,4-triazol-1-yl)-2-butanol [in Table 16, simply referred to "(2R,3R)-methyl thiol deriv."] was allowed to react with the chloro compound shown in Table 16 to afford Compound 95, 101, 102, 130, 131.

TABLE 16

| Ex. No. | Starting compounds | Reaction conditions | Products |
|---|---|---|---|
| 89 | (2R,3R)-Methylthiol deriv. (0.16 g) 3-Chloromethyl imidazo[1,5-a]pyrimidine hydrochloride (0.2 g) | Ethanol (2.0 ml) 28% sodium methylate-methanol solution (0.24 ml) 10 min. 20° C. | Compound 130 (0.04 g, 17%) Colorless oily substance $^1$H-NMR(CDCl$_3$)δ: 1.11(3H, d, J=7.0Hz), 3.34(1H, q, J=7.0Hz), 4.22(1H, d, J=15Hz), 4.33(1H, d, J=15Hz), 4.42(1H, d, J=14.2Hz), 4.77(1H, d, J=14.2Hz), 5.55(1H, br), 6.6–6.8(2H, m), 6.67(1H, d, d, J=5.4Hz, 8.2Hz), 7.3–7.4(1H, m), 7.62(1H, s), 7.71(1H, s), 7.75(1H, s), 8.20(1H, d, d, J=1.8Hz, 5.4Hz), 8.26(1H, d, d, J=1.8Hz, 8.2Hz) This product was dissolved in a mixture of ethyl acetate and diethyl ether, to which was added a hydrogen chloride-ethyl acetate solution (1.0 ml). Crystals then precipitated were collected by filtration to obtain Compound 130•dihydrochloride (0.02 g) m.p. 118–127° C. |
| 90 | (2R,3R)-Methylthiol deriv. (0.28 g) 7-Chloromethyl imidazo[1,5-b]pyridazine hydrochloride (0.2 g) | Ethanol (3.0 ml) 28% sodium methylate-methanol solution (0.40 ml) 10 min. 20° C. | Compound 131 (0.06 g, 15%) Colorless powder (crystallized from a mixture of methanol and diethylether) mp. 210–220° C. $^1$H-NMR(DMSO-d$_6$)δ: 1.01(3H, d, J=6.8Hz), 3.67(1H, q, J=6.8Hz), 4.34(1H, d, J=14.4Hz), 4.35(1H, d, J=14.2Hz), 4.40(1H, d, J=14.4Hz), 4.73(1H, d, J=14.2Hz), 6.1(1H, br.), 6.79–7.30(4H, m), 7.59(1H, s), 7.62(1H, s), 8.18(1H, d, J=9.2Hz), 8.28(1H, s), 8.40(1H, d, J=4.2Hz) |
| 91 | (2R,3R)-Methylthiol deriv. (0.75 g) 2-Chloromethyl-1-ethyl imidazol hydrochloride (0.48 g) | Ethanol (7.5 ml) 28% sodium methylate-methanol solution (1.08 ml) 10 min. 20° C. | Compound 101 (0.82 g, 79%) Colorless prisms (crystallized from ethyl ether) mp. 120–121° C. $^1$H-NMR(CDCl$_3$)δ: 1.22(3H, d, J=7.0Hz), 1.45(3H, t, J=7.4Hz), 3.54(1H, q, J=7.0Hz), 3.75(1H, d, J=15.4Hz), 3.99(2H, q, J=7.4Hz), 4.06(1H, d, J=15.4Hz), 4.59(1H, d, J=14.4Hz), 4.84(1H, d, J=14.4Hz), 6.68–6.77(2H, m), 6.90(1H, s), 7.00(1H, s), 7.34(1H, br.), 7.39–7.52(1H, m), 7.66(1H, s), 8.00(1H, s) |
| 92 | (2R,3R)-Methylthiol deriv. (0.75 g) 2-Chloromethyl-1-isopropyl imidazol hydrochloride (0.51 g) | Ethanol (7.5 ml) 28% sodium methylate-methanol solution (1.08 ml) 10 min. 20° C. | Compound 102 (0.84 g, 79%) Colorless prisms (crystallized from ethyl ether) mp. 159–160° C. $^1$H-NMR(CDCl$_3$)δ: 1.22(3H, d, J=6.8Hz), 1.47(6H, d, J=6.8Hz), 3.54(1H, q, J=6.8Hz), 3.77(1H, d, J=15.4Hz), 4.08(1H, d, J=15.4Hz), 4.44(1H, sep. J=6.8Hz), 4.62(1H, d, J=14.6Hz), 4.83(1H, d, J=14.6Hz), 6.68–6.79(2H, m), 6.96(1H, s), 7.02(1H, s), 7.33(1H, br.), 7.43–7.52(1H, m), 7.66(1H, s), 8.00(1H, s) |
| 93 | (2R,3R)-Methylthiol deriv. (0.75 g) 3-Chloromethyl-4-methyl triazole hydrochloride (0.44 g) | Ethanol (7.5 ml) 28% sodium methylate-methanol solution (1.08 ml) 10 min. 20° C. | Compound 95 (0.90 g, 90%) Colorless powder (crystallized from methanol-ethyl ether) mp. 102–107° C. $^1$H-NMR(CDCl$_3$)δ: 1.12(3H, d, J=7.0Hz), 3.47(1H, q, J=7.0Hz), 3.76(3H, s), 3.97(1H, d, J=15Hz), 4.06(1H, d, J=15Hz), 4.60(1H, d, J=14.2Hz), 4.81(1H, d, J=14.2Hz), 5.36(1H, s), 6.65–6.77(2H, m), 7.30–7.39(1H, m), 7.73(1H, s), 7.80(1H, s), 8.12(1H, s) |

Example 94

To the solution of 2-(2,4-difluorophenyl)-2-(1H-1,2,4-triazol-1-ylmethyl)oxirane (8.0 g) and 3-mercaptopropionic acid methyl ester (11.2 ml) in dimethylformaide (160 ml) was added 60% sodium hydride suspension in oil (4.0 g), and the mixture was stirred for 15 minutes. 1N aqueous hydrochloric acid solution (101 ml) was added dropwise to adjust pH to 7, and dimethylformamide and water were evaporated off under reduced pressure. To the residue was added 20 ml of water, followed by extraction with ethyl acetate (50 ml×3). The extract was washed with saturated aqueous sodium chloride solution, and dried over anhydrous sodium sulfate, followed by evaporation under reduced pressure. The residue was subjected to silica gel column chromatography (6.0×9.0 cm) and eluted with ethyl acetate-hexane (3:1). The desired fraction was concentrated, and to the residue was added diethyl ether, to give 2-(2,4-difluorophenyl)-3-mercapto-1-(1H-1,2,4-triazol-1-yl)propan-2-ol (6.44 g) as colorless needles. mp. 112°–113° C.

Elemental analysis for $C_{11}H_{11}F_2N_3OS$ Calc.: C, 48.70; H, 4.09; N, 15.49 Found: C, 48.96; H, 4.11; N, 15.62.

Example 95

A methanol solution (75 ml) containing (2R,3S)-2-(2,4-difluorophenyl)-2-(1-imidazolyl)methyl-3-methyloxirane (2.5 g), methyl 3-mercaptopropionate (5.5 ml) and 28% sodium methoxide-methanol (8.1 ml) was refluxed for 1.5 hours. Then, methyl 3-mercaptopropionate (5.5 ml) and 28% sodium methoxide-methanol (8.1 ml) were added and the mixture was further refluxed for 2 hours. The reaction mixture was cooled with ice, neutralized with 5N hydrochloric acid (16 ml), diluted with saturated aqueous sodium chloride solution (100 ml) and extracted with ethyl acetate (200 ml×3). The extract was dried over anhydrous magnesium sulfate and the solvent was distilled off under reduced pressure. The residue was dissolved in methylene chloride (40 ml), followed by addition of 1N aqueous sodium hydroxide solution (8 ml) and water (100 ml). The aqueous layer was further extracted with methylene chloride (40 ml×3). The methylene chloride layers were combined and extracted 5 times with water (30 ml) containing 1N hydrochloric acid (8 ml). The aqueous layers were combined, neutralized with sodium hydroxide and extracted with methylene chloride (40 ml×4). The extract was dried over anhydrous magnesium sulfate and the solvent was distilled off under reduced pressure. The residue was subjected to silica gel chromatography (4 cm×15 cm) using methanol-methylene chloride (5:95) as the eluent. The desired fraction was concentrated and diethyl ether was added to the residue to yield (2R,3R)-2-(2,4-difluorophenyl)-1-(1-imidazolyl)-3-mercapto-2-butanol (0.84 g) as colorless prisms.

$^1$H-NMR (CDCl$_3$) δ: 1.12(3H,d,J=7.0 Hz), 1.69(1H,d,J=6.0 Hz), 3.68(1H,m), 4.45(1H,d.d.,J=1.4 Hz, 14.2 Hz), 4.59(1H,d,J=14.2 Hz), 6.57(1H,s), 6.71(1H,s), 6.7–6.85(2H,m), 7.28(1H,s), 7.3–7.5(1H,m) m.p. 125°–135° C. Elemental Analysis for $C_{13}H_{14}F_2N_2OS$ Calcd.: C, 54.92; H, 4.96; N, 9.85 Found: C, 54.94; H, 5.10; N, 9.62 IR(KBr)cm$^{-1}$: 3000, 1610, 1590, 1500, 1420, 1260, 1200, 1130

The above compound was dissolved in diethyl ether, and hydrochloric acid-diethyl ether wad added. The resulting powder was recrystallized from ethanol-diethyl ether to give the hydrochloride as colorless prisms.

$^1$H-NMR (DMSO-d$_6$) δ: 1.06(3H,d,J=6.8 Hz), 2.95(1H,d,J=9.2 Hz), 3.63(1H,m), 4.65(1H,d,J=14.6 Hz), 4.92(1H,d,J=14.6 Hz), 6.31(1H,s), 6.98(1H,d.t,J=2.8 Hz, 8.8 Hz), 7.20–7.37(2H,m), 7.29(1H,s), 7.45(1H,s), 8.85(1H,s) Elemental Analysis for $C_{13}H_{15}F_2N_2OS \cdot HCl \cdot \frac{1}{2}H_2O$ Calcd.: C, 47.34; H, 4.89; N, 8.49 Found: C, 46.74; H, 4.43; N, 8.44 IR(KBr)cm$^{-1}$: 3270, 3000, 1600, 1490, 1410, 1260, 1120

What is claimed is:

1. A compound of the formula (I):

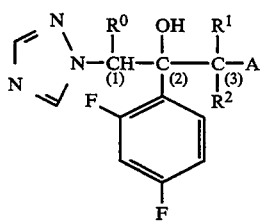

wherein $R^0$ and $R^2$ are each hydrogen;
$R^1$ is methyl;
A represents a group of the formula

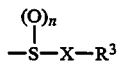

n is 0, 1 or 2;
$R_3$ is an aromatic heterocyclic group selected from the group consisting of [1-(1H)-1,2,4-triazolyl,] 3-(4H)-1,2,4-triazolyl, [3-(1H)-1,2,4-triazolyl,] 5-(1H)-1,2,4-triazolyl, [4-(4H)-1,2,4-triazolyl, 1,2,3-triazolyl], wherein said aromatic heterocyclic group is unsubstituted or substituted with $C_{1-4}$ alkyl;
X is of the formula

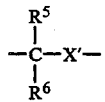

X' is a single bond; and
$R^5$ and $R^6$, which may be the same or different, are independently hydrogen or a lower alkyl group;
or a pharmacologically acceptable salt thereof.

2. A compound according to claim 1, wherein $R^3$ is 1,2,4-triazol-3-yl optionally substituted by $C_{1-4}$ alkyl.

3. A compound according to claim 1, wherein the compound is (2R,3R)-2-(2,4-difluorophenyl)-3-[(4-methyl-4H-1,2,4-triazol-3-yl)methylthio]-1-(1H-1,2,4-triazol-1-yl)-2-butanol.

4. A compound according to claim 1, wherein the compound is (2R,3R)-2-(2,4-difluorophenyl)-3-[(1-methyl-1H-1,2,4-triazol-5-yl)methylthio]-1-(1H-1,2,4-triazol-1-yl)-2-butanol.

5. An antifungal composition comprising an antifungally effective amount of a compound of formula (I) as defined in claim 1 or a pharmacologically acceptable salt thereof, and a pharmacologically acceptable carrier.

6. An antifungal composition according to claim 5, wherein $R^3$ is 1,2,4-triazol-3-yl optionally substituted by $C_{1-4}$ alkyl.

7. An antifungal composition according to claim 5, wherein the compound is (2R,3R)-2-(2,4-difluorophenyl)-3-[(4-methyl-4H-1,2,4-triazol-3-yl)methylthio]-1-(1H-1,2,4-triazol-1-yl)-2-butanol or a pharmaceutically acceptable salt thereof.

8. An antifungal composition according to claim 5, wherein the compound is (2R,3R)-2-(2,4-difluorophenyl)-3-[(1-methyl-1H-1,2,4-triazol-5-yl)methylthio]-1-(1H-1,2,4-triazol-1-yl)-2-butanol.

* * * * *